(12) United States Patent
Lockridge et al.

(10) Patent No.: US 7,070,973 B2
(45) Date of Patent: Jul. 4, 2006

(54) BUTYRYLCHOLINESTERASE VARIANTS AND METHODS OF USE

(75) Inventors: Oksana Lockridge, Bellevue, NE (US); Jeffry D. Watkins, Encinitas, CA (US)

(73) Assignees: Board of Regents of the University of Nebraska, Omaha, NE (US); Applied Molecular Evolution, San Diego, CA (US)

( * ) Notice: Subject to any disclaimer, the term of this patent is extended or adjusted under 35 U.S.C. 154(b) by 230 days.

(21) Appl. No.: 09/748,739

(22) Filed: Dec. 26, 2000

(65) Prior Publication Data

US 2002/0119489 A1 Aug. 29, 2002

(51) Int. Cl.
*A61K 38/46* (2006.01)
*C12N 9/18* (2006.01)

(52) U.S. Cl. ............... 435/197; 435/196; 424/94.6; 530/350

(58) Field of Classification Search ............... 435/7.1, 435/196–197; 424/94.6; 530/350
See application file for complete search history.

(56) References Cited

U.S. PATENT DOCUMENTS

| 5,264,563 A | | 11/1993 | Huse ..................... 536/25.3 |
| 5,830,721 A | | 11/1998 | Stemmer et al. ......... 435/172.1 |
| 6,001,625 A | * | 12/1999 | Broomfield et al. ........ 435/197 |
| 2003/0096401 A1 | * | 5/2003 | Huse ..................... 435/325 |
| 2003/0153062 A1 | * | 8/2003 | Watkins et al. ............ 435/196 |

FOREIGN PATENT DOCUMENTS

WO 99/66072 * 12/1999

OTHER PUBLICATIONS

U.S. Appl. No. 60/367,370.*
OM protein—protein search using, sw model: Result 1 US to 2003/0096401.*
Abremski et al., "Studies on the properties of P1 site-specific recombination: evidence for topologically unlinked products following recombination," *Cell* 32:1301-1311 (1983).
Bethke and Sauer, "Segmental genomic replacement by Cre-mediated recombination: genotoxic stress activation of the p53 promoter in single-copy transformants," *Nuc. Acids Res.* 25:2828-2834 (1997).
Blong et al., "Tetramerization domain of human butyrylcholinesterase is at the C-terminus," *Biochem. J.* 327:747-757 (1997).
Crameri et al., "DNA shuffling of a family of genes from diverse species accelerates directed evolution," *Nature* 391:288-291 (1998).
Dymecki, "Flp recombinase promotes site-specific DNA recombination in embryonic stem cells and transgenic mice," *Proc. Natl. Acad. Sci. U.S.A.* 93:6191-6196 (1996).
Fukushige and Sauer, "Genomic targeting with a positive-selection *lox* integration vector allows highly reproducible gene expression in mammalian cells," *Proc. Natl. Acad. Sci. USA* 89:7905-7909 (1992).
Glaser et al., "Antibody engineering by codon-based mutagenesis in a filamentous phage vector system," *J. Immunology* 149:3903-3913 (1992).
Gorelick, "Enhancing cocaine metabolism with butyrylcholinesterase as a treatment strategy," *Drug Alcohol Depend.* 48:159-165 (1997).
Harel et al., "Conversion of acetylcholinesterase to butyrylcholinesterase: modeling and mutagenesis," *Proc. Nat. Acad. Sci. USA* 89: 10827-10831 (1992).
Hoess et al., "The role of the *loxP*spacer region in P1 site-specific recombination," *Nucleic Acids Res.* 14:2287-2300 (1986).
Kunkel, "Rapid and efficient site-specific mutagenesis without phenotypic selection," *Proc. Natl. Acad. Sci. USA* 82:488-492 (1985).
Lockridge et al., "A single amino acid substitution, Gly117His, confers phosphotriesterase (organophosphorus acid anhydride hydrolase) activity on human butyrylcholinesterase," *Biochemistry* 36:786-795 (1997).
Masson et al., "Role of aspartate 70 and tryptophan 82 in binding of succinyldithiocholine to human butyrylcholinesterase," *Biochemistry* 36:2266-2277 (1997).
Sauer and Henderson, "Site-specific DNA recombination in mammalian cells by the Cre recombinase of bacteriophage P1," *Proc. Natl. Acad. Sci. USA* 85:5166-5170 (1988).

(Continued)

*Primary Examiner*—Bennett Celsa
(74) *Attorney, Agent, or Firm*—Paula K. Davis

(57) ABSTRACT

The invention provides four butyrylcholinesterase variants having increased cocaine hydrolysis activity as well as the corresponding encoding nucleic acids. The invention also provides libraries comprising butyrylcholinesterase variants having at least one amino acid alteration in one or more regions of butyrylcholinesterase and further having at least one butyrylcholinesterase variant exhibiting enhanced cocaine hydrolysis activity compared to butyrylcholinesterase. The invention further provides methods of hydrolyzing a cocaine-based butyrylcholinesterase substrate as well as methods of treating a cocaine-induced condition.

2 Claims, 11 Drawing Sheets

OTHER PUBLICATIONS

Schwarz et al., "Engineering of human cholinesterase explains and predicts diverse consequences of administration of various drugs and poisons," *Pharmac. Ther.* 67:283-322 (1992).

Soreq et al., "Excavations into the active-site gorge of cholinesterases," *Trends Biochem. Sci.* 17:353-358 (1992).

Stemmer, "DNA shuffling by random fragmentation and reassembly: *in vitro* recombination for molecular evolution," *Proc. Natl. Acad. Sci. USA* 91:10747-10751 (1994).

Sussman et al., "Atomic structure of acetylcholinesterase from *Torpedo californica*: a prototypic acetylcholine-binding protein," *Science* 253:872-879 (1991).

Tatusova and Madden, "BLAST 2 Sequences, a new tool for comparing protein and nucleotide sequences," *FEMS Microbiol Lett.* 174:247-250 (1999).

Watkins et al., "Determination of the relative affinities of antibody fragments expressed in *Escherichia coli* by enzyme-linked immunosorbent assay," *Anal. Biochem.* 253:37-45 (1997).

Wu et al., "Humanization of a murine monoclonal antibody by simultaneous optimization of framework and CDR residues," *J. Mol. Biol.* 294:151-162 (1999).

Wu et al., "Stepwise *in vitro* affinity maturation of Vitaxin, an $\alpha_v\beta_3$- specific humanized mAb," *Proc. Natl. Acad. Sci. USA* 95:6037-6042 (1998).

Xie et al., "An improved cocaine hydrolase: the A328Y mutant of human butyrylcholinesterase is 4-fold more efficient," *Molecular Pharmacology* 55:83-91 (1999).

Ashani, "Prospective of human butyrylcholinesterase as a detoxifying antidote and potential regulator of controlled-release drugs," *Drug Development Research* 50:298-308 (2000).

Sun et al., "Re-engineering bytyrylcholinesterase as a cocain hydrolase," 30th Annual meeting of the Society fo Neuroscience; New Orleans, LA, USA; *Society for Neuroscience Abstracts* 26:675.10 (2000).

GenBank Accession No. AAE40560.
GenBank Accession No. AAZ49470.
GenBank Accession No.: AAY44573.
GenBank Accession No.: AAY59235.
GenBank Accession No.: AR070208.
GenBank Accession No.: M16541.

* cited by examiner

```
                          T7 primer
              TTAATACGACTCACTATAGGG  AGACCCG AAG CTT  AAG GTG CAC GGC CCA CGT GGA TCG ATC GCG CGC AGA TCT TCG GAA
        -28                                           Hind 3                                              Bgl II
              Met Asp Ser Lys Val Thr Ile Ile Cys Ile Arg Phe Trp Phe Leu Phe Leu Leu Cys Met Leu Ile Gly Lys Ser His Thr
              GCC ACC ATG GAT AGC AAA AAA GTC ACA ATC ACA ATC ATA TGC ATC AGA TTT CTC TTT CTT TTG CTC TGC ATG CTT ATT GGG AAG TCA CAT ACT
        +1    NcoI                                                                                Sph I                              30
              Glu Asp Asp Ile Ile Ile Ala Thr Lys Asn Gly Lys Val Arg Gly Met Asn Leu Thr Val Phe Gly Gly Thr Val Thr Ala Phe Leu Gly
              GAA GAT GAT ATC ATT ATT GCA ACA AAG AAT GGA AAA GTC AGA GGA ATG AAC TTG ACA GTT TTT GGT GGC ACA GTA ACA GCC TTT CTT GGA
                                                  40                                  50                              CHO               60
              Ile Pro Tyr Ala Gln Pro Pro Leu Gly Arg Leu Arg Phe Lys Pro Gln Ser Leu Thr Lys Trp Ser Asp Ile Trp Asn Ala Thr Lys
              ATT CCC TAT GCA CAG CCA CCT CTT GGT AGA CTT CGA TTC AAA AAG CCA CAG TCT CTG ACC AAG TGG TCT GAT ATT TGG AAT GCC ACA AAA  180
              Eco RI                              Acc I     Taq I
              Tyr Ala Asn Ser Cys Cys Gln Asn Ile Asp Gln Ser Phe Pro Gly Phe His Gly Ser Phe Pro Asn Thr Asp Leu Ser Glu
              TAT GCA AAT TCT TGT TGT CAG AAC ATA GAT CAA AGT TTT CCA GGC TTC CAT GGA TCA GAG ATG TGG AAC ACT GAC CTC AGT GAA  270
                                                  100                                 CHO Nco I                                 120
              Asp Cys Leu Tyr Leu Asn Val Trp Ile Pro Lys Pro Lys Asn Ala Thr Val Leu Ile Trp Ile Tyr Gly Gly Phe Gln Thr
              GAC TGT CTT TAT CTA AAT GTA TGG ATT CCA AAA CCA AAA AAT GCC ACT GTA TTG ATA TGG ATT TAT GGT GGT TTT CAA ACT  360
                                                  130                                             140                            150
              Gly Thr Ser Ser Leu His Val Tyr Asp Val Tyr Gly Lys Phe Leu Ala Arg Val Glu Arg Val Ile Val Ser Met Asn Tyr Arg Val Gly Ala
              GGA ACA TCA TCT TTA CAT GTT TAT GAT GTT TAT GGC AAG TTT CTG GCT CGG GTT GAA AGA GTT ATT GTA TCA ATG AAC TAT AGG GTG GGT GCC  450
                                                  Ava I
```

Figure 1A

```
                      160                           170                           180
Leu Gly Phe Leu Ala Leu Pro Gly Asn Met Gly Leu Phe Asp Gln Gln Leu Ala Leu Gln Trp Val Gln Lys
CTA GGA TTC TTA GCT TTG CCA GGA AAT ATG GGT CTT GAG CAG CAG TTG GCT CTT CAG TGG GTT CAA AAA  540
                      190                          200                           210
                                                    *
Asn Ile Ala Ala Phe Gly Gly Asn Pro Lys Ser Val Thr Leu phe Gly Glu SER Ala Gly Ala Ala Ser Val Ser His Leu Leu Ser
AAT ATA GCA GCC TTT GGT GGA AAT CCT AAA AGT GTA ACT CTC TTT GGA GAA AGT GCA GCT TCA GTT AGC CTG CAT CTG CTT TCT  630
                      220                          230                           240
Pro Gly Ser His Ser Leu Phe Thr Arg Ala Ile Leu Gln Ser Gly Ser Phe Asn Ala Pro Trp Ala Val Thr Ser Tyr Glu Ala Arg
CCT GGA AGC CAT TCA TTG TTC ACC AGA GCC ATT CTG CAA AGT GGT TCC TTT AAT GCT CCT TGG GCG GTA ACA TCT CTT GAA GCT AGG  720
CHO                   250                          260                           270
Asn Arg Thr Leu Asn Leu Ala Lys Leu Thr Gly Cys Ser Arg Glu Asn Glu Thr Glu Ile Ile Lys Cys Leu Arg Asn Lys Asp pro Gln
AAC AGA ACG TTG AAC TTA GCT AAA TTG ACT GGT TGC TCT AGA GAG AAT GAG ACT GAA ATA ATC AAG TGT CTT AGA AAT AAA GAT CCC CAA  810
                      280                          290                           300
                      Xba I
Glu Ile Leu Asn Glu Ala Phe Val Pro Val Tyr Gly Thr Pro Leu Ser Val Asn Phe Gly Pro Thr Val Asp Gly Asp Phe Leu Thr
GAA ATT CTT CTG AAT GAA GCA TTT GTT CCC CCC TAT GGG ACT CCT TTG TCA GTA AAC TTT GGT CCG ACC GTG GAT GGT GAT TTT CTC ACT  900
                      310                          320                           330
                                                    Ava II
Asp Met Pro Asp Ile Leu Glu Leu Asn Gly Gln Phe Lys Thr Gln Ile Leu Val Gly Val Asn Lys Asp Glu Gly Thr Trp Phe Leu
GAC ATG CCA GAC ATA CTT GAA CTT AAT GGA CAA TTT AAA ACC CAG ATT TTG GTG GGT GTT AAT AAA GAT GAA GGG ACA TGG TTT TTA  990
                                    CHO
```

```
                                        340                              350                                  360
Val Tyr Gly Ala Pro Gly Phe Ser Lys Asp Asn Asn Ser Ile Ile Thr Arg Lys Glu Gly Leu Lys Ile Phe Phe Pro Gly
GTC TAT GGT GCT CCT GGC TTC AGC AAA GAT AAT AAC AGT ATC ACT AGA AAA GAA GGT TTA AAA ATA TTT TTT CCA GGA 1080
                                        370                              380       Dra I     SspI        390

Val Ser Glu Phe Gly Lys Glu Ser Ile Leu Phe His Tyr Thr Asp Val Asp Gln Arg Pro Glu Asn Tyr Arg Glu Ala Leu Gly
GTG AGT GAG TTT GGA AAG GAA TCC ATC CTT TTT CAT TAC ACA GAC GTA GAT CAG AGA CCT GAA AAC TAC CGT GAG GCC TTG GGT 1170
                    400                              410                              420    Stu I

Asp Val Val Gly Asp Tyr Asn Phe Ile Cys Pro Ala Leu Glu Phe Thr Lys Phe Ser Glu Trp Gly Asn Ala Phe Phe Tyr Tyr
GAT GTT GTT GGG GAT TAT AAT TTC ATA TGC CCT GCC CTT GAG TTC ACC AAG TTC TCA GAA TGG GGA AAT GCC TTT TTC TAC TAT 1260
                    430                              440                              450

Phe Glu Arg Ser Ser Lys Leu Pro Trp Pro Glu Trp Met Gly Val Met His Gly Tyr Glu Ile Glu Phe Val Phe Gly Leu Pro Leu
TTT GAA CAC CGA TCC TCC AAA CTT CCG TGG CCA GAA TGG ATG GGA GTG ATG CAT GGC TAT GAA ATT GAA TTT GTC TTT GGT TTA CCT CTG 1350
                CHO     460                              470                              480

Glu Arg Asp Asn Tyr Thr Lys Ala Glu Glu Ile Leu Ser Arg Ser Ile Val Lys Tyr Arg Trp Ala Asn Phe Ala Lys Tyr Gly Asn Pro
GAA AGA GAT AAT TAC ACA AAA GCC GAG GAA ATT TTG AGT AGA TCC ATA GTG AAA TAT CGG TGG GCA AAT TTT GCA AAA TAT GGG AAT CCA 1440
CHO                 490                              500                              510

Asn Glu Thr Gln Asn Asn Ser Thr Ser Trp Pro Val Phe Lys Ser Thr Glu Gln Lys Tyr Leu Thr Leu Asn Thr Glu Ser Thr Arg Ile
AAT GAG ACT CAG AAC AAT AGC ACA ACA AGC TGG CCT GTC TTC AAA AGC ACT GAA CAA AAA TAT CTA ACC TTG AAT ACA GAG TCA ACA AGA ATA 1530
                                                                                                      Hinc II
```

```
                                                520                        530                              540
Met Thr Lys Leu Arg Ala Gln Gln Cys Arg Phe Trp Thr Ser Phe Phe Pro Lys Val Leu Glu Met Thr Gly Asn Ile Asp Glu Ala Glu
ATG ACG AAA CTA CGT GCT CAA CAA TGT CGA TTC TGG ACA TCA TTT TTT CCA AAA GTC TTG GAA ATG ACA GGA AAT ATT GAT GAA GCA GAA 1620
                                Taq I                                                                  Ssp I

Trp Glu Trp Lys Ala Gly Phe His Arg Trp Asn Asn Tyr Met Met Asp Trp Lys Asn Gln Phe Asn Asp Tyr Thr Ser Lys Glu Ser   570
TGG GAG TGG AAA GCA GGA TTC CAT CGC TGG AAC AAT TAC ATG ATG GAC TGG AAA AAT CAA TTT AAC GAT TAC ACT AGC AAG AAA GAA AGT 1710
574
Cys Val Gly Leu ***
TGT GTG GGT CTC TAA TTA ATA GAT CTC TCA TGA TCA TTG CAA TTG GAT CCA TAT ATA GGG CCC TATT CTATAGTGTCACCTAAAT
              Ase l   Bgl II              Bcl I              Bam HI, Eco01091, Apa I        Sp6 primer
```

Figure 1D

```
         10         20         30         40         50
EDDIIIATKNGKVRGMNLTVFGGTVTAFLGIPYAQPPLGRLRFKKPQSLTK
         60         70         80         90        100
WSDIWNATKYANSCCQNIDQSFPGFHGSEMWNPNTDLSEDCLYLNVWIPAP
        110        120        130        140        150
KPKNATVLIWIYGGGFQTGTSSLHVYDGKFLARVERVIVVSMNYRVGALGF
        160        170        180        190        200
LALPGNPEAPGNMGLFDQQLALQWVQKNIAAFGGNPKSVTLFGESAGAASV
        210        220        230        240        250
SLHLLSPGSHSLFTRAILQSGSFNAPWAVTSLYEARNRTLNLAKLTGCSRE
        260        270        280        290        300
NETEIIKCLRNKDPQEILLNEAFVVPYGTPLSVNFGPTVDGDFLTDMPDIL
        310        320        330        340        350
LELGQFKKTQILVGVNKDEGTAFLVYGAPGFSKDNNSIITRKEFQEGLKIF
        360        370        380        390        400
FPGVSEFGKESILFHYTDWVDDQRPENYREALGDVVGDYNFICPALEFTKK
        410        420        430        440        450
FSEWGNNAFFYYFEHRSSKLPWPEWMGVMHGYEIEFVFGLPLERRDNYTKA
        460        470        480        490        500        510
EEILSRSIVKRWANFAKYGNPNETQNNSTSWPVFKSTEQKYLTLNTESTRI
        520        530        540        550        560
MTKLRAQQCRFWTSFFPKVLEMTGNIDEAEWEWKAGFHRWNNYMMDWKNQF
        570
NDYTSKKESCVGL
```

Figure 2

```
   1 tactgaatgt cagtgcagtc caatttacag gctggagcag cagctgcatc ctgcatttcc
  61 ccgaagtatt acatgatttt cactccttgc aaactttacc atctttgttg cagagaatcg
 121 gaaatcaata tgcatagcaa agtcacaatc atatgcatca gatttctctt ttggtttctt
 181 ttgctctgca tgcttattgg gaagtcacat actgaagatg acatcataat tgcaacaaag
 241 aatggaaaag tcagagggat gaacttgaca gttttggtg gcacggtaac agcctttctt
 301 ggaattccct atgcacagcc acctcttggt agacttcgat tcaaaaagcc acagtctctg
 361 accaagtggt ctgatatttg gaatgccaca aaatatgcaa attcttgctg tcagaacata
 421 gatcaaagtt ttccaggctt ccatggatca gagatgtgga acccaaacac tgacctcagt
 481 gaagactgtt tatatctaaa tgtatggatt ccagcaccta aaccaaaaaa tgccactgta
 541 ttgatatgga tttatggtgg tggttttcaa actggaacat catctttaca tgtttatgat
 601 ggcaagtttc tggctcgggt tgaaagagtt attgtagtgt caatgaacta tagggtgggt
 661 gccctaggat tcttagcttt gccaggaaat cctgaggctc agggaacat gggtttattt
 721 gatcaacagt tggctcttca gtgggttcaa aaaaatatag cagcctttgg tggaaatcct
 781 aaaagtgtaa ctctctttgg agaaagtgca ggagcagctt cagttagcct gcatttgctt
 841 tctcctggaa gccattcatt gttcaccaga gccattctgc aaagtggatc ctttaatgct
 901 ccttgggcgg taacatctct ttatgaagct aggaacagaa cgttgaactt agctaaattg
 961 actggttgct ctagagagaa tgagactgaa ataatcaagt gtcttagaaa taaagatccc
1021 caagaaattc ttctgaatga agcatttgtt gtccctatg ggactccttt gtcagtaaac
1081 tttggtccga ccgtggatgg tgattttctc actgacatgc cagacatatt acttgaactt
1141 ggacaattta aaaaaaccca gattttggtg ggtgttaata agatgaagg gacagctttt
1201 ttagtctatg gtgctcctgg cttcagcaaa gataacaata gtatcataac tagaaaagaa
1261 tttcaggaag gttaaaaaat attttttcca ggagtgagtg agtttggaaa ggaatccatc
1321 cttttcatt acacagactg ggtagatgat cagagacctg aaaactaccg tgaggccttg
1381 ggtgatgttg ttggggatta taatttcata tgccctgcct tggagttcac caagaagttc
1441 tcagaatggg gaaataatgc cttttctac tattttgaac accgatcctc caaacttccg
1501 tggccagaat ggatgggagt gatgcatggc tatgaaattg aatttgtctt tggtttacct
1561 ctggaaagaa gagataatta cacaaaagcc gaggaaattt tgagtagatc catagtgaaa
1621 cggtgggcaa attttgcaaa atatgggaat ccaaatgaga ctcagaacaa tagcacaagc
1681 tggcctgtct tcaaaagcac tgaacaaaaa tatctaacct tgaatacaga gtcaacaaga
1741 ataatgacga aactacgtgc tcaacaatgt cgattctgga catcattttt tccaaaagtc
1801 ttggaaatga caggaaatat tgatgaagca gaatgggagt ggaaagcagg attccatcgc
1861 tggaacaatt acatgatgga ctggaaaaat caatttaacg attacactag caagaaagaa
1921 agttgtgtgg gtctctaatt aatagattta ccctttatag aacatatttt cctttagatc
1981 aaggcaaaaa tatcaggagc ttttttacac acctactaaa aaagttatta tgtagctgaa
```

Figure 3A

```
2041 acaaaaatgc cagaaggata atattgattc ctcacatctt taacttagta ttttacctag
2101 catttcaaaa cccaaatggc tagaacatgt ttaattaaat ttcacaatat aaagttctac
2161 agttaattat gtgcatatta aaacaatggc ctggttcaat ttctttcttt ccttaataaa
2221 tttaagtttt ttcccccccaa aattatcagt gctctgcttt tagtcacgtg tattttcatt
2281 accactcgta aaaaggtatc tttttttaaat gaattaaata ttgaaacact gtacaccata
2341 gtttacaata ttatgtttcc taattaaaat aagaattgaa tgtcaatatg agatattaaa
2401 ataagcacag aaaatc
```

Figure 3B

```
                                          1         10         20         30
HUMAN WILD-TYPE BChE                      EDDIIIATKN GKVRGMNLTV FGGTVTAFLG
HUMAN A VARIANT BChE                      ---------- ---------- ----------
HUMAN J VARIANT BChE                      ---------- ---------- ----------
HUMAN K VARIANT BChE                      ---------- ---------- ----------
RAT BChE                                  EEDVIITTKT GRVRGLSMPI LGGTVTAFLG
CAT BChE                                  EEDIIITTKN GKVRGMNLPV LDGTVTAFLG
HORSE BChE                                EEDIIITTKN GKVRGMNLPV LGGTVTAFLG 40         50         60         70         80         90        100
HUMAN WT    IPYAQPPLGR LRFKKPQSLT KWSDIWNATK YANSCCQNID QSFPGFHGSE MWNPNTDLSE DCLYLNVWIP
HUMAN A     ---------- ---------- ---------- --------G- ---------- ---------- ----------
HUMAN J     ---------- ---------- ---------- ---------- ---------- ---------- ----------
HUMAN K     ---------- ---------- ---------- ---------- ---------- ---------- ----------
RAT         IPYAQPPLGS LRFKKPQPLN KWPDVYNATK YANSCYQNID QAFPGFQGSE MWNPNTNLSE DCLYLNVWIP
CAT         IPYAQPPLGR LRFKKPQFLT KWSDIWNATK YANSCYQNAD QSFPGFPGSE MWNPNTDLSE DCLYLNVWIP
HORSE       IPYAQPPLGR LRFKKPQSLT KWSNIWNATK YANSCYQNTD QSFPGFLGSE MWNPNTELSE DCLYLNVWIP 110        120        130        140        150        160        170
HUMAN WT    APKPKNATVL IWIYGGGFQT GTSSLHVYDG KFLARVERVI VVSMNYRVGA LGFLALPGNP EAPGNMGLFD
HUMAN A     ---------- ---------- ---------- ---------- ---------- ---------- ----------
HUMAN J     ---------- ---------- ---------- ---------- ---------- ---------- ----------
HUMAN K     ---------- ---------- ---------- ---------- ---------- ---------- ----------
RAT         VPKPKNATVM VWVYGGGFQT GTSSLPVYDG KFLTRVERVI VVSMNYRVGA LGFLAFPGNS EAPGNMGLFD
CAT         TPKPKNATVM IWIYGGGFQT GTSSLPVYDG KFLARVERVI VVSMNYRVGA LGFLALPGNP EVPGNMGLFD
HORSE       APKPKNATVM IWIYGGGFQT GTSSLPVYDG KFLARVERVI VVSMNYRVGA LGFLALSENP EAPGNMGLFD 180        190        200        210        220        230        240
HUMAN WT    QQLALQWVQK NIAAFGGNFK SVTLFGESAG AASVSLHLLS PGSHSLFTRA ILQSGSFNAP WAVTSLYEAR
HUMAN A     ---------- ---------- ---------- ---------- ---------- ---------- ----------
HUMAN J     ---------- ---------- ---------- ---------- ---------- ---------- ----------
HUMAN K     ---------- ---------- ---------- ---------- ---------- ---------- ----------
RAT         QQLALQWIQR NIAAFGGNPK SVTLFGESAG AASVSLHLLC PQSYPLFTRA ILESGSSNAP WAVKHPEEAR
CAT         QQLALQWVQK NIAAFGGNPK SVTLFGESAG AGSVSLHLLS PRSQPLFTRA ILQSGSSNAP WAVMSLDEAK
HORSE       QQLALQWVQK NIAAFGGNPR SVTLFGESAG AASVSLHLLS PRSQPLFTRA ILQSGSSNAP WAVTSLYEAR 250        260        270        280        290        300        310
HUMAN WT    NRTLNLAKLT GCSRENETEI IKCLRNKDPQ EILLNEAFVV PYGTPLSVNF GPTVDGDFLT DMPDILLELG
HUMAN A     ---------- ---------- ---------- ---------- ---------- ---------- ----------
HUMAN J     ---------- ---------- ---------- ---------- ---------- ---------- ----------
HUMAN K     ---------- ---------- ---------- ---------- ---------- ---------- ----------
RAT         NRTLTLAKFI GCSKENEKEI ITCLRSKDPQ EILLNEKLVL PSDSIRSINF GPTVDGDFLT DMPHTLLQLG
CAT         NRTLTLAKFI GCSKENDTEI IKCLRNKDPQ EILLNELLVV PSDTLLSVNF GPVVDGDFLT DMPDTLLQLG
HORSE       NRTLTLAKRM GCSRDNETEM IKCLRDKDPQ EILLNEVFVV PYDTLLSVNF GPTVDGDFLT DMPDTLLQLG
```

Figure 4A

```
              320        330        340        350        360        370        380
HUMAN WT   QFKKTQILVG VNKDEGTAFL VYGAPGFSKD NNSIITRKEF QEGLKIFFPG VSEFGKESIL FHYTDWVDDQ
HUMAN A    ---------- ---------- ---------- ---------- ---------- ---------- ----------
HUMAN J    ---------- ---------- ---------- ---------- ---------- ---------- ----------
HUMAN K    ---------- ---------- ---------- ---------- ---------- ---------- ----------
RAT        KVKTAQILVG VNKDEGTAFL VYGAPGFSKD NDSLITRREF QEGLNMYFPG VSSLGKEAIL FYYVDWLGDQ
CAT        QFKKTQILVG VNKDEGTAFL VYGAPGFSKD NDSIITRKEF QEGLKIYFPG VSEFGREAIL FYYVDLLDDQ
HORSE      QFKRTQILVG VNKDEGTAFL VYGAPGFSKD NNSIITRKEF QEGLKIFFPR VSEFGRESIL FHYMDWLDDQ 390        400        410        420        430        440        450
HUMAN WT   RPENYREALG DVVGDYNFIC PALEFTKKFS EWGNNAFFYY FEHRSSKLPW PEWMGVMHGY EIEFVFGLPL
HUMAN A    ---------- ---------- ---------- ---------- ---------- ---------- ----------
HUMAN J    ---------- ---------- ---------- ---------- ---------- ---------- ----------
HUMAN K    ---------- ---------- ---------- ---------- ---------- ---------- ----------
RAT        TPEVYREAFD DIIGDYNIIC PALEFTKKFA ELEINAFFYY FEHRSSKLPW PEWMGVMHGY EIEFVFGLPL
CAT        RAEKYREALD DVLGDYNIIC PALEFTTKFS ELGNNAFFYY FEHRSSQLPW PEWMGVMHGY EIEFVFGLPL
HORSE      RAENYREALD DVVGDYNIIC PALEFTRKFS ELGNDAFFYY FEHRSTKLPW PEWMGVMHGY EIEFVFGLPL 460        470        480        490        500        510        520
HUMAN WT   ERRDNYTKAE EILSRSIVKR WANFAKYGNP NETQNNSTSW PVFKSTEQKY LTLNTESTRI MTKLRAQQCR
HUMAN A    ---------- ---------- ---------- ---------- ---------- ---------- ----------
HUMAN J    ---------- ---------- ---------- ---------- ---------- ---------- ----------
HUMAN K    ---------- ---------- ---------- ---------- ---------- ---------- ----------
RAT        ERRVNYTRAE EIFSRSIMKT WANFAKYGHP NGTQGNSTVW PVFTSTEQKY LTLNTEKSKI NSKLRAPQCQ
CAT        ERRVNYTRAE EILSRSIMNY WANFAKYGNP NGTQNNSTRW PAFRSTDQKY LTLNAESPKV YTKLRAQQCR
HORSE      ERRVNYTRAE EILSRSIMKR WANFAKYGNP NGTQNNSTRW PVFKSTEQKY LTLNTESPKV YTKLRAQQCR 530        540        550        560        570 574
HUMAN WT   FWTSFFPKVL EMTGNIDEAE WEWKAGFHRW NNYMMDWKNQ FNDYTSKKES CVGL
HUMAN A    ---------- ---------- ---------- ---------- ---------- ----
HUMAN J    ---------- ---------- ---------- ---------- ---------- ----
HUMAN K    ---------- ---------- ---------- ---------- ---------- ----
RAT        FWRLFFPKVL EITGDIDERE QEWKAGFHRW SNYMMDWKNQ FNDYTSKKES CTDL
CAT        FWTLFFPKVL EMTGNIDEAE REWRAGFYRW NNYMMDWKNQ FNDYTSKKES CAGL
HORSE      FWTLFFPKVL ELTGNIDEAE REWKAGFHRW NNYMMDWKNQ FNDYTSKKES CSDF
```

Figure 4B

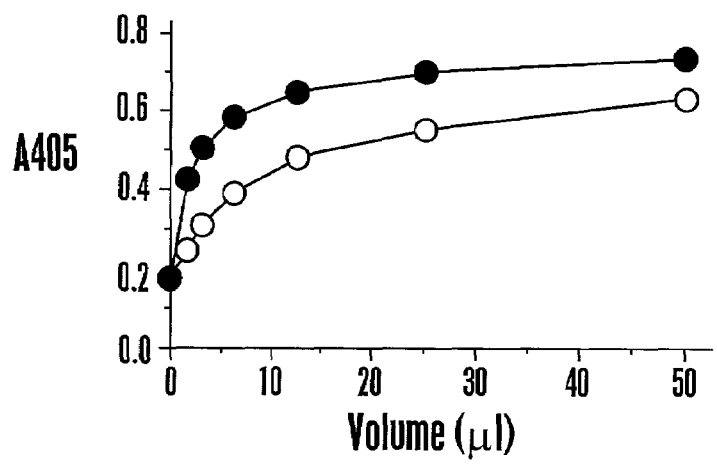
Figure 6
Figure 7
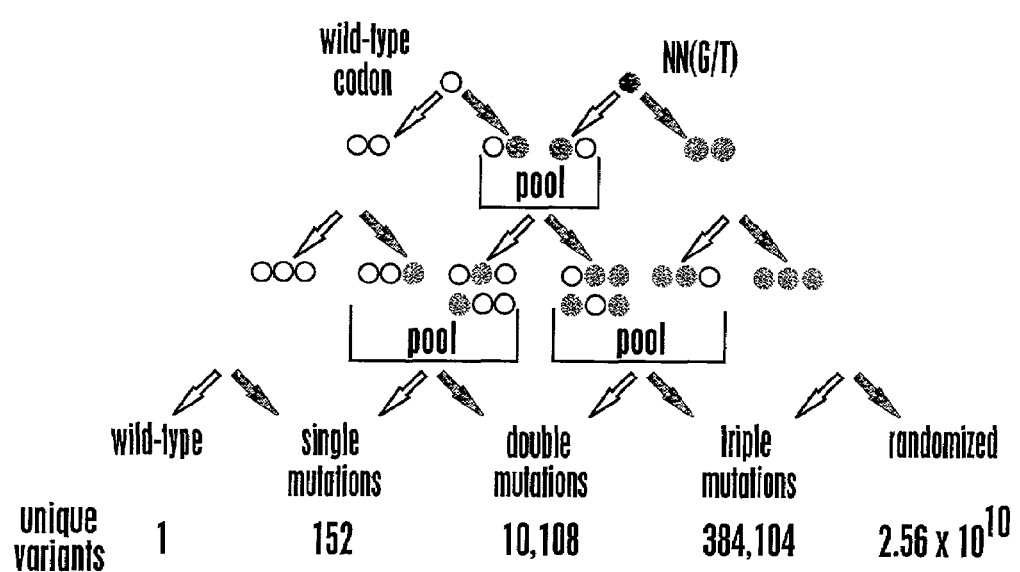

SEQUENCE LISTING

```
<160> NUMBER OF SEQ ID NOS: 24

<210> SEQ ID NO 1
<211> LENGTH: 1967
<212> TYPE: DNA
<213> ORGANISM: Artificial Sequence
<220> FEATURE:
<223> OTHER INFORMATION: Human Butyrylcholinesterase variant
<221> NAME/KEY: CDS
<222> LOCATION: (86)...(1891)

<400> SEQUENCE: 1
ttaatacgac tcactatagg gagaccggaa gcttaaggtg cacggcccac gtggatcgat      60
cgcgcgcaga tcttcggaag ccacc atg gat agc aaa gtc aca atc ata tgc       112
                            Met Asp Ser Lys Val Thr Ile Ile Cys
                             1               5
```

```
atc aga ttt ctc ttt tgg ttt ctt ttg ctc tgc atg ctt att ggg aag        160
Ile Arg Phe Leu Phe Trp Phe Leu Leu Leu Cys Met Leu Ile Gly Lys
 10              15                  20                  25 tca cat act gaa gat gac atc ata att gca aca aag aat gga aaa gtc        208
Ser His Thr Glu Asp Asp Ile Ile Ile Ala Thr Lys Asn Gly Lys Val
                 30                  35                  40 aga ggg atg aac ttg aca gtt ttt ggt ggc acg gta aca gcc ttt ctt        256
Arg Gly Met Asn Leu Thr Val Phe Gly Gly Thr Val Thr Ala Phe Leu
             45                  50                  55 gga att ccc tat gca cag cca cct ctt ggt aga ctt cga ttc aaa aag        304
Gly Ile Pro Tyr Ala Gln Pro Pro Leu Gly Arg Leu Arg Phe Lys Lys
         60                  65                  70 cca cag tct ctg acc aag tgg tct gat att tgg aat gcc aca aaa tat        352
Pro Gln Ser Leu Thr Lys Trp Ser Asp Ile Trp Asn Ala Thr Lys Tyr
 75                  80                  85 gca aat tct tgc tgt cag aac ata gat caa agt ttt cca ggc ttc cat        400
Ala Asn Ser Cys Cys Gln Asn Ile Asp Gln Ser Phe Pro Gly Phe His
 90                  95                 100                 105 gga tca gag atg tgg aac cca aac act gac ctc agt gaa gac tgt tta        448
Gly Ser Glu Met Trp Asn Pro Asn Thr Asp Leu Ser Glu Asp Cys Leu
                110                 115                 120 tat cta aat gta tgg att cca gca cct aaa cca aaa aat gcc act gta        496
Tyr Leu Asn Val Trp Ile Pro Ala Pro Lys Pro Lys Asn Ala Thr Val
            125                 130                 135 ttg ata tgg att tat ggt ggt ggt ttt caa act gga aca tca tct tta        544
Leu Ile Trp Ile Tyr Gly Gly Gly Phe Gln Thr Gly Thr Ser Ser Leu
        140                 145                 150 cat gtt tat gat ggc aag ttt ctg gct cgg gtt gaa aga gtt att gta        592
His Val Tyr Asp Gly Lys Phe Leu Ala Arg Val Glu Arg Val Ile Val
155                 160                 165 gtg tca atg aac tat agg gtg ggt gcc cta gga ttc tta gct ttg cca        640
Val Ser Met Asn Tyr Arg Val Gly Ala Leu Gly Phe Leu Ala Leu Pro
170                 175                 180                 185 gga aat cct gag gct cca ggg aac atg ggt tta ttt gat caa cag ttg        688
Gly Asn Pro Glu Ala Pro Gly Asn Met Gly Leu Phe Asp Gln Gln Leu
                190                 195                 200 gct ctt cag tgg gtt caa aaa aat ata gca gcc ttt ggt gga aat cct        736
Ala Leu Gln Trp Val Gln Lys Asn Ile Ala Ala Phe Gly Gly Asn Pro
            205                 210                 215 aaa agt gta act ctc ttt gga gaa agt gca gga gca gct tca gtt agc        784
Lys Ser Val Thr Leu Phe Gly Glu Ser Ala Gly Ala Ala Ser Val Ser
        220                 225                 230 ctg cat ttg ctt tct cct gga agc cat tca ttg ttc acc aga gcc att        832
Leu His Leu Leu Ser Pro Gly Ser His Ser Leu Phe Thr Arg Ala Ile
235                 240                 245 ctg caa agt ggt tcc ttt aat gct cct tgg gcg gta aca tct ctt tat        880
Leu Gln Ser Gly Ser Phe Asn Ala Pro Trp Ala Val Thr Ser Leu Tyr
250                 255                 260                 265 gaa gct agg aac aga acg ttg aac tta gct aaa ttg act ggt tgc tct        928
Glu Ala Arg Asn Arg Thr Leu Asn Leu Ala Lys Leu Thr Gly Cys Ser
                270                 275                 280 aga gag aat gag act gaa ata atc aag tgt ctt aga aat aaa gat ccc        976
Arg Glu Asn Glu Thr Glu Ile Ile Lys Cys Leu Arg Asn Lys Asp Pro
            285                 290                 295 caa gaa att ctt ctg aat gaa gca ttt gtt gtc ccc tat ggg act cct       1024
Gln Glu Ile Leu Leu Asn Glu Ala Phe Val Val Pro Tyr Gly Thr Pro
        300                 305                 310 ttg tca gta aac ttt ggt ccg acc gtg gat ggt gat ttt ctc act gac       1072
Leu Ser Val Asn Phe Gly Pro Thr Val Asp Gly Asp Phe Leu Thr Asp
315                 320                 325
```

-continued

```
atg cca gac ata tta ctt gaa ctt gga caa ttt aaa aaa acc cag att    1120
Met Pro Asp Ile Leu Leu Glu Leu Gly Gln Phe Lys Lys Thr Gln Ile
330                 335                 340                 345 ttg gtg ggt gtt aat aaa gat gaa ggg aca tgg ttt tta gtc tat ggt    1168
Leu Val Gly Val Asn Lys Asp Glu Gly Thr Trp Phe Leu Val Tyr Gly
            350                 355                 360 gct cct ggc ttc agc aaa gat aac aat agt atc ata act aga aaa gaa    1216
Ala Pro Gly Phe Ser Lys Asp Asn Asn Ser Ile Ile Thr Arg Lys Glu
        365                 370                 375 ttt cag gaa ggt tta aaa ata ttt ttt cca gga gtg agt gag ttt gga    1264
Phe Gln Glu Gly Leu Lys Ile Phe Phe Pro Gly Val Ser Glu Phe Gly
    380                 385                 390 aag gaa tcc atc ctt ttt cat tac aca gac tgg gta gat gat cag aga    1312
Lys Glu Ser Ile Leu Phe His Tyr Thr Asp Trp Val Asp Asp Gln Arg
395                 400                 405 cct gaa aac tac cgt gag gcc ttg ggt gat gtt gtt ggg gat tat aat    1360
Pro Glu Asn Tyr Arg Glu Ala Leu Gly Asp Val Val Gly Asp Tyr Asn
410                 415                 420                 425 ttc ata tgc cct gcc ttg gag ttc acc aag aag ttc tca gaa tgg gga    1408
Phe Ile Cys Pro Ala Leu Glu Phe Thr Lys Lys Phe Ser Glu Trp Gly
            430                 435                 440 aat aat gcc ttt ttc tac tat ttt gaa cac cga tcc tcc aaa ctt ccg    1456
Asn Asn Ala Phe Phe Tyr Tyr Phe Glu His Arg Ser Ser Lys Leu Pro
        445                 450                 455 tgg cca gaa tgg atg gga gtg atg cat ggc tat gaa att gaa ttt gtc    1504
Trp Pro Glu Trp Met Gly Val Met His Gly Tyr Glu Ile Glu Phe Val
    460                 465                 470 ttt ggt tta cct ctg gaa aga aga gat aat tac aca aaa gcc gag gaa    1552
Phe Gly Leu Pro Leu Glu Arg Arg Asp Asn Tyr Thr Lys Ala Glu Glu
475                 480                 485 att ttg agt aga tcc ata gtg aaa cgg tgg gca aat ttt gca aaa tat    1600
Ile Leu Ser Arg Ser Ile Val Lys Arg Trp Ala Asn Phe Ala Lys Tyr
490                 495                 500                 505 ggg aat cca aat gag act cag aac aat agc aca agc tgg cct gtc ttc    1648
Gly Asn Pro Asn Glu Thr Gln Asn Asn Ser Thr Ser Trp Pro Val Phe
            510                 515                 520 aaa agc act gaa caa aaa tat cta acc ttg aat aca gag tca aca aga    1696
Lys Ser Thr Glu Gln Lys Tyr Leu Thr Leu Asn Thr Glu Ser Thr Arg
        525                 530                 535 ata atg acg aaa cta cgt gct caa caa tgt cga ttc tgg aca tca ttt    1744
Ile Met Thr Lys Leu Arg Ala Gln Gln Cys Arg Phe Trp Thr Ser Phe
    540                 545                 550 ttt cca aaa gtc ttg gaa atg aca gga aat att gat gaa gca gaa tgg    1792
Phe Pro Lys Val Leu Glu Met Thr Gly Asn Ile Asp Glu Ala Glu Trp
555                 560                 565 gag tgg aaa gca gga ttc cat cgc tgg aac aat tac atg atg gac tgg    1840
Glu Trp Lys Ala Gly Phe His Arg Trp Asn Asn Tyr Met Met Asp Trp
570                 575                 580                 585 aaa aat caa ttt aac gat tac act agc aag aaa gaa agt tgt gtg ggt    1888
Lys Asn Gln Phe Asn Asp Tyr Thr Ser Lys Lys Glu Ser Cys Val Gly
            590                 595                 600 ctc taattaatag atctgtcatg atgatcattg caattggatc catatatagg         1941
Leu gccctattct atagtgtcac ctaaat                                        1967
```

<210> SEQ ID NO 2
<211> LENGTH: 602
<212> TYPE: PRT
<213> ORGANISM: Artificial Sequence -continued

```
<220> FEATURE:
<223> OTHER INFORMATION: Human Butyrylcholinesterase variant

<400> SEQUENCE: 2

Met Asp Ser Lys Val Thr Ile Ile Cys Ile Arg Phe Leu Phe Trp Phe
 1               5                  10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
                85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Trp Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
370                 375                 380

Phe Phe Pro Gly Val Ser Glu Phe Gly Lys Glu Ser Ile Leu Phe His
385                 390                 395                 400
```

```
Tyr Thr Asp Trp Val Asp Asp Gln Arg Pro Glu Asn Tyr Arg Glu Ala
            405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
                500                 505                 510

Asn Asn Ser Thr Ser Trp Pro Val Phe Lys Ser Thr Glu Gln Lys Tyr
            515                 520                 525

Leu Thr Leu Asn Thr Glu Ser Thr Arg Ile Met Thr Lys Leu Arg Ala
            530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
                580                 585                 590

Thr Ser Lys Lys Glu Ser Cys Val Gly Leu
            595                 600

<210> SEQ ID NO 3
<211> LENGTH: 2416
<212> TYPE: DNA
<213> ORGANISM: Artificial Sequence
<220> FEATURE:
<223> OTHER INFORMATION: Human Butyrylcholinesterase variant
<221> NAME/KEY: CDS
<222> LOCATION: (214)...(1935)

<400> SEQUENCE: 3
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat act gaa gat gac atc ata att gca      234
                                 Glu Asp Asp Ile Ile Ile Ala
                                  1               5 aca aag aat gga aaa gtc aga ggg atg aac ttg aca gtt ttt ggt ggc       282
Thr Lys Asn Gly Lys Val Arg Gly Met Asn Leu Thr Val Phe Gly Gly
        10                  15                  20 acg gta aca gcc ttt ctt gga att ccc tat gca cag cca cct ctt ggt       330
Thr Val Thr Ala Phe Leu Gly Ile Pro Tyr Ala Gln Pro Pro Leu Gly
    25                  30                  35 aga ctt cga ttc aaa aag cca cag tct ctg acc aag tgg tct gat att       378
Arg Leu Arg Phe Lys Lys Pro Gln Ser Leu Thr Lys Trp Ser Asp Ile
40                  45                  50                  55 tgg aat gcc aca aaa tat gca aat tct tgc tgt cag aac ata gat caa       426
Trp Asn Ala Thr Lys Tyr Ala Asn Ser Cys Cys Gln Asn Ile Asp Gln
                60                  65                  70 agt ttt cca ggc ttc cat gga tca gag atg tgg aac cca aac act gac       474
```

-continued

```
                Ser Phe Pro Gly Phe His Gly Ser Glu Met Trp Asn Pro Asn Thr Asp
                            75                  80                  85 ctc agt gaa gac tgt tta tat cta aat gta tgg att cca gca cct aaa           522
Leu Ser Glu Asp Cys Leu Tyr Leu Asn Val Trp Ile Pro Ala Pro Lys
        90                  95                 100 cca aaa aat gcc act gta ttg ata tgg att tat ggt ggt ggt ttt caa           570
Pro Lys Asn Ala Thr Val Leu Ile Trp Ile Tyr Gly Gly Gly Phe Gln
    105                 110                 115 act gga aca tca tct tta cat gtt tat gat ggc aag ttt ctg gct cgg           618
Thr Gly Thr Ser Ser Leu His Val Tyr Asp Gly Lys Phe Leu Ala Arg
120                 125                 130                 135 gtt gaa aga gtt att gta gtg tca atg aac tat agg gtg ggt gcc cta           666
Val Glu Arg Val Ile Val Val Ser Met Asn Tyr Arg Val Gly Ala Leu
                140                 145                 150 gga ttc tta gct ttg cca gga aat cct gag gct cca ggg aac atg ggt           714
Gly Phe Leu Ala Leu Pro Gly Asn Pro Glu Ala Pro Gly Asn Met Gly
            155                 160                 165 tta ttt gat caa cag ttg gct ctt cag tgg gtt caa aaa aat ata gca           762
Leu Phe Asp Gln Gln Leu Ala Leu Gln Trp Val Gln Lys Asn Ile Ala
        170                 175                 180 gcc ttt ggt gga aat cct aaa agt gta act ctc ttt gga gaa agt gca           810
Ala Phe Gly Gly Asn Pro Lys Ser Val Thr Leu Phe Gly Glu Ser Ala
    185                 190                 195 gga gca gct tca gtt agc ctg cat ttg ctt tct cct gga agc cat tca           858
Gly Ala Ala Ser Val Ser Leu His Leu Leu Ser Pro Gly Ser His Ser
200                 205                 210                 215 ttg ttc acc aga gcc att ctg caa agt gga tcc ttt aat gct cct tgg           906
Leu Phe Thr Arg Ala Ile Leu Gln Ser Gly Ser Phe Asn Ala Pro Trp
                220                 225                 230 gcg gta aca tct ctt tat gaa gct agg aac aga acg ttg aac tta gct           954
Ala Val Thr Ser Leu Tyr Glu Ala Arg Asn Arg Thr Leu Asn Leu Ala
            235                 240                 245 aaa ttg act ggt tgc tct aga gag aat gag act gaa ata atc aag tgt          1002
Lys Leu Thr Gly Cys Ser Arg Glu Asn Glu Thr Glu Ile Ile Lys Cys
        250                 255                 260 ctt aga aat aaa gat ccc caa gaa att ctt ctg aat gaa gca ttt gtt          1050
Leu Arg Asn Lys Asp Pro Gln Glu Ile Leu Leu Asn Glu Ala Phe Val
    265                 270                 275 gtc ccc tat ggg act cct ttg ggt gta aac ttt ggt ccg acc gtg gat          1098
Val Pro Tyr Gly Thr Pro Leu Gly Val Asn Phe Gly Pro Thr Val Asp
280                 285                 290                 295 ggt gat ttt ctc act gac atg cca gac ata tta ctt gaa ctt gga caa          1146
Gly Asp Phe Leu Thr Asp Met Pro Asp Ile Leu Leu Glu Leu Gly Gln
                300                 305                 310 ttt aaa aaa acc cag att ttg gtg ggt gtt aat aaa gat gaa ggg aca          1194
Phe Lys Lys Thr Gln Ile Leu Val Gly Val Asn Lys Asp Glu Gly Thr
            315                 320                 325 gct ttt tta gtc tat ggt gct cct ggc ttc agc aaa gat aac aat agt          1242
Ala Phe Leu Val Tyr Gly Ala Pro Gly Phe Ser Lys Asp Asn Asn Ser
        330                 335                 340 atc ata act aga aaa gaa ttt cag gaa ggt tta aaa ata ttt ttc cca          1290
Ile Ile Thr Arg Lys Glu Phe Gln Glu Gly Leu Lys Ile Phe Phe Pro
    345                 350                 355 gga gtg agt gag ttt gga aag gaa tcc atc ctt ttt cat tac aca gac          1338
Gly Val Ser Glu Phe Gly Lys Glu Ser Ile Leu Phe His Tyr Thr Asp
360                 365                 370                 375 tgg gta gat gat cag aga cct gaa aac tac cgt gag gcc ttg ggt gat          1386
Trp Val Asp Asp Gln Arg Pro Glu Asn Tyr Arg Glu Ala Leu Gly Asp
                380                 385                 390
```

```
gtt gtt ggg gat tat aat ttc ata tgc cct gcc ttg gag ttc acc aag      1434
Val Val Gly Asp Tyr Asn Phe Ile Cys Pro Ala Leu Glu Phe Thr Lys
            395                 400                 405 aag ttc tca gaa tgg gga aat aat gcc ttt ttc tac tat ttt gaa cac      1482
Lys Phe Ser Glu Trp Gly Asn Asn Ala Phe Phe Tyr Tyr Phe Glu His
        410                 415                 420 cga tcc tcc aaa ctt ccg tgg cca gaa tgg atg gga gtg atg cat ggc      1530
Arg Ser Ser Lys Leu Pro Trp Pro Glu Trp Met Gly Val Met His Gly
    425                 430                 435 tat gaa att gaa ttt gtc ttt ggt tta cct ctg gaa aga aga gat aat      1578
Tyr Glu Ile Glu Phe Val Phe Gly Leu Pro Leu Glu Arg Arg Asp Asn
440                 445                 450                 455 tac aca aaa gcc gag gaa att ttg agt aga tcc ata gtg aaa cgg tgg      1626
Tyr Thr Lys Ala Glu Glu Ile Leu Ser Arg Ser Ile Val Lys Arg Trp
            460                 465                 470 gca aat ttt gca aaa tat ggg aat cca aat gag act cag aac aat agc      1674
Ala Asn Phe Ala Lys Tyr Gly Asn Pro Asn Glu Thr Gln Asn Asn Ser
        475                 480                 485 aca agc tgg cct gtc ttc aaa agc act gaa caa aaa tat cta acc ttg      1722
Thr Ser Trp Pro Val Phe Lys Ser Thr Glu Gln Lys Tyr Leu Thr Leu
    490                 495                 500 aat aca gag tca aca aga ata atg acg aaa cta cgt gct caa caa tgt      1770
Asn Thr Glu Ser Thr Arg Ile Met Thr Lys Leu Arg Ala Gln Gln Cys
505                 510                 515 cga ttc tgg aca tca ttt ttt cca aaa gtc ttg gaa atg aca gga aat      1818
Arg Phe Trp Thr Ser Phe Phe Pro Lys Val Leu Glu Met Thr Gly Asn
520                 525                 530                 535 att gat gaa gca gaa tgg gag tgg aaa gca gga ttc cat cgc tgg aac      1866
Ile Asp Glu Ala Glu Trp Glu Trp Lys Ala Gly Phe His Arg Trp Asn
            540                 545                 550 aat tac atg atg gac tgg aaa aat caa ttt aac gat tac act agc aag      1914
Asn Tyr Met Met Asp Trp Lys Asn Gln Phe Asn Asp Tyr Thr Ser Lys
        555                 560                 565 aaa gaa agt tgt gtg ggt ctc taattaatag atttacccct tatagaacat         1965
Lys Glu Ser Cys Val Gly Leu
    570 attttccttt agatcaaggc aaaaatatca ggagcttttt tacacaccta ctaaaaagt     2025 tattatgtag ctgaaacaaa aatgccagaa ggataatatt gattcctcac atctttaact    2085 tagtatttta cctagcattt caaaacccaa atggctagaa catgtttaat taaatttcac    2145 aatataaagt tctacagtta attatgtgca tattaaaaca atggcctggt tcaatttctt    2205 tctttcctta ataaatttaa gttttttccc cccaaaatta tcagtgctct gcttttagtc    2265 acgtgtattt tcattaccac tcgtaaaaag gtatcttttt taaatgaatt aaatattgaa    2325 acactgtaca ccatagttta caatattatg tttcctaatt aaaataagaa ttgaatgtca    2385 atatgagata ttaaaataag cacagaaaat c                                   2416

<210> SEQ ID NO 4
<211> LENGTH: 574
<212> TYPE: PRT
<213> ORGANISM: Artificial Sequence
<220> FEATURE:
<223> OTHER INFORMATION: Human Butyrylcholinesterase variant

<400> SEQUENCE: 4

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30
```

```
Tyr Ala Gln Pro Pro Leu Gly Arg Leu Arg Phe Lys Lys Pro Gln Ser
         35                  40                  45

Leu Thr Lys Trp Ser Asp Ile Trp Asn Ala Thr Lys Tyr Ala Asn Ser
 50                  55                  60

Cys Cys Gln Asn Ile Asp Gln Ser Phe Pro Gly Phe His Gly Ser Glu
 65                  70                  75                  80

Met Trp Asn Pro Asn Thr Asp Leu Ser Glu Asp Cys Leu Tyr Leu Asn
                 85                  90                  95

Val Trp Ile Pro Ala Pro Lys Pro Lys Asn Ala Thr Val Leu Ile Trp
                100                 105                 110

Ile Tyr Gly Gly Gly Phe Gln Thr Gly Thr Ser Ser Leu His Val Tyr
                115                 120                 125

Asp Gly Lys Phe Leu Ala Arg Val Glu Arg Val Ile Val Val Ser Met
        130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
                180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
        435                 440                 445
```

```
Pro Leu Glu Arg Arg Asp Asn Tyr Thr Lys Ala Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 5
<211> LENGTH: 2416
<212> TYPE: DNA
<213> ORGANISM: Artificial Sequence
<220> FEATURE:
<223> OTHER INFORMATION: Human Butyrylcholinesterase variant
<221> NAME/KEY: CDS
<222> LOCATION: (214)...(1935)

<400> SEQUENCE: 5
tactgaatgt cagtgcagtc caatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat act gaa gat gac atc ata att gca      234
                                  Glu Asp Asp Ile Ile Ile Ala
                                   1               5 aca aag aat gga aaa gtc aga ggg atg aac ttg aca gtt ttt ggt ggc       282
Thr Lys Asn Gly Lys Val Arg Gly Met Asn Leu Thr Val Phe Gly Gly
         10                  15                  20 acg gta aca gcc ttt ctt gga att ccc tat gca cag cca cct ctt ggt       330
Thr Val Thr Ala Phe Leu Gly Ile Pro Tyr Ala Gln Pro Pro Leu Gly
     25                  30                  35 aga ctt cga ttc aaa aag cca cag tct ctg acc aag tgg tct gat att       378
Arg Leu Arg Phe Lys Lys Pro Gln Ser Leu Thr Lys Trp Ser Asp Ile
 40                  45                  50                  55 tgg aat gcc aca aaa tat gca aat tct tgc tgt cag aac ata gat caa       426
Trp Asn Ala Thr Lys Tyr Ala Asn Ser Cys Cys Gln Asn Ile Asp Gln
                 60                  65                  70 agt ttt cca ggc ttc cat gga tca gag atg tgg aac cca aac act gac       474
Ser Phe Pro Gly Phe His Gly Ser Glu Met Trp Asn Pro Asn Thr Asp
             75                  80                  85 ctc agt gaa gac tgt tta tat cta aat gta tgg att cca gca cct aaa       522
Leu Ser Glu Asp Cys Leu Tyr Leu Asn Val Trp Ile Pro Ala Pro Lys
         90                  95                 100 cca aaa aat gcc act gta ttg ata tgg att tat ggt ggt ggt ttt caa       570
Pro Lys Asn Ala Thr Val Leu Ile Trp Ile Tyr Gly Gly Gly Phe Gln
    105                 110                 115 act gga aca tca tct tta cat gtt tat gat ggc aag ttt ctg gct cgg       618
Thr Gly Thr Ser Ser Leu His Val Tyr Asp Gly Lys Phe Leu Ala Arg
120                 125                 130                 135 gtt gaa aga gtt att gta gtg tca atg aac tat agg gtg ggt gcc cta       666
```

```
                Val Glu Arg Val Ile Val Val Ser Met Asn Tyr Arg Val Gly Ala Leu
                        140                 145                 150 gga ttc tta gct ttg cca gga aat cct gag gct cca ggg aac atg ggt             714
Gly Phe Leu Ala Leu Pro Gly Asn Pro Glu Ala Pro Gly Asn Met Gly
            155                 160                 165 tta ttt gat caa cag ttg gct ctt cag tgg gtt caa aaa aat ata gca             762
Leu Phe Asp Gln Gln Leu Ala Leu Gln Trp Val Gln Lys Asn Ile Ala
            170                 175                 180 gcc ttt ggt gga aat cct aaa agt gta act ctc ttt gga gaa agt gca             810
Ala Phe Gly Gly Asn Pro Lys Ser Val Thr Leu Phe Gly Glu Ser Ala
            185                 190                 195 gga gca gct tca gtt agc ctg cat ttg ctt tct cct gga agc cat tca             858
Gly Ala Ala Ser Val Ser Leu His Leu Leu Ser Pro Gly Ser His Ser
200                 205                 210                 215 ttg ttc acc aga gcc att ctg caa agt gga tcc ttt aat gct cct tgg             906
Leu Phe Thr Arg Ala Ile Leu Gln Ser Gly Ser Phe Asn Ala Pro Trp
                220                 225                 230 gcg gta aca tct ctt tat gaa gct agg aac aga acg ttg aac tta gct             954
Ala Val Thr Ser Leu Tyr Glu Ala Arg Asn Arg Thr Leu Asn Leu Ala
                235                 240                 245 aaa ttg act ggt tgc tct aga gag aat gag act gaa ata atc aag tgt            1002
Lys Leu Thr Gly Cys Ser Arg Glu Asn Glu Thr Glu Ile Ile Lys Cys
            250                 255                 260 ctt aga aat aaa gat ccc caa gaa att ctt ctg aat gaa gca ttt gtt            1050
Leu Arg Asn Lys Asp Pro Gln Glu Ile Leu Leu Asn Glu Ala Phe Val
    265                 270                 275 gtc ccc tat ggg act cag ttg tca gta aac ttt ggt ccg acc gtg gat            1098
Val Pro Tyr Gly Thr Gln Leu Ser Val Asn Phe Gly Pro Thr Val Asp
280                 285                 290                 295 ggt gat ttt ctc act gac atg cca gac ata tta ctt gaa ctt gga caa            1146
Gly Asp Phe Leu Thr Asp Met Pro Asp Ile Leu Leu Glu Leu Gly Gln
                300                 305                 310 ttt aaa aaa acc cag att ttg gtg ggt gtt aat aaa gat gaa ggg aca            1194
Phe Lys Lys Thr Gln Ile Leu Val Gly Val Asn Lys Asp Glu Gly Thr
                315                 320                 325 gct ttt tta gtc tat ggt gct cct ggc ttc agc aaa gat aac aat agt            1242
Ala Phe Leu Val Tyr Gly Ala Pro Gly Phe Ser Lys Asp Asn Asn Ser
            330                 335                 340 atc ata act aga aaa gaa ttt cag gaa ggt tta aaa ata ttt ttt cca            1290
Ile Ile Thr Arg Lys Glu Phe Gln Glu Gly Leu Lys Ile Phe Phe Pro
            345                 350                 355 gga gtg agt gag ttt gga aag gaa tcc atc ctt ttt cat tac aca gac            1338
Gly Val Ser Glu Phe Gly Lys Glu Ser Ile Leu Phe His Tyr Thr Asp
360                 365                 370                 375 tgg gta gat gat cag aga cct gaa aac tac cgt gag gcc ttg ggt gat            1386
Trp Val Asp Asp Gln Arg Pro Glu Asn Tyr Arg Glu Ala Leu Gly Asp
                380                 385                 390 gtt gtt ggg gat tat aat ttc ata tgc cct gcc ttg gag ttc acc aag            1434
Val Val Gly Asp Tyr Asn Phe Ile Cys Pro Ala Leu Glu Phe Thr Lys
                395                 400                 405 aag ttc tca gaa tgg gga aat aat gcc ttt ttc tac tat ttt gaa cac            1482
Lys Phe Ser Glu Trp Gly Asn Asn Ala Phe Phe Tyr Tyr Phe Glu His
            410                 415                 420 cga tcc tcc aaa ctt ccg tgg cca gaa tgg atg gga gtg atg cat ggc            1530
Arg Ser Ser Lys Leu Pro Trp Pro Glu Trp Met Gly Val Met His Gly
            425                 430                 435 tat gaa att gaa ttt gtc ttt ggt tta cct ctg gaa aga aga gat aat            1578
Tyr Glu Ile Glu Phe Val Phe Gly Leu Pro Leu Glu Arg Arg Asp Asn
440                 445                 450                 455
```

-continued

| | | |
|---|---|---|
| tac aca aaa gcc gag gaa att ttg agt aga tcc ata gtg aaa cgg tgg<br>Tyr Thr Lys Ala Glu Glu Ile Leu Ser Arg Ser Ile Val Lys Arg Trp<br>                        460                       465                   470 | 1626 |
| gca aat ttt gca aaa tat ggg aat cca aat gag act cag aac aat agc<br>Ala Asn Phe Ala Lys Tyr Gly Asn Pro Asn Glu Thr Gln Asn Asn Ser<br>          475                       480                       485 | 1674 |
| aca agc tgg cct gtc ttc aaa agc act gaa caa aaa tat cta acc ttg<br>Thr Ser Trp Pro Val Phe Lys Ser Thr Glu Gln Lys Tyr Leu Thr Leu<br>               490                      495                   500 | 1722 |
| aat aca gag tca aca aga ata atg acg aaa cta cgt gct caa caa tgt<br>Asn Thr Glu Ser Thr Arg Ile Met Thr Lys Leu Arg Ala Gln Gln Cys<br>       505                       510                      515 | 1770 |
| cga ttc tgg aca tca ttt ttt cca aaa gtc ttg gaa atg aca gga aat<br>Arg Phe Trp Thr Ser Phe Phe Pro Lys Val Leu Glu Met Thr Gly Asn<br>520                       525                     530                   535 | 1818 |
| att gat gaa gca gaa tgg gag tgg aaa gca gga ttc cat cgc tgg aac<br>Ile Asp Glu Ala Glu Trp Glu Trp Lys Ala Gly Phe His Arg Trp Asn<br>               540                      545                   550 | 1866 |
| aat tac atg atg gac tgg aaa aat caa ttt aac gat tac act agc aag<br>Asn Tyr Met Met Asp Trp Lys Asn Gln Phe Asn Asp Tyr Thr Ser Lys<br>       555                       560                      565 | 1914 |
| aaa gaa agt tgt gtg ggt ctc taattaatag atttaccctt tatagaacat<br>Lys Glu Ser Cys Val Gly Leu<br>          570 | 1965 |
| attttccttt agatcaaggc aaaaatatca ggagctttt tacacaccta ctaaaaagt | 2025 |
| tattatgtag ctgaaacaaa aatgccagaa ggataatatt gattcctcac atctttaact | 2085 |
| tagtatttta cctagcattt caaaacccaa atggctagaa catgtttaat taaatttcac | 2145 |
| aatataaagt tctacagtta attatgtgca tattaaaaca atggcctggt tcaatttctt | 2205 |
| tcttttccta ataaatttaa gttttttccc cccaaaatta tcagtgctct gcttttagtc | 2265 |
| acgtgtattt tcattaccac tcgtaaaaag gtatcttttt taaatgaatt aaatattgaa | 2325 |
| acactgtaca ccatagttta caatattatg tttcctaatt aaaataagaa ttgaatgtca | 2385 |
| atatgagata ttaaaataag cacagaaaat c | 2416 |

<210> SEQ ID NO 6
<211> LENGTH: 574
<212> TYPE: PRT
<213> ORGANISM: Artificial Sequence
<220> FEATURE:
<223> OTHER INFORMATION: Human Butyrylcholinesterase variant

<400> SEQUENCE: 6

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

```
Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Gln Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
```

```
                     530                 535                 540
Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 7
<211> LENGTH: 2416
<212> TYPE: DNA
<213> ORGANISM: Artificial Sequence
<220> FEATURE:
<223> OTHER INFORMATION: Human Butyrylcholinesterase variant
<221> NAME/KEY: CDS
<222> LOCATION: (214)...(1935)

<400> SEQUENCE: 7
tactgaatgt cagtgcagtc aatttacag gctggagcag cagctgcatc ctgcatttcc      60
ccgaagtatt acatgatttt cactccttgc aaactttacc atctttgttg cagagaatcg     120
gaaatcaata tgcatagcaa agtcacaatc atatgcatca gatttctctt ttggtttctt     180
ttgctctgca tgcttattgg gaagtcacat act gaa gat gac atc ata att gca     234
                                    Glu Asp Asp Ile Ile Ile Ala
                                      1               5 aca aag aat gga aaa gtc aga ggg atg aac ttg aca gtt ttt ggt ggc      282
Thr Lys Asn Gly Lys Val Arg Gly Met Asn Leu Thr Val Phe Gly Gly
         10                  15                  20 acg gta aca gcc ttt ctt gga att ccc tat gca cag cca cct ctt ggt      330
Thr Val Thr Ala Phe Leu Gly Ile Pro Tyr Ala Gln Pro Pro Leu Gly
     25                  30                  35 aga ctt cga ttc aaa aag cca cag tct ctg acc aag tgg tct gat att      378
Arg Leu Arg Phe Lys Lys Pro Gln Ser Leu Thr Lys Trp Ser Asp Ile
 40                  45                  50                  55 tgg aat gcc aca aaa tat gca aat tct tgc tgt cag aac ata gat caa      426
Trp Asn Ala Thr Lys Tyr Ala Asn Ser Cys Cys Gln Asn Ile Asp Gln
                 60                  65                  70 agt ttt cca ggc ttc cat gga tca gag atg tgg aac cca aac act gac      474
Ser Phe Pro Gly Phe His Gly Ser Glu Met Trp Asn Pro Asn Thr Asp
             75                  80                  85 ctc agt gaa gac tgt tta tat cta aat gta tgg att cca gca cct aaa      522
Leu Ser Glu Asp Cys Leu Tyr Leu Asn Val Trp Ile Pro Ala Pro Lys
         90                  95                 100 cca aaa aat gcc act gta ttg ata tgg att tat ggt ggt ggt ttt caa      570
Pro Lys Asn Ala Thr Val Leu Ile Trp Ile Tyr Gly Gly Gly Phe Gln
     105                 110                 115 act gga aca tca tct tta cat gtt tat gat ggc aag ttt ctg gct cgg      618
Thr Gly Thr Ser Ser Leu His Val Tyr Asp Gly Lys Phe Leu Ala Arg
120                 125                 130                 135 gtt gaa aga gtt att gta gtg tca atg aac tat agg gtg ggt gcc cta      666
Val Glu Arg Val Ile Val Val Ser Met Asn Tyr Arg Val Gly Ala Leu
                 140                 145                 150 gga ttc tta gct ttg cca gga aat cct gag gct cca ggg aac atg ggt      714
Gly Phe Leu Ala Leu Pro Gly Asn Pro Glu Ala Pro Gly Asn Met Gly
             155                 160                 165 tta ttt gat caa cag ttg gct ctt cag tgg gtt caa aaa aat ata gca      762
Leu Phe Asp Gln Gln Leu Ala Leu Gln Trp Val Gln Lys Asn Ile Ala
         170                 175                 180 gcc ttt ggt gga aat cct aaa agt gta act ctc ttt gga gaa agt gca      810
Ala Phe Gly Gly Asn Pro Lys Ser Val Thr Leu Phe Gly Glu Ser Ala
     185                 190                 195 gga gca gct tca gtt agc ctg cat ttg ctt tct cct gga agc cat tca      858
```

| | | | | | | | | | | | | |
|---|---|---|---|---|---|---|---|---|---|---|---|---|
| Gly | Ala | Ala | Ser | Val | Ser | Leu | His | Leu | Leu | Ser | Pro | Gly | Ser | His | Ser |
| | 200 | | | | 205 | | | | 210 | | | | 215 | | |

| ttg | ttc | acc | aga | gcc | att | ctg | caa | agt | gga | tcc | ttt | aat | gct | cct | tgg | 906 |
|---|---|---|---|---|---|---|---|---|---|---|---|---|---|---|---|---|
| Leu | Phe | Thr | Arg | Ala | Ile | Leu | Gln | Ser | Gly | Ser | Phe | Asn | Ala | Pro | Trp | |
| | | | | 220 | | | | | 225 | | | | | 230 | | |

| gcg | gta | aca | tct | ctt | tat | gaa | gct | agg | aac | aga | acg | ttg | aac | tta | gct | 954 |
|---|---|---|---|---|---|---|---|---|---|---|---|---|---|---|---|---|
| Ala | Val | Thr | Ser | Leu | Tyr | Glu | Ala | Arg | Asn | Arg | Thr | Leu | Asn | Leu | Ala | |
| | | | 235 | | | | | 240 | | | | | 245 | | | |

| aaa | ttg | act | ggt | tgc | tct | aga | gag | aat | gag | act | gaa | ata | atc | aag | tgt | 1002 |
|---|---|---|---|---|---|---|---|---|---|---|---|---|---|---|---|---|
| Lys | Leu | Thr | Gly | Cys | Ser | Arg | Glu | Asn | Glu | Thr | Glu | Ile | Ile | Lys | Cys | |
| | | | 250 | | | | | 255 | | | | | 260 | | | |

| ctt | aga | aat | aaa | gat | ccc | caa | gaa | att | ctt | ctg | aat | gaa | gca | ttt | gtt | 1050 |
|---|---|---|---|---|---|---|---|---|---|---|---|---|---|---|---|---|
| Leu | Arg | Asn | Lys | Asp | Pro | Gln | Glu | Ile | Leu | Leu | Asn | Glu | Ala | Phe | Val | |
| | 265 | | | | 270 | | | | 275 | | | | | | | |

| gtc | ccc | tat | ggg | act | tcg | ttg | tca | gta | aac | ttt | ggt | ccg | acc | gtg | gat | 1098 |
|---|---|---|---|---|---|---|---|---|---|---|---|---|---|---|---|---|
| Val | Pro | Tyr | Gly | Thr | Ser | Leu | Ser | Val | Asn | Phe | Gly | Pro | Thr | Val | Asp | |
| 280 | | | | | 285 | | | | | 290 | | | | | 295 | |

| ggt | gat | ttt | ctc | act | gac | atg | cca | gac | ata | tta | ctt | gaa | ctt | gga | caa | 1146 |
|---|---|---|---|---|---|---|---|---|---|---|---|---|---|---|---|---|
| Gly | Asp | Phe | Leu | Thr | Asp | Met | Pro | Asp | Ile | Leu | Leu | Glu | Leu | Gly | Gln | |
| | | | | 300 | | | | | 305 | | | | | 310 | | |

| ttt | aaa | aaa | acc | cag | att | ttg | gtg | ggt | gtt | aat | aaa | gat | gaa | ggg | aca | 1194 |
|---|---|---|---|---|---|---|---|---|---|---|---|---|---|---|---|---|
| Phe | Lys | Lys | Thr | Gln | Ile | Leu | Val | Gly | Val | Asn | Lys | Asp | Glu | Gly | Thr | |
| | | | 315 | | | | | 320 | | | | | 325 | | | |

| gct | ttt | tta | gtc | tat | ggt | gct | cct | ggc | ttc | agc | aaa | gat | aac | aat | agt | 1242 |
|---|---|---|---|---|---|---|---|---|---|---|---|---|---|---|---|---|
| Ala | Phe | Leu | Val | Tyr | Gly | Ala | Pro | Gly | Phe | Ser | Lys | Asp | Asn | Asn | Ser | |
| | | | 330 | | | | | 335 | | | | | 340 | | | |

| atc | ata | act | aga | aaa | gaa | ttt | cag | gaa | ggt | tta | aaa | ata | ttt | ttt | cca | 1290 |
|---|---|---|---|---|---|---|---|---|---|---|---|---|---|---|---|---|
| Ile | Ile | Thr | Arg | Lys | Glu | Phe | Gln | Glu | Gly | Leu | Lys | Ile | Phe | Phe | Pro | |
| 345 | | | | | 350 | | | | | 355 | | | | | | |

| gga | gtg | agt | gag | ttt | gga | aag | gaa | tcc | atc | ctt | ttt | cat | tac | aca | gac | 1338 |
|---|---|---|---|---|---|---|---|---|---|---|---|---|---|---|---|---|
| Gly | Val | Ser | Glu | Phe | Gly | Lys | Glu | Ser | Ile | Leu | Phe | His | Tyr | Thr | Asp | |
| 360 | | | | | 365 | | | | | 370 | | | | | 375 | |

| tgg | gta | gat | gat | cag | aga | cct | gaa | aac | tac | cgt | gag | gcc | ttg | ggt | gat | 1386 |
|---|---|---|---|---|---|---|---|---|---|---|---|---|---|---|---|---|
| Trp | Val | Asp | Asp | Gln | Arg | Pro | Glu | Asn | Tyr | Arg | Glu | Ala | Leu | Gly | Asp | |
| | | | | 380 | | | | | 385 | | | | | 390 | | |

| gtt | gtt | ggg | gat | tat | aat | ttc | ata | tgc | cct | gcc | ttg | gag | ttc | acc | aag | 1434 |
|---|---|---|---|---|---|---|---|---|---|---|---|---|---|---|---|---|
| Val | Val | Gly | Asp | Tyr | Asn | Phe | Ile | Cys | Pro | Ala | Leu | Glu | Phe | Thr | Lys | |
| | | | 395 | | | | | 400 | | | | | 405 | | | |

| aag | ttc | tca | gaa | tgg | gga | aat | aat | gcc | ttt | ttc | tac | tat | ttt | gaa | cac | 1482 |
|---|---|---|---|---|---|---|---|---|---|---|---|---|---|---|---|---|
| Lys | Phe | Ser | Glu | Trp | Gly | Asn | Asn | Ala | Phe | Phe | Tyr | Tyr | Phe | Glu | His | |
| | | | 410 | | | | | 415 | | | | | 420 | | | |

| cga | tcc | tcc | aaa | ctt | ccg | tgg | cca | gaa | tgg | atg | gga | gtg | atg | cat | ggc | 1530 |
|---|---|---|---|---|---|---|---|---|---|---|---|---|---|---|---|---|
| Arg | Ser | Ser | Lys | Leu | Pro | Trp | Pro | Glu | Trp | Met | Gly | Val | Met | His | Gly | |
| | 425 | | | | | 430 | | | | | 435 | | | | | |

| tat | gaa | att | gaa | ttt | gtc | ttt | ggt | tta | cct | ctg | gaa | aga | aga | gat | aat | 1578 |
|---|---|---|---|---|---|---|---|---|---|---|---|---|---|---|---|---|
| Tyr | Glu | Ile | Glu | Phe | Val | Phe | Gly | Leu | Pro | Leu | Glu | Arg | Arg | Asp | Asn | |
| 440 | | | | | 445 | | | | | 450 | | | | | 455 | |

| tac | aca | aaa | gcc | gag | gaa | att | ttg | agt | aga | tcc | ata | gtg | aaa | cgg | tgg | 1626 |
|---|---|---|---|---|---|---|---|---|---|---|---|---|---|---|---|---|
| Tyr | Thr | Lys | Ala | Glu | Glu | Ile | Leu | Ser | Arg | Ser | Ile | Val | Lys | Arg | Trp | |
| | | | | 460 | | | | | 465 | | | | | 470 | | |

| gca | aat | ttt | gca | aaa | tat | ggg | aat | cca | aat | gag | act | cag | aac | aat | agc | 1674 |
|---|---|---|---|---|---|---|---|---|---|---|---|---|---|---|---|---|
| Ala | Asn | Phe | Ala | Lys | Tyr | Gly | Asn | Pro | Asn | Glu | Thr | Gln | Asn | Asn | Ser | |
| | | | 475 | | | | | 480 | | | | | 485 | | | |

| aca | agc | tgg | cct | gtc | ttc | aaa | agc | act | gaa | caa | aaa | tat | cta | acc | ttg | 1722 |
|---|---|---|---|---|---|---|---|---|---|---|---|---|---|---|---|---|
| Thr | Ser | Trp | Pro | Val | Phe | Lys | Ser | Thr | Glu | Gln | Lys | Tyr | Leu | Thr | Leu | |
| | | 490 | | | | | 495 | | | | | 500 | | | | |

| aat | aca | gag | tca | aca | aga | ata | atg | acg | aaa | cta | cgt | gct | caa | caa | tgt | 1770 |
|---|---|---|---|---|---|---|---|---|---|---|---|---|---|---|---|---|
| Asn | Thr | Glu | Ser | Thr | Arg | Ile | Met | Thr | Lys | Leu | Arg | Ala | Gln | Gln | Cys | |
| | 505 | | | | | 510 | | | | | 515 | | | | | |

-continued

```
cga ttc tgg aca tca ttt ttt cca aaa gtc ttg gaa atg aca gga aat    1818
Arg Phe Trp Thr Ser Phe Phe Pro Lys Val Leu Glu Met Thr Gly Asn
520                 525                 530                 535 att gat gaa gca gaa tgg gag tgg aaa gca gga ttc cat cgc tgg aac    1866
Ile Asp Glu Ala Glu Trp Glu Trp Lys Ala Gly Phe His Arg Trp Asn
                540                 545                 550 aat tac atg atg gac tgg aaa aat caa ttt aac gat tac act agc aag    1914
Asn Tyr Met Met Asp Trp Lys Asn Gln Phe Asn Asp Tyr Thr Ser Lys
            555                 560                 565 aaa gaa agt tgt gtg ggt ctc taattaatag atttaccctt tatagaacat       1965
Lys Glu Ser Cys Val Gly Leu
        570 attttccttt agatcaaggc aaaaatatca ggagctttt tacacaccta ctaaaaagt    2025 tattatgtag ctgaaacaaa aatgccagaa ggataatatt gattcctcac atctttaact  2085 tagtatttta cctagcattt caaaacccaa atggctagaa catgtttaat taaatttcac  2145 aatataaagt tctacagtta attatgtgca tattaaaaca atggcctggt tcaatttctt  2205 tctttcctta ataaatttaa gttttttccc cccaaaatta tcagtgctct gcttttagtc  2265 acgtgtattt tcattaccac tcgtaaaaag gtatcttttt taaatgaatt aaatattgaa  2325 acactgtaca ccatagttta caatattatg tttcctaatt aaaataagaa ttgaatgtca  2385 atatgagata ttaaaataag cacagaaaat c                                 2416
```

<210> SEQ ID NO 8
<211> LENGTH: 574
<212> TYPE: PRT
<213> ORGANISM: Artificial Sequence
<220> FEATURE:
<223> OTHER INFORMATION: Human Butyrylcholinesterase variant

<400> SEQUENCE: 8

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
```

```
                195                 200                 205
Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Ser Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 9
<211> LENGTH: 15
<212> TYPE: PRT
<213> ORGANISM: Artificial Sequence
<220> FEATURE:
<223> OTHER INFORMATION: Human Butyrylcholinesterase variant
```

```
<400> SEQUENCE: 9

Asn Ile Asp Gln Ser Phe Pro Gly Phe His Gly Ser Glu Met Trp
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Human Butyrylcholinesterase variant

<400> SEQUENCE: 10

Leu Ile Trp Ile Tyr Gly Gly Gly Phe Gln Thr Gly
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Human Butyrylcholinesterase variant

<400> SEQUENCE: 11

Leu Phe Gly Glu Ser Ala Gly Ala
1               5

<210> SEQ ID NO 12
<211> LENGTH: 11
<212> TYPE: PRT
<213> ORGANISM: Artificial Sequence
<220> FEATURE:
<223> OTHER INFORMATION: Human Butyrylcholinesterase variant

<400> SEQUENCE: 12

Ser Gly Ser Phe Asn Ala Pro Trp Ala Val Thr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Human Butyrylcholinesterase variant

<400> SEQUENCE: 13

Ala Phe Val Val Pro Tyr Gly Thr Pro Leu Ser Val Asn
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Human Butyrylcholinesterase variant

<400> SEQUENCE: 14

Thr Ala Phe Leu Val Tyr
1               5

<210> SEQ ID NO 15
<211> LENGTH: 14
<212> TYPE: PRT
<213> ORGANISM: Artificial Sequence
<220> FEATURE:
<223> OTHER INFORMATION: Human Butyrylcholinesterase variant

<400> SEQUENCE: 15
```

```
Pro Trp Pro Glu Trp Met Gly Val Met His Gly Tyr Glu Ile
 1               5                   10
```

<210> SEQ ID NO 16
<211> LENGTH: 2416
<212> TYPE: DNA
<213> ORGANISM: Homo sapiens

<400> SEQUENCE: 16

| | | | | | |
|---|---|---|---|---|---|
| tactgaatgt | cagtgcagtc | caatttacag | gctggagcag | cagctgcatc | ctgcatttcc | 60 |
| ccgaagtatt | acatgatttt | cactccttgc | aaactttacc | atctttgttg | cagagaatcg | 120 |
| gaaatcaata | tgcatagcaa | agtcacaatc | atatgcatca | gatttctctt | ttggtttctt | 180 |
| ttgctctgca | tgcttattgg | gaagtcacat | actgaagatg | acatcataat | tgcaacaaag | 240 |
| aatggaaaag | tcagagggat | gaacttgaca | gttttggtg | gcacggtaac | agcctttctt | 300 |
| ggaattccct | atgcacagcc | acctcttggt | agacttcgat | tcaaaaagcc | acagtctctg | 360 |
| accaagtggt | ctgatatttg | gaatgccaca | aaatatgcaa | attcttgctg | tcagaacata | 420 |
| gatcaaagtt | ttccaggctt | ccatggatca | gagatgtgga | acccaaacac | tgacctcagt | 480 |
| gaagactgtt | tatatctaaa | tgtatggatt | ccagcaccta | accaaaaaaa | tgccactgta | 540 |
| ttgatatgga | tttatggtgg | tggttttcaa | actggaacat | catctttaca | tgtttatgat | 600 |
| ggcaagtttc | tggctcgggt | tgaaagagtt | attgtagtgt | caatgaacta | tagggtgggt | 660 |
| gccctaggat | tcttagcttt | gccaggaaat | cctgaggctc | cagggaacat | gggtttattt | 720 |
| gatcaacagt | tggctcttca | gtgggttcaa | aaaaatatag | cagcctttgg | tggaaatcct | 780 |
| aaaagtgtaa | ctctctttgg | agaaagtgca | ggagcagctt | cagttagcct | gcatttgctt | 840 |
| tctcctggaa | gccattcatt | gttcaccaga | gccattctgc | aaagtggatc | ctttaatgct | 900 |
| ccttgggcgg | taacatctct | ttatgaagct | aggaacagaa | cgttaactt | agctaaattg | 960 |
| actggttgct | ctagagagaa | tgagactgaa | ataatcaagt | gtcttagaaa | taaagatccc | 1020 |
| caagaaattc | ttctgaatga | agcatttgtt | gtccccctatg | ggactccttt | gtcagtaaac | 1080 |
| tttggtccga | ccgtggatgg | tgattttctc | actgacatgc | cagacatatt | acttgaactt | 1140 |
| ggacaattta | aaaaaaccca | gattttggtg | ggtgttaata | aagatgaagg | gacagctttt | 1200 |
| ttagtctatg | gtgctcctgg | cttcagcaaa | gataacaata | gtatcataac | tagaaaagaa | 1260 |
| tttcaggaag | gtttaaaaat | atttttccca | ggagtgagtg | agtttggaaa | ggaatccatc | 1320 |
| ctttttcatt | acacagactg | ggtagatgat | cagagacctg | aaaactaccg | tgaggccttg | 1380 |
| ggtgatgttg | ttgggggatta | taatttcata | tgccctgcct | tggagttcac | caagaagttc | 1440 |
| tcagaatggg | gaaataatgc | cttttttctac | tattttgaac | accgatcctc | caaacttccg | 1500 |
| tggccagaat | ggatgggagt | gatgcatggc | tatgaaattg | aatttgtctt | tggtttacct | 1560 |
| ctggaaagaa | gagataatta | cacaaaagcc | gaggaaattt | tgagtagatc | catagtgaaa | 1620 |
| cggtgggcaa | attttgcaaa | atatgggaat | ccaaatgaga | ctcagaacaa | tagcacaagc | 1680 |
| tggcctgtct | tcaaaagcac | tgaacaaaaa | tatctaacct | tgaatacaga | gtcaacaaga | 1740 |
| ataatgacga | aactacgtgc | tcaacaatgt | cgattctgga | catcattttt | tccaaaagtc | 1800 |
| ttggaaatga | caggaaatat | tgatgaagca | gaatgggagt | ggaaagcagg | attccatcgc | 1860 |
| tggaacaatt | acatgatgga | ctggaaaaat | caatttaacg | attacactag | caagaaagaa | 1920 |
| agttgtgtgg | gtctctaatt | aatagattta | ccctttatag | aacatatttt | cctttagatc | 1980 |
| aaggcaaaaa | tatcaggagc | ttttttacac | acctactaaa | aaagttatta | tgtagctgaa | 2040 |

```
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttcccccaa aattatcagt gctctgcttt tagtcacgtg tatttcatt      2280 accactcgta aaaggtatc tttttaaat gaattaaata ttgaaacact gtacaccata      2340
gtttacaata ttatgtttcc taattaaaat aagaattgaa tgtcaatatg agatattaaa    2400
ataagcacag aaaatc                                                    2416
```

```
<210> SEQ ID NO 17
<211> LENGTH: 574
<212> TYPE: PRT
<213> ORGANISM: Homo sapiens

<400> SEQUENCE: 17

Glu Asp Asp Ile Ile Ala Thr Lys Asn Gly Lys Val Arg Gly Met
 1               5                  10                  15

Asn Leu Thr Val Phe Gly Gly Thr Val Thr Ala Phe Leu Gly Ile Pro
                20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
        50                  55                  60

Cys Cys Gln Asn Ile Asp Gln Ser Phe Pro Gly Phe His Gly Ser Glu
 65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300
```

```
Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Lys Glu Ser
        355                 360                 365

Ile Leu Phe His Tyr Thr Asp Trp Val Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 18
<211> LENGTH: 574
<212> TYPE: PRT
<213> ORGANISM: Homo sapiens

<400> SEQUENCE: 18

Glu Asp Asp Ile Ile Ala Thr Lys Asn Gly Lys Val Arg Gly Met
 1               5                  10                  15

Asn Leu Thr Val Phe Gly Gly Thr Val Thr Ala Phe Leu Gly Ile Pro
                20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
        50                  55                  60

Cys Cys Gln Asn Ile Gly Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
```

-continued

```
                100                 105                 110
Ile Tyr Gly Gly Phe Gln Thr Gly Thr Ser Ser Leu His Val Tyr
            115                 120                 125
Asp Gly Lys Phe Leu Ala Arg Val Glu Arg Val Ile Val Val Ser Met
    130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
                180                 185                 190
Thr Leu Phe Gly Glu Ser Ala Gly Ala Ala Ser Val Ser Leu His Leu
                195                 200                 205
Leu Ser Pro Gly Ser His Ser Leu Phe Thr Arg Ala Ile Leu Gln Ser
            210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Pro Leu Ser Val
            275                 280                 285
Asn Phe Gly Pro Thr Val Asp Gly Asp Phe Leu Thr Asp Met Pro Asp
            290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
                435                 440                 445
Pro Leu Glu Arg Arg Asp Asn Tyr Thr Lys Ala Glu Glu Ile Leu Ser
            450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
            515                 520                 525
```

```
Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 19
<211> LENGTH: 574
<212> TYPE: PRT
<213> ORGANISM: Homo sapiens

<400> SEQUENCE: 19

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
                20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
    115                 120                 125

Asp Gly Lys Phe Leu Ala Arg Val Glu Arg Val Ile Val Val Ser Met
130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
    195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
    275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
```

```
                    325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
        370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Ile Leu Ser
        450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Val Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
        530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

```
<210> SEQ ID NO 20
<211> LENGTH: 574
<212> TYPE: PRT
<213> ORGANISM: Homo sapiens

<400> SEQUENCE: 20

Glu Asp Asp Ile Ile Ile Ala Thr Lys Asn Gly Lys Val Arg Gly Met
 1               5                  10                  15
Asn Leu Thr Val Phe Gly Gly Thr Val Thr Ala Phe Leu Gly Ile Pro
                20                  25                  30
Tyr Ala Gln Pro Pro Leu Gly Arg Leu Arg Phe Lys Lys Pro Gln Ser
            35                  40                  45
Leu Thr Lys Trp Ser Asp Ile Trp Asn Ala Thr Lys Tyr Ala Asn Ser
        50                  55                  60
Cys Cys Gln Asn Ile Asp Gln Ser Phe Pro Gly Phe His Gly Ser Glu
65                  70                  75                  80
Met Trp Asn Pro Asn Thr Asp Leu Ser Glu Asp Cys Leu Tyr Leu Asn
                85                  90                  95
Val Trp Ile Pro Ala Pro Lys Pro Lys Asn Ala Thr Val Leu Ile Trp
                100                 105                 110
Ile Tyr Gly Gly Gly Phe Gln Thr Gly Thr Ser Ser Leu His Val Tyr
            115                 120                 125
```

```
Asp Gly Lys Phe Leu Ala Arg Val Glu Arg Val Ile Val Val Ser Met
        130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
        180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
                355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
        450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Thr Glu Trp Glu Trp Lys
530                 535                 540

Ala Gly Phe His Arg Trp Asn Asn Tyr Met Met Asp Trp Lys Asn Gln
```

```
                545                 550                 555                 560
Phe Asn Asp Tyr Thr Ser Lys Lys Glu Ser Cys Val Gly Leu
                    565                 570

<210> SEQ ID NO 21
<211> LENGTH: 574
<212> TYPE: PRT
<213> ORGANISM: Equus caballus

<400> SEQUENCE: 21

Glu Glu Asp Ile Ile Ile Thr Thr Lys Asn Gly Lys Val Arg Gly Met
 1               5                  10                  15

Asn Leu Pro Val Leu Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asn Ile Trp Asn Ala Thr Lys Tyr Ala Asn Ser
50                  55                  60

Cys Tyr Gln Asn Thr Asp Gln Ser Phe Pro Gly Phe Leu Gly Ser Glu
65                  70                  75                  80

Met Trp Asn Pro Asn Thr Glu Leu Ser Glu Asp Cys Leu Tyr Leu Asn
                85                  90                  95

Val Trp Ile Pro Ala Pro Lys Pro Lys Asn Ala Thr Val Met Ile Trp
            100                 105                 110

Ile Tyr Gly Gly Gly Phe Gln Thr Gly Thr Ser Ser Leu Pro Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Ser Glu Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Arg Ser Val
            180                 185                 190

Thr Leu Phe Gly Glu Ser Ala Gly Ala Ala Ser Val Ser Leu His Leu
        195                 200                 205

Leu Ser Pro Arg Ser Gln Pro Leu Phe Thr Arg Ala Ile Leu Gln Ser
    210                 215                 220

Gly Ser Ser Asn Ala Pro Trp Ala Val Thr Ser Leu Tyr Glu Ala Arg
225                 230                 235                 240

Asn Arg Thr Leu Thr Leu Ala Lys Arg Met Gly Cys Ser Arg Asp Asn
                245                 250                 255

Glu Thr Glu Met Ile Lys Cys Leu Arg Asp Lys Asp Pro Gln Glu Ile
            260                 265                 270

Leu Leu Asn Glu Val Phe Val Val Pro Tyr Asp Thr Leu Leu Ser Val
        275                 280                 285

Asn Phe Gly Pro Thr Val Asp Gly Asp Phe Leu Thr Asp Met Pro Asp
    290                 295                 300

Thr Leu Leu Gln Leu Gly Gln Phe Lys Arg Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350
```

```
Gly Leu Lys Ile Phe Phe Pro Arg Val Ser Glu Phe Gly Arg Glu Ser
            355                 360                 365

Ile Leu Phe His Tyr Met Asp Trp Leu Asp Asp Gln Arg Ala Glu Asn
        370                 375                 380

Tyr Arg Glu Ala Leu Asp Asp Val Val Gly Asp Tyr Asn Ile Ile Cys
385                 390                 395                 400

Pro Ala Leu Glu Phe Thr Arg Lys Phe Ser Glu Leu Gly Asn Asp Ala
                405                 410                 415

Phe Phe Tyr Tyr Phe Glu His Arg Ser Thr Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Val Asn Tyr Thr Arg Ala Glu Glu Ile Leu Ser
        450                 455                 460

Arg Ser Ile Met Lys Arg Trp Ala Asn Phe Ala Lys Tyr Gly Asn Pro
465                 470                 475                 480

Asn Gly Thr Gln Asn Asn Ser Thr Arg Trp Pro Val Phe Lys Ser Thr
                485                 490                 495

Glu Gln Lys Tyr Leu Thr Leu Asn Thr Glu Ser Pro Lys Val Tyr Thr
                500                 505                 510

Lys Leu Arg Ala Gln Gln Cys Arg Phe Trp Thr Leu Phe Phe Pro Lys
            515                 520                 525

Val Leu Glu Leu Thr Gly Asn Ile Asp Glu Ala Glu Arg Glu Trp Lys
        530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Ser Asp Phe
                565                 570

<210> SEQ ID NO 22
<211> LENGTH: 574
<212> TYPE: PRT
<213> ORGANISM: Felis catus

<400> SEQUENCE: 22

Glu Glu Asp Ile Ile Ile Thr Thr Lys Asn Gly Lys Val Arg Gly Met
1               5                   10                  15

Asn Leu Pro Val Leu Asp Gly Thr Val Thr Ala Phe Leu Gly Ile Pro
                20                  25                  30

Tyr Ala Gln Pro Pro Leu Gly Arg Leu Arg Phe Lys Lys Pro Gln Phe
            35                  40                  45

Leu Thr Lys Trp Ser Asp Ile Trp Asn Ala Thr Lys Tyr Ala Asn Ser
        50                  55                  60

Cys Tyr Gln Asn Ala Asp Gln Ser Phe Pro Gly Phe Pro Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Thr Pro Lys Pro Lys Asn Ala Thr Val Met Ile Trp
            100                 105                 110

Ile Tyr Gly Gly Gly Phe Gln Thr Gly Thr Ser Ser Leu Pro Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160
```

```
Glu Val Pro Gly Asn Met Gly Leu Phe Asp Gln Gln Leu Ala Leu Gln
                165                 170                 175

Trp Val Gln Lys Asn Ile Ala Ala Phe Gly Asn Pro Lys Ser Val
            180                 185                 190

Thr Leu Phe Gly Glu Ser Ala Gly Ala Gly Ser Val Ser Leu His Leu
        195                 200                 205

Leu Ser Pro Arg Ser Gln Pro Leu Phe Thr Arg Ala Ile Leu Gln Ser
    210                 215                 220

Gly Ser Ser Asn Ala Pro Trp Ala Val Met Ser Leu Asp Glu Ala Lys
225                 230                 235                 240

Asn Arg Thr Leu Thr Leu Ala Lys Phe Ile Gly Cys Ser Lys Glu Asn
                245                 250                 255

Asp Thr Glu Ile Ile Lys Cys Leu Arg Asn Lys Asp Pro Gln Glu Ile
                260                 265                 270

Leu Leu Asn Glu Leu Leu Val Val Pro Ser Asp Thr Leu Leu Ser Val
            275                 280                 285

Asn Phe Gly Pro Val Val Asp Gly Asp Phe Leu Thr Asp Met Pro Asp
        290                 295                 300

Thr Leu Leu Gln Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asp Ser Ile Ile Thr Arg Lys Glu Phe Gln Glu
                340                 345                 350

Gly Leu Lys Ile Tyr Phe Pro Gly Val Ser Glu Phe Gly Arg Glu Ala
            355                 360                 365

Ile Leu Phe Tyr Tyr Val Asp Leu Leu Asp Asp Gln Arg Ala Glu Lys
        370                 375                 380

Tyr Arg Glu Ala Leu Asp Asp Val Leu Gly Asp Tyr Asn Ile Ile Cys
385                 390                 395                 400

Pro Ala Leu Glu Phe Thr Thr Lys Phe Ser Glu Leu Gly Asn Asn Ala
                405                 410                 415

Phe Phe Tyr Tyr Phe Glu His Arg Ser Ser Gln Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Val Asn Tyr Thr Arg Ala Glu Glu Ile Leu Ser
        450                 455                 460

Arg Ser Ile Met Asn Tyr Trp Ala Asn Phe Ala Lys Tyr Gly Asn Pro
465                 470                 475                 480

Asn Gly Thr Gln Asn Asn Ser Thr Arg Trp Pro Ala Phe Arg Ser Thr
                485                 490                 495

Asp Gln Lys Tyr Leu Thr Leu Asn Ala Glu Ser Pro Lys Val Tyr Thr
            500                 505                 510

Lys Leu Arg Ala Gln Gln Cys Arg Phe Trp Thr Leu Phe Phe Pro Lys
        515                 520                 525

Val Leu Glu Met Thr Gly Asn Ile Asp Glu Ala Glu Arg Glu Trp Arg
530                 535                 540

Ala Gly Phe Tyr Arg Trp Asn Asn Tyr Met Met Asp Trp Lys Asn Gln
545                 550                 555                 560

Phe Asn Asp Tyr Thr Ser Lys Lys Glu Ser Cys Ala Gly Leu
                565                 570
```

```
<210> SEQ ID NO 23
<211> LENGTH: 574
<212> TYPE: PRT
<213> ORGANISM: Rattus sp.

<400> SEQUENCE: 23
```

| | | | | | | | | | | | | | | | |
|---|---|---|---|---|---|---|---|---|---|---|---|---|---|---|---|
| Glu | Glu | Asp | Val | Ile | Ile | Thr | Thr | Lys | Thr | Gly | Arg | Val | Arg | Gly | Leu |
| 1 | | | | 5 | | | | | 10 | | | | | 15 | |
| Ser | Met | Pro | Ile | Leu | Gly | Gly | Thr | Val | Thr | Ala | Phe | Leu | Gly | Ile | Pro |
| | | | 20 | | | | | 25 | | | | | 30 | | |
| Tyr | Ala | Gln | Pro | Pro | Leu | Gly | Ser | Leu | Arg | Phe | Lys | Lys | Pro | Gln | Pro |
| | | 35 | | | | | 40 | | | | | 45 | | | |
| Leu | Asn | Lys | Trp | Pro | Asp | Val | Tyr | Asn | Ala | Thr | Lys | Tyr | Ala | Asn | Ser |
| | 50 | | | | | 55 | | | | | 60 | | | | |
| Cys | Tyr | Gln | Asn | Ile | Asp | Gln | Ala | Phe | Pro | Gly | Phe | Gln | Gly | Ser | Glu |
| 65 | | | | | 70 | | | | | 75 | | | | | 80 |
| Met | Trp | Asn | Pro | Asn | Thr | Asn | Leu | Ser | Glu | Asp | Cys | Leu | Tyr | Leu | Asn |
| | | | | 85 | | | | | 90 | | | | | 95 | |
| Val | Trp | Ile | Pro | Val | Pro | Lys | Pro | Lys | Asn | Ala | Thr | Val | Met | Val | Trp |
| | | | 100 | | | | | 105 | | | | | 110 | | |
| Val | Tyr | Gly | Gly | Gly | Phe | Gln | Thr | Gly | Thr | Ser | Ser | Leu | Pro | Val | Tyr |
| | | | | 115 | | | | | 120 | | | | | 125 | |
| Asp | Gly | Lys | Phe | Leu | Thr | Arg | Val | Glu | Arg | Val | Ile | Val | Val | Ser | Met |
| | 130 | | | | | 135 | | | | | 140 | | | | |
| Asn | Tyr | Arg | Val | Gly | Ala | Leu | Gly | Phe | Leu | Ala | Phe | Pro | Gly | Asn | Ser |
| 145 | | | | | 150 | | | | | 155 | | | | | 160 |
| Glu | Ala | Pro | Gly | Asn | Met | Gly | Leu | Phe | Asp | Gln | Gln | Leu | Ala | Leu | Gln |
| | | | | 165 | | | | | 170 | | | | | 175 | |
| Trp | Ile | Gln | Arg | Asn | Ile | Ala | Ala | Phe | Gly | Gly | Asn | Pro | Lys | Ser | Val |
| | | | 180 | | | | | 185 | | | | | 190 | | |
| Thr | Leu | Phe | Gly | Glu | Ser | Ala | Gly | Ala | Ala | Ser | Val | Ser | Leu | His | Leu |
| | | | | 195 | | | | | 200 | | | | | 205 | |
| Leu | Cys | Pro | Gln | Ser | Tyr | Pro | Leu | Phe | Thr | Arg | Ala | Ile | Leu | Glu | Ser |
| | 210 | | | | | 215 | | | | | 220 | | | | |
| Gly | Ser | Ser | Asn | Ala | Pro | Trp | Ala | Val | Lys | His | Pro | Glu | Glu | Ala | Arg |
| 225 | | | | | 230 | | | | | 235 | | | | | 240 |
| Asn | Arg | Thr | Leu | Thr | Leu | Ala | Lys | Phe | Ile | Gly | Cys | Ser | Lys | Glu | Asn |
| | | | | 245 | | | | | 250 | | | | | 255 | |
| Glu | Lys | Glu | Ile | Ile | Thr | Cys | Leu | Arg | Ser | Lys | Asp | Pro | Gln | Glu | Ile |
| | | | 260 | | | | | 265 | | | | | 270 | | |
| Leu | Leu | Asn | Glu | Lys | Leu | Val | Leu | Pro | Ser | Asp | Ser | Ile | Arg | Ser | Ile |
| | | | | 275 | | | | | 280 | | | | | 285 | |
| Asn | Phe | Gly | Pro | Thr | Val | Asp | Gly | Asp | Phe | Leu | Thr | Asp | Met | Pro | His |
| | 290 | | | | | 295 | | | | | 300 | | | | |
| Thr | Leu | Leu | Gln | Leu | Gly | Lys | Val | Lys | Thr | Ala | Gln | Ile | Leu | Val | Gly |
| 305 | | | | | 310 | | | | | 315 | | | | | 320 |
| Val | Asn | Lys | Asp | Glu | Gly | Thr | Ala | Phe | Leu | Val | Tyr | Gly | Ala | Pro | Gly |
| | | | | 325 | | | | | 330 | | | | | 335 | |
| Phe | Ser | Lys | Asp | Asn | Asp | Ser | Leu | Ile | Thr | Arg | Arg | Glu | Phe | Gln | Glu |
| | | | 340 | | | | | 345 | | | | | 350 | | |
| Gly | Leu | Asn | Met | Tyr | Phe | Pro | Gly | Val | Ser | Ser | Leu | Gly | Lys | Glu | Ala |
| | | | | 355 | | | | | 360 | | | | | 365 | |
| Ile | Leu | Phe | Tyr | Tyr | Val | Asp | Trp | Leu | Gly | Asp | Gln | Thr | Pro | Glu | Val |
| | 370 | | | | | 375 | | | | | 380 | | | | |

```
Tyr Arg Glu Ala Phe Asp Asp Ile Ile Gly Asp Tyr Asn Ile Ile Cys
385                 390                 395                 400

Pro Ala Leu Glu Phe Thr Lys Lys Phe Ala Glu Leu Glu Ile Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Val Asn Tyr Thr Arg Ala Glu Glu Ile Phe Ser
    450                 455                 460

Arg Ser Ile Met Lys Thr Trp Ala Asn Phe Ala Lys Tyr Gly His Pro
465                 470                 475                 480

Asn Gly Thr Gln Gly Asn Ser Thr Val Trp Pro Val Phe Thr Ser Thr
            485                 490                 495

Glu Gln Lys Tyr Leu Thr Leu Asn Thr Glu Lys Ser Lys Ile Asn Ser
            500                 505                 510

Lys Leu Arg Ala Pro Gln Cys Gln Phe Trp Arg Leu Phe Phe Pro Lys
        515                 520                 525

Val Leu Glu Ile Thr Gly Asp Ile Asp Glu Arg Glu Gln Glu Trp Lys
    530                 535                 540

Ala Gly Phe His Arg Trp Ser Asn Tyr Met Met Asp Trp Lys Asn Gln
545                 550                 555                 560

Phe Asn Asp Tyr Thr Ser Lys Lys Glu Thr Cys Thr Asp Leu
            565                 570

<210> SEQ ID NO 24
<211> LENGTH: 34
<212> TYPE: DNA
<213> ORGANISM: Artificial Sequence
<220> FEATURE:
<223> OTHER INFORMATION: human butyrylcholinesterase variant

<400> SEQUENCE: 24
gaagttccta ttctctagaa agtataggaa cttc                           34
```

US 7,070,973 B2

BUTYRYLCHOLINESTERASE VARIANTS AND METHODS OF USE

This invention was made with government support under grant number 1R01 DA011707 awarded by the National Institutes of Health. The United States Government has certain rights in this invention.

BACKGROUND OF THE INVENTION

This invention relates to butyrylcholinesterase variants and, more specifically to the production and therapeutic use thereof.

Cocaine abuse is a significant social and medical problem in the United States as evidenced by the estimated 3.6 million chronic users. Cocaine abuse often leads to long-term dependency as well as life-threatening overdoses. However, no effective antagonist is currently available that combats the reinforcing and toxic effects of cocaine.

One difficulty in identifying an antagonist to treat cocaine abuse arises largely from the narcotic's mechanism of action. Specifically, cocaine inhibits the re-uptake of neurotransmitters resulting in over-stimulation of the reward pathway. It is this over-stimulation that is proposed to be the basis of cocaine's reinforcing effect. In addition, at higher concentrations, cocaine interacts with multiple receptors in both the central nervous and cardiovascular systems, leading to toxicities associated with overdose. Because of this multifarious mechanism of action of cocaine, it is difficult to identify selective antagonists to treat both the reinforcing and toxic effects of cocaine. Additionally, antagonists that block cocaine's binding to its receptors tend to display many of the same deleterious effects as cocaine.

Recently, alternative treatment strategies based on intercepting and neutralizing cocaine in the bloodstream have been proposed. For example, dopamine D1, D2, and D3 antagonists affect the reinforcing potency of cocaine in the rat model, these antagonists display a narrow range of effective doses and the extent of decrease in cocaine potency is quite small. In addition, these dopamine antagonists produce profound decreases in other behaviors when the doses are increased only slightly above the levels that display an effect on cocaine self-administration behavior.

A separate treatment strategy involves partial protection against the effects of cocaine using antibody-based approaches. Limitations of immunization approaches include the stoichiometric depletion of the antibody following the binding of cocaine. The use of a catalytic antibody, which metabolizes cocaine in the bloodstream, partially mitigates this problem by degrading and releasing cocaine, permitting binding of additional cocaine. However, the best catalytic antibody identified to date metabolizes cocaine significantly slower than endogenous human serum esterases.

In vivo, cocaine is metabolized by three principal routes: 1) N-demethylation in the liver to form norcocaine, 2) hydrolysis by serum and liver esterases to form ecgonine methyl ester, and 3) nonenzymatic hydrolysis to form benzoylecgonine. In humans, norcocaine is a minor metabolite, while benzoylecgonine and ecgonine methyl ester account for about 90% of a given dose. The metabolites of cocaine are rapidly cleared and appear not to display the toxic or reinforcing effects of cocaine. Low serum levels of butyrylcholinesterase have been correlated with adverse physiological events following cocaine overdose, providing further evidence that butyrylcholinesterase accounts for the cocaine hydrolysis activity observed in plasma. Human plasma obtained from individuals with a defective version of the butyrylcholinesterase gene has been shown to have little or no ability to hydrolyze cocaine in vitro, and the hydrolysis of cocaine in plasma of individuals carrying one defective and one wild type copy of the butyrylcholinesterase gene has been shown to proceed at one-half the normal rate. Therefore, it has been suggested that individuals with defective versions of the butyrylcholinesterase gene are at higher risk for life-threatening reactions to cocaine. Recently, administration of butyrylcholinesterase has been demonstrated to confer limited protection against cocaine overdose in mice and rats.

Although administration of butyrylcholinesterase provides some effect against cocaine toxicity in vivo, it is not an efficient catalyst of cocaine hydrolysis. The low cocaine hydrolysis activity of wild-type butyrylcholinesterase requires the use of prohibitively large quantities of purified enzyme for therapy.

A number of naturally occurring human butyrylcholinesterases as well as species variations are known, none of which exhibits increased cocaine hydrolysis activity. Similarly, although a variety of recombinantly prepared butyrylcholinesterase mutations have been tested for increased cocaine hydrolysis activity, only one such mutant, termed A328Y, has been identified that exhibits increased cocaine hydrolysis activity. Further butyrylcholinesterase mutations that lead to increased cocaine hydrolysis activity need to be identified to permit clinical evaluation of butyrylcholinesterase.

Thus, there exists a need for butyrylcholinesterase variants capable of hydrolyzing cocaine significantly more efficiently than wild-type butyrylcholinesterase. The present invention satisfies this need and provides related advantages as well.

SUMMARY OF THE INVENTION

The invention provides four butyrylcholinesterase variants having increased cocaine hydrolysis activity as well as the corresponding encoding nucleic acids. The invention also provides libraries comprising butyrylcholinesterase variants having at least one amino acid alteration in one or more regions of butyrylcholinesterase and further having at least one butyrylcholinesterase variant exhibiting enhanced cocaine hydrolysis activity compared to butyrylcholinesterase. The invention further provides methods of hydrolyzing a cocaine-based butyrylcholinesterase substrate as well as methods of treating a cocaine-induced condition.

BRIEF DESCRIPTION OF THE DRAWINGS

FIG. 1A–1D shows the nucleic acid sequence designated SEQ ID NO: 1 and the deduced amino acid sequence of the butyrylcholinesterase variant designated SEQ ID NO: 2.

FIG. 2 shows the amino acid sequence of human butyrylcholinesterase with the seven regions designated SEQ ID NOS: 9 through 15 underlined and aromatic active gorge residues shaded: W82, W112, Y128, W231, F329, Y332, W430 and Y440.

FIG. 3 shows the nucleic acid sequence of human butyrylcholinesterase (SEQ ID NO: 16).

FIG. 4 shows an amino acid sequence alignment of human wild-type (SEQ ID NO: 17), human A variant (SEQ ID NO: 18), human J variant (SEQ ID NO: 19), human K variant (SEQ ID NO: 20), horse (SEQ ID NO: 21), cat (SEQ ID NO: 22) and rat butyrylcholinesterase variants (SEQ ID NO: 23).

FIG. 6 shows solid phase immobilization of wild-type (filled circles) and truncated (open circles) butyrylcholinesterase for measuring cocaine hydrolysis activity.

FIG. 7 shows the use of multiple synthesis columns and codon-based mutagenesis for the synthesis of focused libraries.

DETAILED DESCRIPTION OF THE INVENTION

Figure 5A:
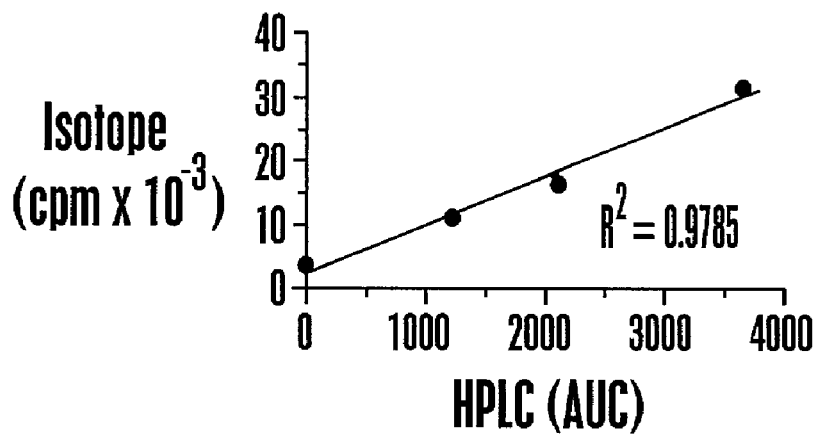
FIG. 5 shows (A) the correlation between the HPLC assay and the isotope tracer assay as demonstrated by plotting the quantitation of benzoic acid formation by both methods, and (B) the $K_m$ for cocaine hydrolysis activity of horse butyrylcholinesterase using the Lineweaver-Burk double-reciprocal plot.

This invention provides four butyrylcholinesterase variants that exhibit increased cocaine hydrolysis activity compared to butyrylcholinesterase. The identification of butyrylcholinesterase variants that exhibit increased cocaine hydrolysis activity provides treatment options for cocaine-induced conditions such as cocaine overdose and cocaine addiction.

In one embodiment, the invention provides a method of treating an individual suffering from symptoms due to cocaine toxicity including grand-mal seizures, cardiac arrest, stroke, and drug-induced psychosis accompanied by elevated blood pressure. The butyrylcholinesterase variants of the invention hold significant clinical value because of their capability to hydrolyze cocaine at a higher rate than any of the known naturally occurring variants. It is this increase in cocaine hydrolysis activity that enables a much more rapid response to the life-threatening symptoms of cocaine toxicity that sets the butyrylcholinesterase variants of the invention apart from other treatment options.

The invention also provides libraries of butyrylcholinesterase variants as well as of nucleic acids encoding butyrylcholinesterase variants. The butyrylcholinesterase variant libraries of the invention have one or more amino acid alterations in regions determined to be important for cocaine hydrolysis activity. Therefore, the invention provides libraries that can be screened for butyrylcholinesterase variants exhibiting increased cocaine hydrolysis activity.

As used herein, the term "butyrylcholinesterase" is intended to refer to a polypeptide having the sequence of naturally occurring butyrylcholinesterase. A naturally occurring butyrylcholinesterase can be of any species origin, for example, human, primate, horse, or murine. Therefore, a butyrylcholinesterase can be, for example a mammalian butyrylcholinesterase. In addition, a butyrylcholinesterase of the invention can be an isotype variation, polymorphism or any other allelic variation of a naturally occurring butyrylcholinesterase. A nucleic acid encoding a butyrylcholinesterase of the invention encodes a polypeptide having the sequence of any naturally occurring butyrylcholinesterase. Therefore, a nucleic acid encoding a butyrylcholinesterase can encode a butyrylcholinesterase of any species origin, for example, human, primate, horse, or murine. In addition, a nucleic acid encoding a butyrylcholinesterase encompasses any naturally occurring allele, isotype or polymorphism.

As used herein, the term "butyrylcholinesterase variant" is intended to refer to a molecule that is structurally similar to butyrylcholinesterase, but differs by at least one amino acid from butyrylcholinesterase. A butyrylcholinesterase variant has substantially the same amino acid sequence as butyrylcholinesterase and exhibits cocaine hydrolysis activity. In this regard, a butyrylcholinesterase variant can possess, for example, reduced, substantially the same or increased cocaine hydrolysis activity compared to butyrylcholinesterase. For example, the cocaine hydrolysis activity of a butyrylcholinesterase variant of the invention can be increased by a factor of 5, 10, 50, 100 or more.

A butyrylcholinesterase variant can have a single amino acid alteration as well as multiple amino acid alterations compared to butyrylcholinesterase. A specific example of a butyrylcholinesterase variant is butyrylcholinesterase having the amino acid Tryptophan at position 328, of which the amino acid sequence and encoding nucleic acid sequence is shown in FIG. 1 and designated as SEQ ID NOS: 2 and 1, respectively. Additional examples of butyrylcholinesterase variants are butyrylcholinesttrase having the amino acid Glycine at position 287, of which the amino acid sequence and nucleic acid sequence are described herein and designated SEQ ID NOS: 4 and 3, respectively; butyrylcholinesterase having the amino acid Glutamine at position 285, of which the amino acid sequence and nucleic acid sequence are described herein and designated SEQ ID NOS: 6 and 5, respectively; and butyrylcholinesterase having the amino acid Serine at position 285, of which the amino acid sequence and nucleic acid sequence are described herein and designated SEQ ID NOS: 8 and 7, respectively. The term is also intended to include butyrylcholinesterase variants encompassing, for example, modified forms of naturally occurring amino acids such as D-stereoisomers, non-naturally occurring amino acids, amino acid analogues and mimetics so long as such variants have substantially the same amino acid sequence as butyrylcholinesterase and exhibit cocaine hydrolysis activity. A butyrylcholinesterase variant of the invention can have one or more amino acid alterations outside of the regions determined or predicted to be important for cocaine hydrolysis activity herein. Furthennore, a butyrylcholinesterase variant of the invention can have one or more additional modifications that do not significantly change its cocaine hydrolysis activity. A butyrylcholinesterase variant of the invention can also have increased stability compared to butyrylcholinesterase.

As used herein, the term "substantially the same" when used in reference to an amino acid sequence is intended to mean a polypeptide, fragment or segment having an identical amino acid sequence, or a polypeptide, fragment or segment having a similar, non-identical sequence that is considered by those skilled in the art to be a functionally equivalent amino acid sequence. An amino acid sequence that is substantially identical to a reference butyrylcholinesterase or butyrylcholinesterase variant of the invention can have at least 70%, at least 80%, at least 81%, at least 83%, at least 85%, at least 90%, at least 95% or more identity to the reference butyrylcholinesterase. Substantially the same amino acid sequence is also intended to include polypeptides encompassing, for example, modified forms of naturally occurring amino acids such as D-stereoisomers, non-naturally occurring amino acids, amino acid analogues and mimetics so long as such polypeptides retain functional activity as defined above. A biological activity of a butyrylcholinesterase variant of the invention is cocaine hydrolysis activity as described herein. For example, the butyrylcholinesterase variant A328W designated SEQ ID NO: 2 exhibits at least a fifteen-fold increased cocaine hydrolysis activity compared to butyrylcholinesterase; the butyrylcholinesterase variant S287G designated SEQ ID NO: 4 exhibits at least a four-fold increased cocaine hydrolysis activity compared to butyrylcholinesterase; the butyrylcholinesterase variant P285Q designated SEQ ID NO: 6 exhibits approximately a four-fold increased cocaine hydrolysis activity compared to butyrylcholinesterase; the butyrylcholinesterase variant P285S designated SEQ ID NO: 8 exhibits approximately a three-fold increased cocaine hydrolysis activity compared to butyrylcholinesterase.

It is understood that minor modifications in the primary amino acid sequence can result in a polypeptide that has a substantially equivalent function as compared to a polypeptide of the invention. These modifications can be deliberate, as through site-directed mutagenesis, or may be accidental such as through spontaneous mutation. For example, it is understood that only a portion of the entire primary structure of a butyrylcholinesterase variant can be required in order to effect cocaine hydrolysis activity. Moreover, fragments of the sequence of a butyrylcholinesterase variant of the invention are similarly included within the definition as long as at least one biological function of the butyrylcholinesterase variant is retained. It is understood that various molecules can be attached to a polypeptide of the invention, for example, other polypeptides, carbohydrates, lipids, or chemical moieties.

As used herein, the term "corresponding to" refers to an amino acid sequence that is substantially the same as a reference amino acid sequence. The amino acid sequence can occupy the same or different amino acid positions relative to the reference polypeptide, fragment or segment. It is understood that, while butyrylcholinesterases of different species origin as well as allelic variations will have substantiaUy identical amino acid sequences, the physical locations as well as the size of a particular amino acid sequence may vary. Therefore, the amino acids making up a given segment in a butyrylcholinesterase or butyrylcholinesterase variant may not be in the same physical location or occupy the identical amino acid positions as in the reference butyrylcholinesterase or butyrylcholinesterase variant. For example, butyrylcholinesterases of different species origin as well as allelic variations have substantially similar amino acid sequences, but the amino acid positions making up a region may not correspond to those recited for SEQ ID NOS: 9 through 15. For example, a region that is substantially similar in amino acid sequence to the region designated as SEQ ID NO: 9 may not occupy amino acid positions 68–82 in a non-human butyrylcholinesterase or an allelic variation of any species origin, but is nevertheless encompassed by the present invention.

As used herein, the term "substantially the same" in reference to a nucleic acid molecule of the invention or a fragment thereof includes sequences having one or more additions, deletions or substitutions with respect to the reference sequence, so long as the nucleic acid molecule retains ita ability to selectively hybridize with the subject nucleic add molecule under moderately stringent conditions, or highly stringent conditions. The term "moderately stringent conditions," as used herein, refers to hybridization conditions equivalent to hybridization of filter-bound nucleic acid in 50% formamide, 5× Denhsrdt's solution, 5×SSPE, 0.2% SDS at 42° C., followed by washing in 0.2×SSPE, 02% SDS, at 50°. As used herein, "highly stringent conditions" are conditions equivalent to hybridization of filter-bound nucleic acid in 50% formamide, 5× Denherdt's solution, 5×SSPE, 0.2% SDS at 42° C., followed by washing in 0.2×SSPE, 0.2% SDS, at 65°. Other suitable moderately stringent and highly stringent hybridization buffers and conditions are well known to those of skill in the art and are described, for example, in Sambrook et al., *Molecular Cloning: A Laboratory Manual*, Cold Spring Harbor Laboratory, New York (1992) and in Ausubel et al., *Current Protocols in Molecular Biology*, John Wiley and Sons, Baltimore, Md. (1998). Thus, it is not necessary that two nucleic, acids exhibit sequence identity to be substantially complementary, only that they can specifically hybridize or be made to specifically hybridize without detectable cross reactivity with other similar sequences.

In general, a nucleic acid molecule that has "substantially the same" nucleotide sequence as a reference sequence will have greater than about 60% identity, such as greater than about 65%, 70%, 75% identity with the reference sequence, such as greater than about 80%, 85%, 90%, 95%, 97% or 99% identity to the reference sequence over the length of the two sequences being compared. Identity of any two nucleic acid sequences can be determined by those skilled in the art based, for example, on a BLAST 2.0 computer alignment, using default parameters. BLAST 2.0 searching is available at ncbi.nlm.nih.gov/gorf/bl2.html., as described by Tatiana et al., *FEMS Microbiol Lett.* 174:247–250 (1999).

As used herein, the term "fragment" when used in reference to a nucleic acid encoding the claimed polypeptides is intended to mean a nucleic acid having substantially the same sequence as a portion of a nucleic acid encoding a polypeptide of the invention or segments thereof. The nucleic acid fragment is sufficient in length and sequence to selectively hybridize to a butyrylcholinesterase variant encoding nucleic acid or a nucleotide sequence that is complementary to a butyrylcholinesterase variant encoding nucleic acid. Therefore, fragment is intended to include primers for sequencing and polymerase chain reaction (PCR) as well as probes for nucleic acid blot or solution hybridization.

Similarly, the term "functional fragment" when used in reference to a nucleic acid encoding a butyrylcholinesterase or butyrylcholinesterase variant is intended to refer to a portion of the nucleic acid that encodes a portion of the butyrylcholinesterase or butyrylcholinesterase variant that still retains some or all of the cocaine hydrolysis activity of the parent polypeptide. A functional fragment of a polypeptide of the invention exhibiting a functional activity can have, for example, at least 6 contiguous amino acid residues from the polypeptide, at least 8, 10, 15, 20, 30 or 40 amino acids, and often has at least 50, 75, 100, 200, 300, 400 or more amino acids of a polypeptide of the invention, up to the full length polypeptide minus one amino acid.

As used herein, the term "functional fragment" in regard to a polypeptide of the invention, refers to a portion of the reference polypeptide that is capable of exhibiting or carrying out a "functional activity" of the reference polypeptide. A functional fragment of a polypeptide of the invention exhibiting a functional activity can have, for example, at least 6 contiguous amino acid residues from the polypeptide, at least 8, 10, 15, 20, 30 or 40 amino acids, and often has at least 50, 75, 100, 200, 300, 400 or more amino acids of a polypeptide of the invention, up to the full length polypeptide minus one amino acid. The appropriate length and amino acid sequence of a functional fragment of a polypeptide of the invention can be determined by those skilled in the art, depending on the intended use of the functional fragment. For example, a functional fragment of a butyrylcholinesterase or butyrylcholinesterase variant is intended to refer to a portion of the butyrylcholinesterase or butyrylcholinesterase variant that still retains some or all of the cocaine hydrolysis activity of the parent polypeptide.

As used herein, the term "library" means a collection of molecules. A library can contain a few or a large number of different molecules, varying from as small as 2 molecules to as large as $10^{13}$ or more molecules. Therefore, a library can range in size from 2 to 10, 10 to $10^2$, $10^2$ to $10^3$, $10^3$ to $10^5$, $10^5$ to $10^8$, $10^8$ to $10^{10}$ or $10^{10}$ to $10^{13}$ molecules. The molecules making up a library can be nucleic acid molecules such as an RNA, a cDNA or an oligonucleotide; a peptide or polypeptide including a variant or modified peptide or a peptide containing one or more amino acid analogs. In addition, the molecules making up a library can be peptide-like molecules, referred to herein as peptidomimetics, which mimic the activity of a peptide; or a polypeptide such as an enzyme or a fragment thereof. Moreover, a library can be diverse or redundant depending on the intent and needs of the user. Those skilled in the art will know the size and diversity of a library suitable for a particular application.

As used herein, the term "region" is intended to refer to an area of the amino acid sequence of butyrylcholinesterase that is determined or predicted to be important for cocaine hydrolysis activity. As described below, a region has been determined or predicted to be important for cocaine hydrolysis activity by using one or more of structural, biochemical or modeling methods and, as a consequence, is defined by general rather than absolute boundaries. A region can encompass two or more consecutive amino acid positions of the amino acid sequence of butyrylcholinesterase that are predicted to be important for cocaine hydrolysis activity. A region of butyrylcholinesterase useful for practicing the claimed invention is no more than about 30 amino acids in length and preferably is between 2 and 20, between 5 and 15 amino acids in length.

As used herein, the term "cocaine hydrolysis activity," is intended to refer to the catalytic action of a butyrylcholinesterase or butyrylcholinesterase variant as measured by the rate of cocaine hydrolysis into the metabolites.

As used herein, the term "alteration" is intended to refer to a modification at an amino acid position of butyrylcholinesterase. An amino acid alteration therefore can be a substitution, deletion or any other structural modification at an amino acid position. An amino acid alteration can occur directly at the amino acid level or result from translation of a nucleic acid encoding an amino acid alteration. An amino acid alteration can lead to the replacement of an amino acid with a ne*er another amino acid or with an amino acid analog. Examples of an amino acid alteration include the amino acid substitution of Alanine (A) with Tryptophan (W) resulting in the butyryichoinesterase variant designated SEQ ID NO: 2; the amino acid substitution of Serine (S) with Glycine (G) resulting in the butyrylcholinesterse variant designated SEQ ID NO: 4; the amino acid substitution of Proline (P) with Glutamine (Q) resulting in the butyrylcholinesterase variant designated SEQ ID NO: 6; and the amino acid substitution of Proline (P) with Serine (S) resulting in the butyrylcholinesterase variant designated SEQ ID NO: 8.

As used herein, the term "effective amount" is intended to mean an amount of a butyrylcholinesterase variant of the invention that can reduce the cocaine-toxicity or the severity of a cocaine-induced condition. Reduction in severity includes, for example, an arrest or a decrease in symptoms, physiological indicators, biochemical markers or metabolic indicators. Symptoms of cocaine overdose include, for example, cardiac arrythmias, seizures and hypertensive crises. As used herein, the term "treating" is intended to mean causing a reduction in the severity of a cocaine-induced condition.

As used herein, the term "cocaine-based substrate" refers to (−)-cocaine or any molecule sufficiently similar to (−)-cocaine in structure to be hydrolyzed by butyrylcholinesterase or a butyrylcholinesterase variant including, for example, (+)-cocaine, acetylcholine, butyrylthiocholine, benzoylcocaine and norcocaine.

The invention provides a butyrylcholinesterase variant comprising substantially the same amino acid sequence shown as SEQ ID NO: 2, or functional fragment thereof. The invention also provides a butyrylcholinesterase variant having a 15-fold increase in cocaine hydrolysis activity, or functional fragment thereof. The invention also provides a nucleic acid shown as SEQ ID NO: 1, or fragment thereof, which encodes a butyrylcholinesterase variant comprising substantially the same amino acid sequence shown as SEQ ID NO: 2.

The invention also provides a butyrylcholinesterase variant comprising substantially the same amino acid sequence shown as SEQ ID NO: 4, or functional fragment thereof. The invention also provides a butyrylcholinesterase variant having at least a 4-fold increase in cocaine hydrolysis activity, or functional fragment thereof. The invention further provides a nucleic acid shown as SEQ ID NO: 3, or fragment thereof, which encodes a butyrylcholinesterase variant comprising substantially the same amino acid sequence shown as SEQ ID NO: 4. As shown in Table 1, the nucleic acid shown as SEQ ID: 3 differs from the nucleic acid encoding human butyrylcholinesterase shown in FIG. 3 and designated SEQ ID NO: 16, at positions 1072 through 1074, which correspond to the codon encoding amino acid residue 287. In the human butyrylcholinesterase (SEQ ID NO: 16) the codon tca at nucleotide positions 1072 through 1074 encodes Serine. In contrast, in the nucleic acid encoding the S285G butyrylcholinesterase variant designated SEQ ID NO: 3, the codon ggt at nucleotide positions 1072 through 1074 encodes the amino acid Glycine.

The invention provides a further butyrylcholinesterase variant comprising substantially the same amino acid sequence shown as SEQ ID NO: 6, or functional fragment thereof. The invention also provides a further butyrylcholinesterase variant, having approximately a 4-fold increase in cocaine hydrolysis activity, or functional fragment thereof. The invention further provides a nucleic acid shown as SEQ ID NO: 5, or fragment thereof, which encodes a butyrylcholinesterase variant comprising substantially the same amino acid sequence designated SEQ ID NO: 6. As shown in Table 1, the nucleic acid shown as SEQ ID: 5 differs from nucleic acid encoding human butyrylcholinesterase shown in FIG. 3 and designated SEQ ID NO: 16, at positions 1066 through 1068, which correspond to the codon encoding amino acid residue 285. In the human butyrylcholinesterase (SEQ ID NO: 16) the codon cct at nucleotide positions 1066 through 1068 encodes Proline. In contrast, in the nucleic acid encoding the P285Q butyrylcholinesterase variant designated SEQ ID NO 5, the codon cag at nucleotide positions 1066 through 1068 encodes the amino acid Glutamine.

The invention provides a further butyrylcholinesterase variant comprising substantially the same amino acid sequence shown as SEQ ID NO: 8, or functional fragment thereof. The invention also provides a further butyrylcholinesterase variant, having approximately a three-fold increase in cocaine hydrolysis activity, or functional fragment thereof. The invention also provides a nucleic acid shown as SEQ ID NO: 7, or fragment thereof, which encodes a butyrylcholinesterase variant comprising substantially the same amino acid sequence shown as SEQ ID NO: 8. As shown in Table 1, the nucleic acid shown as SEQ ID: 7 differs from nucleic acid encoding human butyrylcholinesterase as shown in FIG. 3 and designated SEQ ID NO: 16, at positions 1066 through 1068, which correspond to the codon encoding amino acid residue 285. In the human butyrylcholinesterase (SEQ ID NO: 16) the codon cct at nucleotide positions 1066 through 1068 encodes Proline. In contrast, in the nucleic acid encoding P285S butyrylcholinesterase variant designated SEQ ID NO: 7, the codon tcg at nucleotide positions 1066 through 1068 encodes the amino acid Serine.

Cholinesterases are ubiquitous, polymorphic carboxylase Type B enzymes capable of hydrolyzing the neurotransmitter acetylcholine and numerous ester-containing compounds. Two major cholinesterases are acetylcholinesterase and butyrylcholinesterase. Butyrylcholinesterase catalyzes the hydrolysis of a number of choline esters as shown:

$$\text{Acetylcholine} + \text{H2O} \xrightarrow{\text{BChE}} \text{Choline} + \text{Corresponding Acid}$$

Butyrylcholinesterase preferentially uses butyrylcholine and benzoylcholine as substrates. Butyrylcholinesterase is found in mammalian blood plasma, liver, pancreas, intestinal mucosa and the white matter of the central nervous system. The human gene encoding butyrylcholinesterase is located on chromosome 3 and over thirty naturally occuring genetic variations of butyrylcholinesterase are known. The butyrylcholinesterase polypeptide is 574 amino acids in length and encoded by 1,722 base pairs of coding sequence. Three naturally occuring butyrylcholinesterase variations are the atypical alleles referred to as A variant (SEQ ID NO: 18), the J variant (SEQ ID NO: 19) and the K variant (SEQ ID NO: 20), which are aligned in FIG. 4. The A variant has an D70G mutation and is rare (0.5% allelic frequency), while the J variant has a E497V mutation and has only been found in one family. The K variant has a point mutation at nucleotide 1615, which results in an A539T mutation and has an allelic frequency of around 12% in Caucasians.

In addition to the naturally-occurring human variations of butyrylcholinesterase, a number of species variations are known. The amino acid sequence of cat butyrylcholinesterase is 88% identical with human butyrylcholinesterase (see FIG. 4). Of the seventy amino acids that differ, three are located in the active site gorge and are termed A277L, P285L and F398I. Similarly, horse butyrylcholinesterase has three amino acid differences in the active site compared with human butyrylcholinesterase, which are A277V, P285L and F398I (see FIG. 4). The amino acid sequence of rat butyrylcholinesterase contains 6 amino acid differences in the active site gorge, which are A277K, V280L, T284S, P285I, L286R and V288I (see FIG. 4).

Naturally occurring human butyrylcholinesterase variations, species variations as well as recombinantly prepared mutations have previously been described by Xie et al., *Molecular Pharmacology* 55:83–91 (1999). Recombinant human butyrylcholinesterase mutants that have been tested for increased cocaine hydrolysis activity include mutants with the following single or multiple changes: N68Y/Q119/A277W, Q119/V288F/A328Y, Q119Y, E197Q, V288F, A328F, A328Y, F329A and F329S. Out of these mutants, the only butyrylcholinesterase mutant identified that exhibits increased cocaine hydrolysis activity is the A328Y mutant, which has a Tyrosine (Y) rather than an Alanine (A) at amino acid position 328 and exhibits a four-fold increase in cocaine hydrolysis activity compared to human butyrylcholinesterase (Xie et al., supra, 1999).

The invention provides a butyrylcholinesterase variant shown as SEQ ID NO: 2 that has substantially the same amino acid sequence as human butyrylcholinesterase, but includes at amino acid position 328 of human butyrylcholinesterase (SEQ ID NO: 17) a Tryptophan (W) substitution in place of the encoded Alanine (A) residue. The A328W butyrylcholinesterase variant (SEQ ID NO: 2) was obtained by PCR site-directed mutagenesis of human butyrylcholinesterase as described in Example I below and exhibits at least a fifteen-fold increase in cocaine hydrolysis activity compared to human butyrylcholinesterase.

The invention further provides a butyrylcholinesterase variant shown as SEQ ID NO: 4 that has substantially the same amino acid sequence as human butyrylcholinesterase, but includes at amino acid position 287 of human butyrylcholinesterase (SEQ ID NO: 17) a Glycine (G) substitution in place of the Serine (S) residue encoded in human butyrylcholinesterase. The S287G butyrylcholinesterase variant (SEQ ID NO: 4) is encoded by a nucleotide sequence (SEQ ID NO: 3) that is substantially the same as that of human butyrylcholinesterase (SEQ ID NO:16), but has the codon ggt encoding the amino acid Glycine instead of the codon tca encoding Serine at the nucleotide positions corresponding to position 287 of human butyrylcholinesterase (SEQ ID NO: 17). The S287G butyrylcholinesterase variant (SEQ ID NO: 4) was obtained as described in Examples II through VI below and exhibits at least a four-fold increase in cocaine hydrolysis activity compared to human butyrylcholinesterase.

The invention provides a butyrylcholinesterase variant shown as SEQ ID NO: 6 that has substantially the same amino acid sequence as human butyrylcholinesterase, but includes at amino acid position 285 of human butyrylcholinesterase (SEQ ID NO: 17) a Glutamine (Q) substitution in place of the encoded Proline (P) residue. The P285Q butyrylcholinesterase variant (SEQ ID NO: 6) is encoded by a nucleotide sequence (SEQ ID NO: 5) that is substantially the same as that of human butyrylcholinesterase (SEQ ID NO: 16), but has the codon cag encoding the amino acid Glutamine instead of the codon cct encoding Proline at the nucleotide positions corresponding to position 285 of human butyrylcholinesterase (SEQ ID NO: 17). The P285Q butyrylcholinesterase variant (SEQ ID NO: 6) was obtained as described in Examples II through VI below and exhibits an approximately four-fold increase in cocaine hydrolysis activity compared to human butyrylcholinesterase.

The invention also provides a butyrylcholinesterase variant shown as SEQ ID NO: 8 that has substantially the same amino acid sequence as human butyrylcholinesterase, but includes at amino acid position 285 of human butyrylcholinesterase (SEQ ID NO: 16) a Serine (S) substitution in place of the encoded Proline (P) residue. The P285S butyrylcholinesterase variant (SEQ ID NO: 8) is encoded by a nucleotide sequence (SEQ ID NO: 7) that is substantially the same as that of human butyrylcholinesterase (SEQ ID NO: 16), but has the codon tcg encoding the amino acid Serine instead of the codon cct encoding Proline at the nucleotide positions corresponding to position 287 of human butyrylcholinesterase (SEQ ID NO: 17). The P285S butyrylcholinesterase variant (SEQ ID NO: 8) was obtained as described in Examples II through VI below and exhibits an approximately three-fold increase in cocaine hydrolysis activity compared to human butyrylcholinesterase.

TABLE 1

| Nucleotide Sequences Corresponding to Amino Acid 284 through amino acid 288. | | |
|---|---|---|
| Human BchE | (SEQ ID NO:25) | act cct ttg tca gta |
| S287G | (SEQ ID NO:26) | act cct ttg ggt gta |

TABLE 1-continued Nucleotide Sequences Corresponding to
Amino Acid 284 through amino acid 288.

| | | |
|---|---|---|
| P285Q | (SEQ ID NO:27) | act cag ttg tca gta |
| P285S | (SEQ ID NO:28) | act tcg ttg tca gta |

A butyrylcholinesterase variant of the invention can be prepared by a variety of methods well known in the art. If desired, random mutagenesis can be performed to prepare a butyrylcholinesterase variant of the invention. Alternatively, as disclosed herein, site directed mutagenesis based on the information obtained from structural, biochemical and modeling methods described herein can be performed to target those amino acids predicted to be important for cocaine hydrolysis activity. For example, molecular modeling of cocaine in the active site of butyrylcholinesterase can be utilized to predict amino acid alterations that allow for higher catalytic efficiency based on a better fit between the enzyme and its substrate. As described herein, residues predicted to be important for cocaine hydrolysis activity Include 8 hydrophobic gorge residues and the catalytic triad residues. Furthermore, it is understood that amino acid alterations of residues important for the functional structure of a butyrylcholinesterese variant which include the cysteine residues $^{65}$Cys-$^{92}$Cys, $^{252}$Cys-$^{263}$Cys, and $^{400}$Cys-$^{519}$Cys involved in intrachain disulfide bonds are generally not altered in the preparation of a butyrylcholinesterase variant that has cocaine hydrolysis activity.

Following mutagenesis of butyrylcholinesterase or a butyrylcholinesterase variant expression, purification and functional characterization of the butyrylcholinesterase variant can be performed by methods well known in the art. As disclosed below, a butyrylcholinesterase variant can be expressed in an appropriate host cell line and subsequently purified and characterized for cocaine hydrolysis activity. Butyrylcholinesterase variants characterized as having significantly increased cocaine hydrolysis activity can subsequently be used in the methods of hydrolyzing a cocaine-based substrate as well as the methods of treating a cocaine-induced condition described below.

A butyrylcholinesterase variant of the invention exhibits cocaine hydrolysis activity. As disclosed herein, a butyrylcholinesterase variant of the invention can have enhanced cocaine hydrolysis activity and can be used to treat a cocaine-induced condition. A polypeptide having minor modifications compared to a butyrylcholinesterase variant of the invention is encompassed by the invention so long as equivalent cocaine hydrolysis activity is retained. In addition, functional fragments of a butyrylcholinesterase variant that still retain some or all of the cocaine hydrolysis activity of the parent butyrylcholinesterase variant are similarly included in the invention. Similarly, functional fragments of nucleic acids, which encode functional fragments of a butyrylcholinesterase variant of the invention are similarly encompassed by the invention.

A functional fragment of a butyrylcholinesterase or a butyrylcholinesterase variant of the invention can be prepared by recombinant methods involving expression of a nucleic acid molecule encoding the butyrylcholinesterase variant or functional fragment thereof, followed by isolation of the variant or functional fragment thereof by routine biochemical methods described herein. It is understood that functional fragments can also be prepared by enzymatic or chemical cleavage of the full length butyrylcholinesterase variant. Methods for enzymatic and chemical cleavage and for purification of the resultant peptide fragments are well known in the art (see, for example, Deutscher, *Methods in Enzymology*, Vol. 182, "Guide to Protein Purification," San Diego: Academic Press, Inc. (1990), which is incorporated herein by reference).

Furthermore, functional fragments of a butyrylcholinesterase variant can be produced by chemical synthesis. If desired, such molecules can be modified to include D-stereoisomers, non-naturally occurring amino acids, and amino acid analogs and mimetics in order to optimize their functional activity, stability or bioavailability. Examples of modified amino acids and their uses are presented in Sawyer, *Peptide Based Drug Design*, ACS, Washington (1995) and Gross and Meienhofer, *The Peptides: Analysis, Synthesis, Biology*, Academic Press, Inc., New York (1983), both of which are incorporated herein by reference.

If desired, random segments of a butyrylcholinesterase variant can be prepared and tested in the assays described herein. A fragment having any desired boundaries and modifications compared to the amino acid sequence of the reference butyrylcholinesterase or butyryloholinesterase variant of the invention can be prepared. Alternatively, available information obtained by the structural, biochemical and modeling methods described herein can be used to prepare only those fragments of a butyrylcholinesterase variant that are likely to retain the cocaine hydrolysis activity of the parent variant. As described herein, residues predicted to be important for cocaine hydrolysis activity include 8 hydrophobic gorge residues and the catalytic triad residues. Furthermore, residues important for the functional structure of a butyrylcholinesterase variant include the cysteine residues $^{65}$Cys-$^{92}$Cys, $^{252}$Cys-$^{263}$Cys, and $^{400}$Cys-$^{519}$Cys involved in intrachain disulfide bonds. Therefore, a functional fragment can be a truncated form, region or segment of the reference butyrylcholinesterase variant designed to possess most or all of the residues critical for cocaine hydrolysis activity or functional structure so as to retain equivalent cocaine hydrolysis activity. Similarly, a functional fragment can include non-peptidic structural elements that serve to mimic structurally or functionally important residues of the reference variant. Also included as butyrylcholinesterase variants of the invention are fusion proteins that result from linking a butyrylcholinesterase variant or functional fragment thereof to a heterologous protein, such as a therapeutic protein, as well as fusion constructs of nucleic acids encoding such fusion proteins. Fragments of nucleic acids that can hybridize to a butyrylcholinesterase variant or functional fragment thereof are useful, for example, as hybridization probes and are also encompassed by the claimed invention.

Thus, the invention provides four butyrylcholinesterase variants comprising substantially the same amino acid sequences shown as SEQ ID NOS: 2, 4, 6, and 8, respectively, or functional fragment thereof. The invention also provides a butyrylcholinesterase variant having a 15-fold increase in cocaine hydrolysis activity, or functional fragment thereof; a butyrylcholinesterase variant having at least a four-fold increase in cocaine hydrolysis activity, or functional fragment thereof; a butyrylcholinesterase variant having approximately 4-fold increase in cocaine hydrolysis activity, or functional fragment thereof; and a butyrylcholinesterase variant having approximately a three-fold increase in cocaine hydrolysis activity, or functional fragment thereof. The invention also provides four nucleic acids shown as SEQ ID NO: 1, 3, 5, and 7, respectively, or fragment thereof, which encode the butyrylcholinesterase variants comprising substantially the same amino acid sequences shown as SEQ ID NO: 2, 4, 6, and 8, respectively.

The invention also provides a library of butyrylcholinesterase variants having at least one amino acid alteration in one or more regions of butyrylcholinesterase corresponding to amino acid positions 68–82 (SEQ ID NO: 9), 110–121 (SEQ ID NO: 10), 194–201 (SEQ ID NO: 11), 224–234 (SEQ ID NO: 12), 277–289 (SEQ ID NO: 13), 327–332 (SEQ ID NO: 14) or 429–442 (SEQ ID NO: 15) of butyrylcholinesterase or functional fragment therof, wherein the library of butyrylcholinesterase variants of the invention has at least one butyrylcholinesterase variant exhibiting enhanced cocaine hydrolysis activity compared to butyrylcholinesterase, with the proviso that a butyrylcholinesterase variant having a single amino acid alteration is not the human butyrylcholinesterase having Y at position 328. The invention further provides a library of butyrylcholinesterase variants wherein said butyrylcholinesterase variants have at least two amino acid alterations.

In addition, the invention provides seven distinct libraries of butyrylcholinesterase variants, each variant having at least one amino acid alteration in a region of butyrylcholinesterase corresponding to amino acid positions 68–82 (SEQ ID NO: 9), 110–121 (SEQ ID NO: 10), 194–201 (SEQ ID NO: 11), 224–234 (SEQ ID NO: 12), 277–289 (SEQ ID NO: 13), 327–332 (SEQ ID NO: 14) or 429–442 (SEQ ID NO: 15) of butyrylcholinesterase or functional fragment thereof, respectively. A library of butyrylcholinesterase variants of the invention can be used to screen for butyrylcholinesterase variants with increased cocaine hydrolysis activity.

A library that is sufficiently diverse to contain a butyrylcholinesterase variant with enhanced cocaine hydrolysis activity can be prepared by a variety of methods well known in the art. Those skilled in the art will know what size and diversity is necessary or sufficient for the intended purpose. For example, a library of butyrylcholinesterase variants can be prepared that contains each of the 19 amino acids not found in the reference butyrylcholinesterase at each of the approximately 573 amino acid positions and screening the resultant variant library for butyrylcholinesterase variants with enhanced cocaine hydrolysis activity.

Alternatively, a focused library can be prepared utilizing the structural, biochemical and modeling information relating to butyrylcholinesterase as described herein. It is understood that any information relevant to the determination or prediction of residues or regions important for the cocaine hydrolysis activity or structural function of butyrylcholinesterase can be useful in the design of a focused library of butyrylcholinesterase variants of the invention. Thus, the butyrylcholinesterase variants that make up the library of butyrylcholinesterase variants of the invention can contain amino acid alterations at amino acid positions located in regions determined or predicted to be important for cocaine hydrolysis activity. A focused library of butyrylcholinesterase variants is desirable as it significantly decreases the number of variants that need to be screened in order to identify a butyrylcholinesterase variant with enhanced cocaine hydrolysis activity by targeting amino acid alterations to regions determined or predicted to be important for cocaine hydrolysis activity.

Regions important for the cocaine hydrolysis activity of butyrylcholinesterase can be determined or predicted through a variety of methods known in the art and used to focus the synthesis of a library of butyrylcholinesterase variants. Related enzymes such as, for example, acetylcholinesterase and carboxylesterase, that share a high degree of sequence similarity and have biochemically similar catalytic properties can provide information regarding the regions important for catalytic activity of butyrylcholinesterase. For example, structural modeling can reveal the active site of an enzyme, which is a three-dimensional structure such as a cleft, gorge or crevice formed by amino acid residues generally located apart from each other in primary structure. Therefore, amino acid residues that make up regions of butyrylcholinesterase important for cocaine hydrolysis activity can include residues located along the active site gorge. For a description of structural modeling of butyrylcholinesterase, see for example, Harel et al., *Proc. Nat. Acad. Sci. USA* 89: 10827–10831 (1992) and Soreq et al., Trends Biochem. Sci. 17(9): 353–358 (1992), which are incorporated herein by reference.

In addition to structural modeling of butyrylcholinesterase, biochemical data can be used to determine or predict regions of butyrylcholinesterase important for cocaine hydrolysis activity when preparing a focused library of butyrylcholinesterase variants. In this regard, the characterization of naturally occurring butyrylcholinesterase variants with altered cocaine hydrolysis activity is useful for identifying regions important for the catalytic activity of butyrylcholinesterase. Similarly, site-directed mutagenesis studies can provide data regarding catalytically important amino acid residues as reviewed, for example, in Schwartz et al; *Pharmac. Ther.* 67: 283–322 (1992), which is incorporated by reference.

To generate a library of butyrylcholinesterase variants of the invention distinct types of information can be used alone or combined to determine or predict a region of an amino acid sequence of butyrylcholinesterase important for cocaine hydrolysis activity. For example, information based on structural modeling and biochemical data is combined to determine a region of an amino acid sequence of butyrylcholinesterase important for cocaine hydrolysis activity. Because information obtained by a variety of methods can be combined to predict the catalytically active regions, one skilled in the art will appreciate that the regions themselves represent approximations rather than strict confines. As a result, a library of butyrylcholinesterases can contain butyrylcholinesterase variants that have amino acid alterations outside of the regions determined or predicted to be important for cocaine hydrolysis activity. Similarly, a butyrylcholinesterase variant of the invention can have amino acid alterations outside of the regions determined or predicted to be important for cocaine hydrolysis activity. Furthermore, a butyrylcholinesterase variant of the invention can have any other modification that does not significantly change its cocaine hydrolysis activity. It is further understood that the number of regions determined or predicted to be important for cocaine hydrolysis activity can vary based on the predictive methods used.

Once a number of regions has been identified by any method appropriate for determination of regions important for cocaine hydrolysis, or combination thereof, each region can be randomized across some or all amino acid positions to create a library of variants containing the wild-type amino acid plus one or more of the other nineteen naturally occurring amino acids at one or more positions within each of the regions. Seven regions of an amino acid sequence of butyrylcholinesterase selected for the focused library of butyrylcholinesterase variants provided by the invention are shown in Table 2.

TABLE 2

Summary of Butyrylcholinesterase Libraries

| Region | Location | Length | # Variants | Species Diversity |
|---|---|---|---|---|
| 1 | 68–82 | 15 | 285 | 3 |
| 2 | 110–121 | 12 | 228 | 3 |
| 3 | 194–201 | 8 | 152 | 1 |
| 4 | 224–234 | 11 | 209 | 2 |
| 5 | 277–289 | 13 | 247 | 8 |
| 6 | 327–332 | 6 | 114 | 0 |
| 7 | 429–442 | 14 | 266 | 0 |
| Total | | 79 13.8% | 1,501 | |

The location of the regions of the amino acid sequence of butyrylcholinesterase shown in Table 2 are shown in reference to the amino acid sequence of human butyrylcholinesterase (FIG. 2). The number of butyrylcholinesterase variants for each region reflects one variant for each of 19 amino acid substitutions at each position compared to human butyrylcholinesterase and a total library size of 1,501 variants. Species diversity indicates the number of positions within each region that have a naturally occurring amino acid difference compared to human butyrylcholinesterase.

Methods for preparing libraries containing diverse populations of various types of molecules such as peptides, peptoids and peptidoinimetics are well known in the art (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861, and Gordon et al., *J. Med. Chem.* 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide chemistry are well known in the art.

A library of butyrylcholinesterase variants can be produced, for example, by constructing a nucleic acid expression library encoding butyrylcholinesterase variants. Methods for producing such libraries are well known in the art (see, for example, Sambrook et al., *Molecular Cloning: A Laboratory Manual* (Cold Spring Harbor Laboratory Press 1989), which is incorporated herein by reference). A library of nucleic acids encoding butyrylcholinesterase variants can be composed of DNA, RNA or analogs thereof. A library containing RNA molecules can be constructed, for example, by synthesizing the RNA molecules chemically.

The invention further provides seven distinct libraries of nucleic acids encoding butyrylcholinesterase variants, each nucleic acid having at least one codon encoding at least one amino acid alteration in a region of butyrylcholinesterase corresponding to amino acid positions 68–82 (SEQ ID NO: 9), 110–121 (SEQ ID NO: 10), 194–201 (SEQ ID NO: 11), 224–234 (SEQ ID NO: 12), 277–289 (SEQ ID NO: 13), 327–332 (SEQ ID NO: 14) or 429–442 (SEQ ID NO: 15) of butyrylcholinesterase, respectively.

The generation of a library of nucleic acids encoding butyrylcholinesterase variants can be by any means desired by the user. Those skilled in the art will know what methods can be used to generate libraries of nucleic acids encoding butyrylcholinesterase variants. For example, butyrylcholinesterase variants can be generated by mutagenesis of nucleic acids encoding butyrylcholinesterase using methods well known to those skilled in the art (*Molecular Cloning: A Laboratory Manual*, Sambrook et al; eds; Cold Spring Harbor Press, Plainview, N.Y. (1989)). A library of nucleic acids encoding butyrylcholinesterase variants of the invention can be randomized to be sufficiently diverse to contain nucleic acids encoding every possible naturally occurring amino acid at each amino acid position of butyrylcholinesterase. Alternatively, a library of nucleic acids can be prepared such tat it contains nucleic acids encoding every possible naturally occurring amino acid at each amino acid only at positions located within a region of butyrylcholinesterase predicted or determined to be important for cocaine hydrolysis activity.

One or more mutations can be introduced into a nucleic acid molecule encoding a butyrylcholinesterase variant to yield a modified nucleic acid molecule using, for example, site-directed mutagenesis (see Wu (Ed.), *Meth. In Enzymol.* Vol. 217, San Diego: Academic Press (1993); Higuchi, "Recombinant PCR" in Innis et al. (Ed.), *PCR Protocols,* San Diego: Academic Press, Inc. (1990), each of which is incorporated herein by reference). Such mutagenesis can be used to introduce a specific, desired amino acid alteration. Thus, distinct libraries containing amino acid alterations in one or more of the regions determined to be important for cocaine hydrolysis activity as well as a single library containing mutations in several or all of the regions can be prepared.

The efficient synthesis and expression of libraries of butyrylcholinesterase variants using oligonucleotide-directed mutagenesis can be accomplished as previously described by Wu et al., *Proc. Natl. Acad. Sci. USA,* 95:6037–6042 (1998); Wu et al., *J. Mol. Biol.,* 294:151–162 (1999); and Kunkel, *Proc. Natl. Acad. Sci. USA,* 82:488–492 (1985), which are incorporated herein by reference. Oligonucleotide-directed mutagenesis is a well-known and efficient procedure for systematically introducing mutations, independent of their phenotype and is, therefore, ideally suited for directed evolution approaches to protein engineering. To perform oligonucleotide-directed mutagenesis a library of nucleic acids encoding the desired mutations is hybridized to single-stranded uracil-containing template of the wild-type sequence. The methodology is flexible, permitting precise mutations to be introduced without the use of restriction enzymes, and is relatively inexpensive if oligonucleotides are synthesized using codon-based mutagenesis.

Codon-based synthesis or mutagenesis represents one method well known in the art for avoiding genetic redundancy while rapidly and efficiently producing a large number of alterations in a known amino acid sequence or for generating a diverse population of random sequences. This method is the subject matter of U.S. Pat. Nos. 5,264,563 and 5,523,388 and is also described in Glaser et al. *J. Immunology* 149:3903–3913 (1992). Briefly, coupling reactions for the randomization of, for example, all twenty codons which specify the amino acids of the genetic code are performed in separate reaction vessels and randomization for a particular codon position occurs by mixing the products of each of the reaction vessels. Following mixing, the randomized reaction products corresponding to codons encoding an equal mixture of all twenty amino acids are then divided into separate reaction vessels for the synthesis of each randomized codon at the next position. If desired, equal frequencies of all twenty amino acids can be achieved with twenty vessels that contain equal portions of the twenty codons. Thus, it is possible to utilize this method to generate random libraries of the entire sequence of butyrylcholinesterase or focused libraries of the regions determined or predicted to be important for cocaine hydrolysis activity.

Variations to the above synthesis method also exist and include, for example, the synthesis of predetermined codons at desired positions and the biased synthesis of a predetermined sequence at one or more codon positions as described by Wu et al, supra, 1998. Biased synthesis involves the use of two reaction vessels where the predetermined or parent codon is synthesized in one vessel and the random codon sequence is synthesized in the second vessel. The second vessel can be divided into multiple reaction vessels such as that described above for the synthesis of codons specifying totally random amino acids at a particular position. Alternatively, a population of degenerate codons can be synthesized in the second reaction vessel such as through the coupling of NNG/T nucleotides or NNX/X where N is a mixture of all four nucleotides. Following synthesis of the predetermined and random codons, the reaction products in each of the two reaction vessels are mixed and then redivided into an additional two vessels for synthesis at the next codon position.

A modification to the above-described codon-based synthesis for producing a diverse number of variant sequences can similarly be employed for the production of the libraries of butyrylcholinesterase variants described herein. This modification is based on the two vessel method described above which biases synthesis toward the parent sequence and allows the user to separate the variants into populations containing a specified number of codon positions that have random codon changes.

Briefly, this synthesis is performed by continuing to divide the reaction vessels after the synthesis of each codon position into two new vessels. After the division, the reaction products from each consecutive pair of reaction vessels, starting with the second vessel, is mixed. This mixing brings together the reaction products having the same number of codon positions with random changes. Synthesis proceeds by then dividing the products of the first and last vessel and the newly mixed products from each consecutive pair of reaction vessels and redividing into two new vessels. In one of the new vessels, the parent codon is synthesized and in the second vessel, the random codon is synthesized. For example, synthesis at the first codon position entails synthesis of the parent codon in one reaction vessel and synthesis of a random codon in the second reaction vessel. For synthesis at the second codon position, each of the first two reaction vessels is divided into two vessels yielding two pairs of vessels. For each pair, a parent codon is synthesized in one of the vessels and a random codon is synthesized in the second vessel. When arranged linearly, the reaction products in the second and third vessels are mixed to bring together those products having random codon sequences at single codon positions. This mixing also reduces the product populations to three, which are the starting populations for the next round of synthesis. Similarly, for the third, fourth and each remaining position, each reaction product population for the preceding position are divided and a parent and random codon synthesized.

Following the above modification of codon-based synthesis, populations containing random codon changes at one, two, three and four positions as well as others can be conveniently separated out and used based on the need of the individual. Moreover, this synthesis scheme also allows enrichment of the populations for the randomized sequences over the parent sequence since the vessel containing only the parent sequence synthesis is similarly separated out from the random codon synthesis. This method can be used to synthesize a library of nucleic acids encoding butyrylcholinesterase variants having amino acid alterations in one or more regions of butyrylcholinesterase predicted to be important for cocaine hydrolysis activity.

Alternatively, a library of nucleic acids encoding butyrylcholinesterase variants can also be generated using gene shuffling. Gene shuffling or DNA shuffling is a method for directed evolution that generates diversity by recombination (see, for example, Stemmer, *Proc. Natl. Acad. Sci. USA* 91:10747–10751 (1994); Stemmer, *Nature* 370:389–391 (1994); Crameri et al., *Nature* 391:288–291 (1998); Stemmer et al., U.S. Pat. No. 5,830,721, issued Nov. 3, 1998). Gene shuffling or DNA shuffling is a method using in vitro homologous recombination of pools of selected mutant genes. For example, a pool of point mutants of a particular gene can be used. The genes are randomly fragmented, for example, using DNase, and reassembled by PCR. If desired, DNA shuffling can be carried out using homologous genes from different organisms to generate diversity (Crameri et al., supra, 1998). The fragmentation and reassembly can be carried out in multiple rounds, if desired. The resulting reassembled genes constitute a library of butyrylcholinesterase variants that can be used in the invention compositions and methods.

Thus, the invention also provides a library of nucleic acids encoding butyrylcholinesterase variants, each nucleic acid having at least one codon encoding at least one amino acid alteration in one or more regions of butyrylcholinesterase corresponding to amino acid positions 68–82 (SEQ ID NO: 9), 110–121 (SEQ ID NO: 10), 194–201 (SEQ ID NO: 11), 224–234 (SEQ ID NO: 12), 277–289 (SEQ ID NO: 13), 327–332 (SEQ ID NO: 14) or 429–442 (SEQ ID NO: 15) of butyrylcholinesterase, wherein at least one of the nucleic acids encodes a butyrylcholinesterase variant having enhanced cocaine hydrolysis activity compared to butyrylcholinesterase, with the proviso that a butyrylcholinesterase variant having a single amino acid alteration is not the human butyrylcholinesterase having Y at position 328.

The invention library of nucleic acids encoding butyrylcholinesterase variants can be expressed in a variety of eukaryotic cells. For example, the nucleic acids can be expressed in mammalian cells, insect cells, plant cells, and non-yeast fungal cells. Mammalian cell lines useful for expressing the invention library of nucleic acids encoding butyrylcholinesterase variants include, for example, Chinese Hamster Ovary (CHO), human T293 and Human NIH 3T3 cell lines. Expression of the invention library of nucleic acids encoding butyrylcholinesterase variants can be achieved by both stable or transient cell transfection (see Example III, Table 5).

The incorporation of variant nucleic acids or heterologous nucleic acid fragments at an identical site in the genome functions to create isogenic cell lines that differ only in the expression of a particular variant or heterologous nucleic acid. Incorporation at a single site minimizes positional effects from integration at multiple sites in a genome that affect transcription of the mRNA encoded by the nucleic acid and complications from the incorporation of multiple copies or expression of more than one nucleic acid species per cell. Techniques known in the art that can be used to target a variant or a heterologous nucleic acid to a specific location in the genome include, for example, homologous recombination, retroviral targeting and recombinase-mediated targeting.

One approach for targeting variant or heterologous nucleic acids to a single site in the genome uses Cre recombinase to target insertion of exogenous DNA into the eukaryotic genome at a site containing a site specific recombination sequence (Sauer and Henderson, Proc. Natl. Acad. Sci. USA, 85:5166–5170 (1988); Fukushige and Sauer, Proc. Natl. Acad. Sci. U.S.A. 89:7905–7909 (1992); Bethke and Sauer, Nuc. Acids Res., 25:2828–2834 (1997)). In addition to Cre recombinase, Flp recombinase can also be used to target insertion of exogenous DNA into a particular site in the genome (Dymecki, Proc. Nati. Acad. Sci. U.S.A. 93:6191–6196 (1996)). The target site for Fip recombinase consists of 13 base-pair repeats separated by an 8 base-pair spacer: 5'-GAAGTTCCTATTC [TCTAGAAA]GTATAG-GAACTTC-3' (SEQ ID NO: 24). As described herein, the butyrylcholinesterases designated SEQ ID NOS: 4, 6, and 8, were obtained by transfection of variant libraries corresponding to region 5 of human butyrylcholinesterase (see, Table 2) into mammalian cells using Flp recombinase and the human 293T cell line. It is understood that any combination of site-specific recombinase and corresponding recombination site can be used in methods of the invention to target a nucleic acid to a particular site in the genome.

A suitable recombinase can be encoded on a vector that is co-transfected with a vector containing a nucleic acid encoding a butyrylcholinesterase variant. Alternatively, the expression element of a recombinase can be incorporated into the same vector expressing a nucleic acid encoding a butyrylcholinesterase variant. In addition to simultaneously transfecting the nucleic acid encoding a recombinase with the nucleic acids encoding a butyrylcholinesterase variant, a vector encoding the recombinase can be transfected into a cell, and the cells can be selected for expression of recombinase. A cell stably expressing the recombinase can subsequently be transfected with nucleic acids encoding variant nucleic acids.

As disclosed herein, the precise site-specific DNA recombination mediated by Cre recombinase can be used to create stable mammalian transformants containing a single copy of exogenous DNA encoding a butyrylcholinesterase variant. As exemplified below, the frequency of Cre-mediated targeting events can be enhanced substantially using a modified doublelox strategy. The doublelox strategy is based on the observation that certain nucleotide changes within the core region of the lox site alter the site selection specificity of Cre-mediated recombination with little effect on the efficiency of recombination (Hoess et al., *Nucleic Acids Res.* 14:2287–2300 (1986)). Incorporation of loxP and an altered loxP site, termed lox511, in both the targeting vector and the host cell genome results in site-specific recombination by a double crossover event. The doublelox approach increases the recovery of site-specific integrants by 20-fold over the single crossover insertional recombination, increasing the absolute frequency of site-specific recombination such that it exceeds the frequency of illegitimate recombination (Bethke and Sauer, *Nuc. Acids Res.,* 25:2828–2834 (1997)).

Following the expression of a library of butyrylcholinesterase variants in a mammalian cell line, randomly selected clones can be sequenced and screened for increased cocaine hydrolysis activity. Methods for sequencing selected clones are well known to those of skill in the art and are described, for example, in Sambrook et al., supra, 1992, and in Ausubel et al; supra, 1998. Selecting a suitable method for measuring the cocaine hydrolysis activity of a butyrylcholinesterase variant depends on a variety of factors such as, for example, the amount of the butyrylcholinesterase variant that is available. The cocaine hydrolysis activity of a butyrylcholinesterase variant can be measured, for example, by spectrophotometry, by a microtiter-based assay utilizing a polyclonal anti-butyrylcholinesterase antibody to uniformly capture the butryrylcholinesterase variants and by high-performance liquid chromatography (HPLC).

Enhanced cocaine hydrolysis activity of a butyrylcholinesterase variant compared to butyrylcholinesterase can be determined by a comparison of catalytic efficiencies as described in Example I. Clones expressing butyrylcholinesterase variants exhibiting increased cocaine hydrolysis activity are sequenced to reveal the precise location and nature of the mutation. To ensure that a library of butyrylcholinesterase variants has been screened exhaustively, screening of each library can be continued until clones encoding identical butyrylcholinesterase amino acid alterations have been identified on multiple occasions.

Clones expressing a butyrylcholinesterase variant with increased cocaine hydrolysis activity can be used to establish larger-scale cultures suitable for purifying larger quantities of the butyrylcholinesterase. A butyrylcholinesterase variant of interest can be cloned into an expression vector and used to transfect a cell line, which can subsequently be expanded. Those skilled in the art will know what type of expression vector is suitable for a particular application. A butyrylcholinesterase variant exhibiting increased cocaine hydrolysis activity can be cloned, for example, into an expression vector carrying a gene that confers resistance to a particular chemical agent to allow positive selection of the transfected cells. An expression vector suitable for transfection of, for example, mammalian cell lines can contain a promoter such as the cytomegaloviras (CMV) promoter for selection in mammalian cells. As described herein, a butyrylcholinesterase variant can be cloned into a mammalian expression vector and transfected into Chinese Hamster Ovary cells (CHO). Expression vectors suitable for expressing a butyrylcholinesterase variant are well known in the art and commercially available.

Clones expressing butyrylcholinesterase variants can be selected and tested for cocaine hydrolysis activity. Cells carrying clones exhibiting enhanced cocaine hydrolysis activity can be expanded by routine cell culture systems to produce larger quantities of a butyrylcholinesterase variant of interest. The concentrated recombinant butyrylcholinesterase variant can be harvested and purified by methods well known in the art and described, for example, by Masson et al., Biochemistry 36: 2266–2277 (1997), which is incorporated herein by reference.

A butyrylcholinesterase variant exhibiting increased cocaine hydrolysis activity in vitro can be utilized for the treatment of cocaine toxicity and addiction in vivo. The potency for treating cocaine toxicity of a butyrylcholinesterase variant exhibiting increased cocaine hydrolysis activity in vitro can be tested using an acute overdose animal model as disclosed herein (see Example VII). In addition, animal models of reinforcement and discrimination are used to predict the efficacy of a butyrylcholinesterase variant for treatment of cocaine addiction as disclosed below (see Example VII). Suitable animal subjects for overdose as well as reinforcement and discrimination models are known in the art and include, for example, rodent and primate models. A butyrylcholinesterase variant effective in reducing either cocaine toxicity or cocaine addiction in one or more animal models can be used to treat a cocaine-induced condition by administering an effective amount of the butyrylcholinesterase variant to an individual.

A butyrylcholinesterase variant having an increased serum half-life can be useful for testing a butyrylcholinesterase variant in a subject or treating a cocaine-induced condition in an individual. Useful methods for increasing the serum half-life of a butyrylcholinesterase variant include, for example, conversion of the butyrylcholinesterase variant into a tetramer, covalently attaching synthetic and natural polymers such as polyethylene glycol (PEG) and dextrans to the truncated butyrylcholinesterase variant, liposome formulations, or expression of the enzyme as an Ig-fusion protein. As disclosed herein, conversion of a butyrylcholineserase variant into a tetramer can be achieved by co-transfecting the host cell line with the COLQ gene (Example I) as well as by addition of poly-L-proline to the media of transfected cells. These and other methods known in the art for increasing the serum half-life of a butyrylcholinesterase variant are useful for testing a butyrylcholinesterase variant in an animal subject or treating a cocaine-induced condition in an individual.

The invention also provides a method of hydrolyzing a cocaine-based butyrylcholinesterase substrate comprising contacting a butyrylcholinesterase substrate with the butyrylcholinesterase variant shown as SEQ ID NO: 2 under conditions that allow hydrolysis of cocaine into metabolites, wherein the butyrylcholinesterase variant exhibits a five-fold or more increase in cocaine hydrolysis activity compared to butyrylcholinesterase. In addition, the invention provides a method of treating a cocaine-induced condition comprising administering to an individual an effective amount of a butyrylcholinesterase variant (SEQ ID NO: 2) exhibiting increased cocaine hydrolysis activity compared to butyrylcholinesterase.

The invention further provides a method of hydrolyzing a cocaine-based butyrylcholinesterase substrate comprising contacting a butyrylcholinesterase substrate with a butyrylcholinesterase variant selected from the group shown as SEQ ID NO: 4, SEQ ID NO: 6 and SEQ ID NO: 8, under conditions that allow hydrolysis of cocaine into metabolites, wherein the butyrylcholinesterase variant exhibits a two-fold or more increase in cocaine hydrolysis activity compared to butyrylcholinesterase. In addition, the invention provides a method of treating a cocaine-induced condition comprising administering to an individual an effective amount of a butyrylcholinesterase variant selected from the group shown as SEQ ID NO: 4, SEQ ID NO: 6 and SEQ ID NO: 8, exhibiting increased cocaine hydrolysis activity compared to butyrylcholinesterase.

As described herein, a butyrylcholinesterase variant exhibiting increased cocaine hydrolysis activity can hydrolyze a cocaine-based butyrylcholinesterase substrate in vitro as well as in vivo. A cocaine-based butyrylcbolinesterase substrate can be contacted wit a bntyrylcholinesterase variant of the invention in vitro, for example, by adding the substrate to supernatant isolated from cultures of buryryl-cholinesterase variant library clones. Alternatively, the butyrylcholinesterase variant can be purified prior to being contacted by the subsurate. Appropriate medium conditions in which to contact a cocaine-based substrate with a butyryl-cholinesterase variant of the invention are readily determined by those skilled in the art. For example, 100 µM cocaine in 10 mM Ths at pH 7.4 can be contacted with a butyrylcholinesterase variant at 37° C. As described below, butyrylcholinesterase variants from culture supernatants can further be immobilized using a capture agent, such as an antibody prior to being contacted with a substrate, which allows for removal of culture supernatant components and enables contacting of the immobilized variants with substrate in the absence of contaminants. Following contacting of a butyrylcholinesterase variant of the invention with a cocaine-based substrate, cocaine hydrolysis activity can be measured by a variety of methods known in the art and described herein, for example, by high-performance liquid chromatography or the isotope tracer cocaine hydrolysis assay.

The invention also provides a method of treating cocaine overdose as well as cocaine addiction in an individual by administering a therapeutically effective amount of the butyrylcholinesterase variant. The dosage of a butyrylcho-linesterase variant required to be effective depends, for example, on whether an acute overdose or chronic addiction is being treated, the route and form of administration, the potency and bio-active half-life of the molecule being administered, the weight and condition of the individual, and previous or concurrent therapies. The appropriate amount considered to be an effective dose for a particular application of the method can be determined by those skilled in the art, using the teachings and guidance provided herein. For example, the amount can be extrapolated from in vitro or in vivo butyrylcholinesterase assays described herein. One skilled in the art will recognize that the condition of the individual needs to be monitored throughout the course of treatment and that the amount of the composition that is administered can be adjusted accordingly.

For treating cocaine-overdose, a therapeutically effective amount of a butyrylcholinesterase variant of the invention can be, for example, between about 0.1 mg/kg to 0.15 mg/kg body weight, for example, between about 0.15 mg/kg to 0.3 mg/kg, between about 0.3 mg/kg to 0.5 mg/kg or preferably between about 1 mg/kg to 5 mg/kg, depending on the treatment regimen. For example, if a butyrylcholinesterase variant is administered to an individual symptomatic of cocaine overdose a higher one-time dose is appropriate, while an individual symptomatic of chronic cocaine addiction may be administered lower doses from one to several times a day, weekly, monthly or less frequently. Similarly, formulations that allow for timed-release of a butyrylcho-linesterase variant would provide for the continuous release of a smaller amount of a butyrylcholinesterase variant to an individual treated for chronic cocaine addiction. It is understood, that the dosage of a butyrylcholinesterase variant has to be adjusted based on the catalytic activity of the variant, such that a lower dose of a variant exhibiting significantly enhanced cocaine hydrolysis activity can be administered compared to the dosage necessary for a variant with lower cocaine hydrolysis activity.

A butyrylcholinesterase variant can be delivered systemically, such as intravenously or intraarterially. A butyrylcho-linesterase variant can be provided in the form of isolated and substantially purified polypeptides and polypeptide fragments in pharmaceutically acceptable formulations using formulation methods known to those of ordinary skill in the art. These formulations can be administered by standard routes, including for example, topical, transdermal, intraperitoneal, intracranial, intracerebroventricular, intrac-erebral, intravaginal, intrauterine, oral, rectal or parenteral (e.g., intravenous, intraspinal, subcutaneous or intramuscular) routes. In addition, a butyrylcholinesterase variant can be incorporated into biodegradable polymers allowing for sustained release of the compound useful for treating individuals symptomatic of cocaine addiction. Biodegradable polymers and their use are described, for example, in detail in Brem et al., *Neurosurg.* 74:441–446 (1991), which is incorporated herein by reference.

A butyrylcholinesterase variant can be administered as a solution or suspension together with a pharmaceutically acceptable medium. Such a pharmaceutically acceptable medium can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable medium can additionally contain physiologically acceptable compounds that act, for example, to stabilize or increase the absorption of the butyrylcholinesterase variant. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients.

Formulations suitable for parenteral administration include aqueous and non-aqueous sterile injection solutions such as the pharmaceutically acceptable mediums described above. The solutions can additionally contain, for example, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

The butyrylcholinesterase variant of the invention can further be utilized in combination therapies with other therapeutic agents. Combination therapies that include a butyrylcholinesterase variant can consist of formulations containing the variant and the additional therapeutic agent individually in a suitable formulation. Alternatively, combination therapies can consist of fusion proteins, where the butyrylcholinesterase variant is linked to a heterologous protein, such as a therapeutic protein.

The butyrylcholinesterase variant of the invention also can be delivered to an individual by administering an encoding nucleic acid for the peptide or variant. The encoding nucleic acids for the butyrylcholinesterase variant of the invention are useful in conjunction with a wide variety of gene therapy methods known in the art for delivering a therapeutically effective amount of the polypeptide or variant. Using the teachings and guidance provided herein, encoding nucleic acids for a butyrylcholinesterase variant can be incorporated into a vector or delivery system known in the art and used for delivery and expression of the encoding sequence to achieve a therapeutically effective amount. Applicable vector and delivery systems known in the art include, for example, retroviral vectors, adenovirus vectors, adenoassociated virus, ligand conjugated particles and nucleic acids for targeting, isolated DNA and RNA, liposomes, polylysine, and cell therapy, including hepatic cell therapy, employing the transplantation of cells modified to express a butyrylcholinesterase variant, as well as various other gene delivery methods and modifications known to those skilled in the art, such as those described in Shea et al., *Nature Biotechnology* 17:551–554 (1999), which is incorporated herein by reference.

Specific examples of methods for the delivery of a butyrylcholinesterase variant by expressing the encoding nucleic acid sequence are well known in art and described in, for example, U.S. Pat. No. 5,399,346; U.S. Pat. Nos. 5,580,859; 5,589,466; 5,460,959; 5,656,465; 5,643,578; 5,620,896; 5,460,959; 5,506,125; European Patent Application No. EP 0 779 365 A2; PCT No. WO 97/10343; PCT No. WO 97/09441; PCT No. WO 97/10343, all of which are incorporated herein by reference. Other methods known to those skilled in the art also exist and are similarly applicable for the delivery of a butyrylcholinesterase variant by expressing the encoding nucleic acid sequence.

In addition to the treatment of cocaine-induced conditions such as cocaine overdose or cocaine addiction, a butyrylcholinesterase can also be administered prophylactically to avoid the onset of a cocaine overdose upon subsequent entry of cocaine into the bloodstream. It is further contemplated that a butyrylcholinesterase variant exhibiting increased cocaine hydrolysis activity of the invention can have diagnostic value by providing a tool for efficiently determining the presence and amount of a cocaine-induced substance in a medium.

It is understood that modifications that do not substantially affect the activity of the various embodiments of this invention are also included within the definition of the invention provided herein. Accordingly, the following examples are intended to illustrate but not limit the present invention.

EXAMPLE I

A Butyrylcholinesterase Variant with Increased Cocaine Hydrolysis Activity

This example describes the discovery and characterization of the butyrylcholinesterase variant designated SEQ ID NO: 2, in which Alanine (A) at amino acid position 328 of human butyrylcholinesterase is replaced with Tryptophan (W). The A328W butyrylcholinesterase variant designated SEQ ID NO: 2 exhibits a 15-fold increase in cocaine hydrolysis activity compared to human butyrylcholinesterase.

Structural Modeling of Cocaine in the Active Site of Human Butyrylcholinesterase In order to determine amino acid residues important for cocaine hydrolysis activity, cocaine was docked into the active site of butyrylcholinesterase with the FlexiDock program (Tripos Inc., St. Louis, Mo.) in Sybyl 6.4 software on a Silicone Graphics Octane computer. Flexidock allows docking of ligands into protein active sites, allowing the user to define bonds which are flexible during the docking process. The user must identify the starting conformation and position the interacting faces of the protein-ligand.

The structures of (−)-cocaine and (+)-cocaine were retrieved from the Cambridge Structural Database where its code-names are COCAIN10 and COCHCL. The HCl molecule was deleted from COCHCL so that all computations were done with the base form of cocaine. Before the FlexiDock program was run, cocaine was manually aligned with butyrylcholine in the model of human butyrylcholinesterase as described by Harel et al., *Proc. Natl. Acad. Sci. USA*, 89: 10827–10831 (1992). Manual alignment was performed so that the tropane ring of cocaine faced the Tryptophan residue (W) at amino acid position 82 of butyrylcholinesteflse, the carboxyl group of the benzoic ester of cocaine was within 1.5 Å of the Serine (S) residue at amino acid position 198 of butyrylcholinesterase, and the benzene ring of cocaine was in the acyl binding pocket of butyrylcholinesterase. In the FlexiDock the binding pocket was defined as all amino acids within 4 Å of butyrylcholine. After defining the binding pocket, the butyrylcholine molecule was extracted. All atoms in the binding pocket, except atoms in rings and double bonded atoms, were defined as rotatable, thus yielding 124 rotatable bonds in butyrylcholinesterase and 7 rotatable bonds in cocaine.

Mutagenesis of Human Butyrylcholinesterase and Expression of a Butyrylcholinesterase Variant.

Based on the FlexiDock modeling of cocaine into the active site of the human butyrylcholinesterase molecule, amino acids that interfere with binding were selected for mutagenesis.

Thirty-four variants were prepared using PCR-site directed mutagenesis of human butyrylcholinesterase DNA performed utilizing Pfu polymerase (Stratagene, La Jolla, Calif.). Three oligonucleotide primers were used to perform the mutagenesis. The mutagenesis primers were used at the same time as a general primer such as the SP6 promoter sequencing primer (MBI Fermentas, Amherst, N.Y.) to amplify one end of the butyryicholinesterase cDNA. The following primers were used to prepare the A328W mutant: A328W antisense 5'ATAGACTAAAAACCATGTCCCTTCATC 3' (SEQ ID NO: 29); T7 old sense 5'TAATACGACTCACTATAGGG 3' (SEQ ID NO: 30); and SP6 antisense 5'ATTTAGGTGACACTATAG 3' (SEQ ID NO: 31). The A328W primer spans 27 nucleotides and contains the A328W mutation in the middle of the primer. The PCR reaction products (megaprimers) were cleaned on QuiaQuick PCR (Qiagen, Santa Clarita, Calif.) according to the manufacturer's protocol to remove excess primers. The cleaned megaprimers were extended in a second 2CR reaction to generate the complete 1.8 kb coding sequence of each of the 34 variants.

The 1.8-kb fragments constituting the butyrylcholinesterase variants were cloned into the plasmid pGS and resequenced to make sure the desired mutation was present. The plasmid pGS is identical with pRc/CMV (Invitrogen, Carlsbad, Calif.) except that the Neo gene has been replaced by rat glutamine synthetase.

To express the thirty-four butyrylcholinesterase variants in mammalian cell lines, thirty-four stable Chinese Hamster Ovary (CHO) cell lines expressing a butyrylcholinesterase variant were made. Transfection of CHO-KI (No. CCL 61; American Type; Fisher Scientific Co., Pittsburgh, Pa.) cells by calcium phosphate precipitation was followed by selection of colonies in glutamine-free, serum-free medium Ultraculture containing 50 μM methionine sulfoximine (BioWhittaker, Inc., Walkersville, Md.). Colonies expressing the highest levels of butyrylcholinesterase activity were expanded. A second plasmid that carries the COLQ gene, which encodes the proline rich attachment domain, was transfected into each of the CHO-KI cell lines to allow butyrylcholinesterase to form tetramers, which are more stable.

The secreted butyrylcholinesterase variants were collected from the expanded cell lines. For collection of large volumes of each secreted butyrylcholinesterase variant, cells in 1-liter roller bottles were fed every 2 to 3 days with 100 ml of Ultraculture containing 25 μM methionine sulfoximine followed by 100 ml of Dulbecco's modified Eagle's medium and Ham's F12 50:50 mix without L-glutamine (Mediatech, Herndon, Va.; Fisher Scientific Co., Pittsburgh, Pa.). The amount of secreted butyrylcholinesterase variant is about 1 mg per liter. Twenty liters of culture medium were collected for each of the thirty-four variants over a period of months and stored sterile at 4° C. during the collection period.

Purification and Characterization of the Butyrylcholinesterase Variants

To purify the butyrylcholinesterase variants, the culture medium corresponding to each variant was filtered through Whatman #1 filter paper (Whatman Inc., Clifton, N.J.) on a Buchner funnel. The filtrate was poured through a chromatography column (XK50/30, Pharmacia Biotech, Piscataway, N.J.) packed with 100ml of affinity gel procainamide-Sepharose 4B. The butyrylcholinesterase variants stick to the affinity gel during loading so that 20 mg of enzyme that was previously in 20 liters was concentrated in 100 ml of affinity gel. The affinity gel was subsequently washed with 3M sodium chloride in 20 mM potassium phosphate pH 7.0 and 1 mM EDTA to elate contaminating proteins. Next the affinity gel was washed with buffer containing 20 mM potassium phosphate and 1 mM EDTA pH 7.0 to reduce the ionic strength. Finally, the butyrylcholinesterase variants were eluted with 250 ml of 0.2M procainamide in buffer.

To further purify the butyrylcholinesterase variants and remove the procainamide a second purification step was performed. The butyrylcholinesterase variants recovered in the first purification step were diluted 10-fold with buffer (20 mM TrisCl, 1 mM EDTA pH 7.4) to reduce the ionic strength to about 0.02M. The diluted enzyme was loaded onto a column containing 400 ml of the weak anion exchanger DE52 (Whatman, Clifton, N.J.). At this low ionic strength the butyrylcholinesterase variant sticks to the ion exchange gel. After loading was complete the column was washed with 2 liters of buffer containing 20 mM TrisCl and 1 mM EDTA pH 7.4 until the absorbency of the eluant at 280 nm was nearly zero, indicating that the procainamide had washed off. Subsequently, the butyrylcholinesterase variants were eluted from the column with a salt gradient from 0 to 0.2M NaCl in 20 mM TrisCl pH7.4. Following the elution of the butyrylcholinesterase variants 10 ml fractions were collected for each variant using a fraction collector. Activity assays were performed to identify the peak containing butyrylcholinesterase variant SDS gel electrophoresis was performed to determine the purity of each butyrylcholinesterase variant, which was determined to be approximately 90%.

The thirty-four purified butyrylcholinestesterase variants were assayed for their ability to hydrolyze cocaine. The assay measured the affinity of (−)-cocaine for the butyrylcholinesterase variants and the maximal rate of hydrolysis of (−)-cocaine for each variant. Enzyme-catalyzed hydrolysis of cocaine was recorded on a temperature-equilibrated Gilford Spectrophotometer at 240 nm where the difference in molar absorptivity between substrate and product was ΔE=6,700$M^{-1}$ $cm^{-1}$ as described by Gatley, *Biochem. Pharmacol.* 41:1249–1254 (1991). $K_m$ values were determined in 0.1M potassium phosphate pH 7.0 at 30° C. for (−)-cocaine. $V_{max}$ values and $K_m$ values were calculated using Sigma Plot for Macintosh (Jandel Scientific, San Rafael, Calif.).

Once $V_{max}$ values and $K_m$ values were calculated, the number of active sites in each butyrylcholinesterase preparation was determined. The titration of active sites was performed with chlorpyrifos oxon (MET-674B, Chem Service, West Chester, Pa.), an inhibitor of butyrylcholinesterase. One molecule of chlorpyrifos oxon binds and inhibits one molecule of butyrylcholinesterase, which allows for calculation of the number of active sites. Based on the number of active sites, the $k_{cat}$ value for each variant was calculated (Table 3). Thirty-four variants were tested for cocaine binding or cocaine hydrolysis (Table 4). One variant, A328W, was determined to have 15 times faster cocaine hydrolysis activity compared to wild-type butyrylcholinesterase.

TABLE 3

Binding constant ($K_i$ and $K_m$) and hydrolysis rate ($k_{cat}$) for human butyrylcholinesterase and mutants

| | $K_i$ (µM) | $K_m$ (µM) | $k_{cat}$ (min$^{-1}$) |
|---|---|---|---|
| wild-type | 11 | 14 | 3.9 |
| D70G | 201 | | |
| D70N | 490 | | |
| G117H | 440 | | |
| G117K | 300 | | |
| Q119H | 34 | | |
| Q119Y | | 56 | 2.0 |
| T120F | | 97 | |
| E197D | 40 | | |
| E197G | 37 | | |
| E197Q | | 17 | 0.1 |
| L286A | 8.5 | | |
| L286H | 24 | | |
| V288F | | 17 | 1.0 |
| V288H | 55 | | |
| A328F | 21 | 24 | 5.8 |
| A328G | 18 | | |
| A328H | 27 | | |
| A328I | | 11 | 0.5 |
| A328W | | 10 | 37.2 |
| A328Y | | 9 | 10.2 |
| F329A | | 128 | 2.7 |
| F329S | | 41 | 1.9 |
| Y332A | | 240 | |
| Y332F | 22 | | |
| G439A | 7 | | |
| N68Y/Q119Y/A277W | | 60 | 1.7 |
| Q119Y/V288F/A328Y | | 33 | 2.3 |

TABLE 4

Mutants tested for cocaine binding or hydrolysis (34 plus wild-type)

| Mutant | Cocaine Binding or Cocaine Hydrolysis |
|---|---|
| wild-type | Ki = 11 µM |
| D70G | Ki = 201 µM |
| D70N | Ki = 490 µM |
| G115A | no activity |
| G116F | no activity |
| G116W | no activity |
| G117H | Ki = 440 µM |
| Q119H | Ki = 34 µM |
| Q119Y | not a cocaine hydrolase |
| T120F | not a cocaine hydrolase |
| E197D | Ki = 40 µM |
| E197G | Ki = 37 µM |
| E197Q | Not a cocaine hydrolase |
| S224Y | No activity |
| L286A | Ki = 24 µM |
| L286H | Not a cocaine hydrolase |
| L286W | Not a cocaine hydrolase |
| V288F | Not a cocaine hydrolase |
| V288H | Ki = 55 µM |
| V288W | Not a cocaine hydrolase |
| A328F | Not a cocaine hydrolase |
| A328G | Not a cocaine hydrolase |
| A328H | Not a cocaine hydrolase |
| A328I | Not a cocaine hydrolase |
| A328W | Hydrolyzes cocaine 15 times faster than wild-type |
| A328Y | Hydrolyzes cocaine 4 times faster than wild-type |
| F329A | Not a cocaine hydrolase |
| F329S | kcat is faster than wild type |
| Y332F | Ki = 22 µM |
| G439A | Ki = 7 µM |

TABLE 4-continued

Mutants tested for cocaine binding or hydrolysis (34 plus wild-type)

| Mutant | Cocaine Binding or Cocaine Hydrolysis |
|---|---|
| G439L | No cocaine hydrolysis activity |
| N68Y/Q119Y/A277W | Not a cocaine hydrolase |
| Q119Y/V288F/A328Y | Not a cocaine hydrolase |

EXAMPLE II

Development of a Cocaine Hydrolysis Assay

This example describes the development of a cocaine hydrolysis assay that permits the efficient analysis of hundreds of butyrylcholinesterase variants simultaneously.

Development of an Isotope Tracer Cocaine Hydrolysis Assay.

For the purpose of validating new cocaine hydrolysis assays, butyrylcholinesterase hydrolysis of cocaine was first measured as described previously (Xie et al., *Mol. Pharmacol.* 55:83–91 (1999)), using high-performance liquid chromatography (HPLC). Briefly, reactions containing 100 µM cocaine in 10 mM Tris, pH 7.4 were initiated by the addition of horse butyrylcholinesterase (ICN Pharmaceuticals, Inc., Costa Mesa, Calif.) and incubated 2–4 hours at 37° C. Following the incubation, the pH was adjusted to 3, and the sample was filtered. Subsequently, the sample was applied to a Hypersil ODS-C 18 reversed phase column (Hewlett Packard, Wilmington, Del.) previously equilibrated with an 80:20 mixture of 0.05 M potassium phosphate, pH 3.0 and acetonitrile. The isocratic elution of cocaine, benzoylecognine, and benzoic acid was quantitated at 220 nm. Measurement of the formation of ecognine methyl ester and benzoic acid was dependent both on the amount of butyrylcholinesterase in the reaction and on the time of reaction.

At the conclusion of the isotope tracer assay, an aliquot of the reaction mix is acidified in order to take advantage of the solubility difference between the product and the substrate at pH 3.0. At pH 3.0, [3H]-benzoic acid (pKa=4.2) is soluble in a scintillation cocktail consisting of 2,5-diphenyloxazole (PPO) and [1,4-bis-2-(4-methyl-5-phenyloxazolyl)-benzene](POPOP) (PPO-dimethyl-POPOP scintillation fluor, Research Products International Corp., Mt. Prospect, Ill) while [3H]-cocaine is not. The signal generated by acidified reaction mixture from enzyme blanks was less than 2% of the total dpm placed in the fluor, consistent with cocaine being insoluble in PPO-dimethyl-POPOP.

Figure 5B:
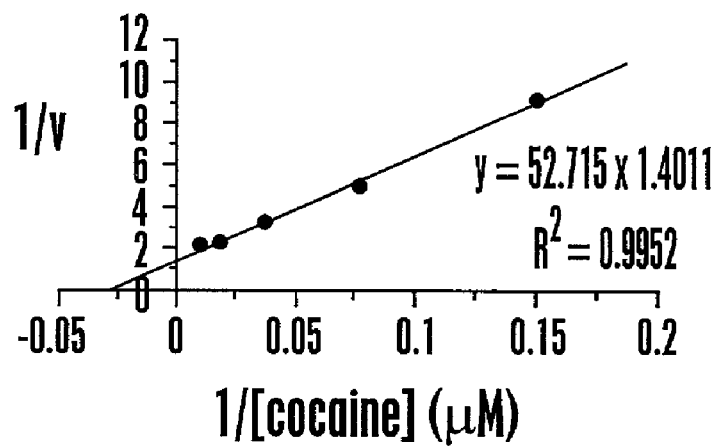

The isotope tracer cocaine hydrolysis assay was validated by direct comparison with the established HPLC assay and the accuracy of the isotope assay was demonstrated by determining the $K_m$ value for horse butyrylcholinesterase. The rate of cocaine hydrolysis, determined by measuring the rate of formation of benzoic acid was quantitated both by HPLC and the isotope tracer assay in reactions containing variable amounts of butyrylcholinesterase. Formation of [$^3$H]-benzoic acid was dependent on the length of assay incubation and on the amount of butyrylcholinesterase added. Good correlation between the established HPLC assay and the isotope tracer assay was observed, as demonstrated by plotting the quantitation of benzoic acid formation measured by HPLC versus the benzoic acid formation measured in the isotope assay (see FIG. 5A; r$^2$=0.979). To demonstrate the precision and sensitivity of the isotope assay the amount of cocaine was varied and the $K_m$ was determined using the Lineweaver-Burk double-reciprocal plot of cocaine hydrolysis by horse butyrylcholinesterase depicted in FIG. 5B. Velocity was calculated as cpm benzoic acid formed×$10^{-5}$ following a 2 hour incubation at 37° C. Based on these data the $K_m$ for cocaine hydrolysis is approximately 37.6 μM (×intercept=–1/$K_m$), which is in close agreement with previously published values of 38 μM (Gatley, supra, 1991) and 45±5 μM (Xie et al., supra, 1999) for horse butyrylcholinesterase.

Immobilization of Active Butyrylcholinesterase.

The supernatants isolated from each of the butyrylcholinesterase variant library clones contains variable butyrylcholinesterase enzyme concentrations. Consequently, the cocaine hydrolysis activity measured from equal volumes of culture supernatants from distinct butyrylcholinesterase variant clones reflects the expression level as well as the enzyme activity. In order to be able to compare equal enzyme concentrations and more rapidly identify variants with the desired activity, butyrylcholinesterase from culture supernatants are immobilized using a capture reagent, such as an antibody, that is saturated at low butyrylcholinesterase concentrations as described previously by Watkins et al., *Anal. Biochem.* 253: 37–45 (1997). As a result, butyrylcholinesterase from dilute samples is concentrated and uniform quantities of different butyrylcholinesterase variant clones are immobilized, regardless of the initial concentration of butyrylcholinesterase in the culture supernatant. Subsequently, unbound butyrylcholinesterase and other culture supernatant components that potentially interfere with the assay (such as unrelated serum or cell-derived proteins with significant esterase activity) are washed away and the activity of the immobilized butyrylcholinesterase is determined by measuring the formation of benzoic acid as described above.

To assess the efficiency of the above assay, efficient capture of human butyrylcholinesterase, as well as a truncated soluble monomeric form of human butyrylcholinesterase (Blong et al., *Biochem. J.* 327: 747–757 (1997)), was demonstrated in a microtiter format using a commercially available rabbit anti-human cholinesterase polyclonal antibody (DAKO, Carpinteria, Calif.) (FIG. 6). In order to determine the optimal conditions for capturing butyrylcholinesterase a microtiter plate was coated with increasing quantities of rabbit anti-butyrylcholinesterase, was blocked, and incubated with varying amounts of culture supernatant. The amount of active butyrylcholinesterase captured was determined calorimetrically using an assay that measures butyrylthiocholine hydrolysis at 405 nm in the presence of dithiobisnitrobenzoic acid (Xie et al., supra, 1999). Subsequently, the butyrylcholinesterase activity captured from dilutions of culture supernatants from cells expressing either the wild-type human butyrylcholinesterase or the monomeric truncated version was measured. The rabbit anti-butyrylcholinesterase capture antibody was saturated by the butyrylcholinesterase present in 25 μl of culture supernatant with greater butyrylcholinesterase activity being captured from supernatant containing the full length wild-type form of the enzyme (FIG. 6, compare filled circles with open circles). Unbound material was removed by washing with 100 mM Tris, pH 7.4 and the amount of active butyrylcholinesterase captured was quantitated by measuring butyrylthiocholine hydrolysis. Butyrylcholinesterase is expressed in culture supernatants at quantities sufficient to saturate a polyclonal anti-butyrylcholinesterase antibody on a microtiter plate. In addition, the captured enzyme is active, as demonstrated by the hydrolysis of butyrylthiocholine.

Measurement of Cocaine Hydrolysis with Isotope Tracer Assay and Immobilized Butyrylcholinesterase The optimal conditions for immobilization of active butyrylcholinesterase are used in conjunction with the cocaine isotope tracer assay to measure the cocaine hydrolysis activity in a microtiter format. The assay is characterized by determining the $K_m$ for cocaine hydrolysis activity, as described above. At least three approaches are used to either increase the assay sensitivity or the assay signal.

First, longer assay incubation times that proportionately increase the signal can be used. Second, the sensitivity of the assay can be enhanced by increasing the specific activity of the radiolabeled cocaine substrate. Third, a previously identified butyrylcholinesterase mutant which is 4-fold more efficient for cocaine hydrolysis can used (Xie et al., supra, 1999), which in conjunction with doubling the assay incubation time and increasing the specific activity of the cocaine 10-fold, can increase the assay signal about 80-fold.

EXAMPLE III

Synthesis and Characterization of Butyrylcholinesterase Variant Libraries

This example describes the synthesis and characterization of butyrylcholinesterase variant libraries expressed in mammalian cells.

In order to facilitate the synthesis of libraries of butyrylcholinesterase variants, DNA encoding wild-type human butyrylcholinesterase, a truncated, enzymatically active, monomeric version of human butyrylcholinesterase, and the A328Y mutant that displays a four-fold increased cocaine hydrolysis activity are cloned into a modified doublelox targeting vector, using unique restriction sites. In preliminary assays the wild-type human butyrylcholinesterase was captured more efficiently and, therefore, serves as the initial DNA template for the synthesis of libraries of butyrylcholinesterase variants.

Synthesis of Focused Libraries of Butyrylcholinesterase Variants by Codon-based Mutagenesis.

A variety of information can be used to focus the synthesis of the initial libraries of butyrylcholinesterase variants to discreet regions. For example, butyrylcholinesterase and Torpedo acetylcholinesterase (AChE) share a high degree of homology (53% identity). Furthermore, residues 4 to 534 of Torpedo AChE can be aligned with residues 2 to 532 of butyrylcholinesterase without deletions or insertions. The catalytic triad residues (butyrylcholinesterase residues Ser198, Glu325, and His438) and the intrachain disulfides are all in the same positions. Due to the high degree of similarity between these proteins, a refined 2.8-Å x-ray structure of Torpedo AChE (Sussman et al., *Science* 253: 872–879 (1991)) has been used to model butyrylcholinesterase structure (Harel et al., supra, 1992)).

Studies with cholinesterases have revealed that the catalytic triad and other residues involved in ligand binding are positioned within a deep, narrow, active-site gorge rich in hydrophobic residues (reviewed in Soreq et al., *Trends Biochem. Sci.* 17:353–358 (1992)). The sites of seven focused libraries of butyrylcholinesterase variants (FIG. 2, underlined residues) were selected to include amino acids determined to be lining the active site gorge (FIG. 2, hydrophobic active site gorge residues are shaded).

In addition to the structural modeling of butyrylcholinesterase, butyrylcholinesterase biochemical data was integrated into the library design process. For example, characterization of naturally occurring butyrylcholinesterases with altered cocaine hydrolysis activity and site-directed mutagenesis studies provide information regarding amino acid positions and segments important for cocaine hydrolysis activity (reviewed in Schwartz et al., *Pharmac. Ther.* 67: 283–322(1995)). Moreover, comparison of sequence and cocaine hydrolysis data of butyrylcholinesterases from different species can also provide information regarding regions important for cocaine hydrolysis activity of the molecule based on comparison of the cocaine hydrolysis activities of these butyrylcholinesterases. The A328Y mutant described above is present in the library corresponding to SEQ ID NO: 8 and serves as a control to demonstrate the quality of the library synthesis and expression in mammalian cells as well as the sensitivity of the microtiter-based cocaine hydrolysis assay.

The seven regions of butyrylcholinesterase selected for focused library synthesis (summarized in Table 2) span residues that include the 8 aromatic active site gorge residues (W82, W112, Y128, W231, F329, Y332, W430 and Y440) as well as two of the catalytic triad residues. The integrity of intrachain disulfide bonds, located between $^{65}$Cys-$^{92}$Cys, $^{252}$Cys-$^{263}$Cys, and $^{400}$Cys-$^{519}$Cys is maintained to ensure functional butyrylcholinesterase structure. In addition, putative glycosylation sites (N-X-S/T) located at residues 17, 57, 106, 241, 256, 341, 455, 481, 485, and 486 also are avoided in the library syntheses. In total, the seven focused libraries span 79 residues, representing approximately 14% of the butyrylcholinesterase linear sequence, and result in the expression of about 1500 distinct butyrylcholinesterase variants.

Libraries of nucleic acids corresponding to the seven regions of human butyrylcholinesterase to be mutated are synthesized by codon-based mutagenesis, as described above and as depicted schematically in FIG. 7. Briefly, multiple DNA synthesis columns are used for synthesizing the oligonucleotides by β-cyanoethyl phosphoramidite chemistry, as described previously by Glaser et al., supra, 1992. In the first step, trinucleotides encoding for the amino acids of butyrylcholinesterase are synthesized on one column while a second column is used to synthesize the trinucleotide NN(G/T), where N is a mixture of dA, dG, dC, and dT cyanoethyl phosphoramidites. Using the trinucleotide NN(G/T) results in thorough mutagenesis with minimal degeneracy, accomplished through the systematic expression of all twenty amino acids at every position.

Following the synthesis of the first codon, resins from the two columns are mixed together, divided, and replaced in four columns. By adding additional synthesis columns for each codon and mixing the column resins in the manner illustrated in FIG. 7, pools of degenerate oligonucleotides will be segregated based on the extent of mutagenesis. The resin mixing aspect of codon-based mutagenesis makes the process rapid and cost-effective because it eliminates the need to synthesize multiple oligonucleotides. In the present study, the pooi of oligonucleotides encoding single amino acid mutations is used to synthesize focused butyrylcholinesterase libraries.

The oliganucleotides encoding the butyrylcholinesterase variants containing a single amino acid mutation is cloned into the doublelox targeting vector using oligonucleotide-directed mutagenesis (Kunkel, supra, 1985). To improve the mutagenesis efficiency and diminish the number of clones expressing wild-type butyrylcholinesterase, the libraries are synthesized in a two-step process. In the first step, the butyrylcholinesterase DNA sequence corresponding to each library site is deleted by hybridization mutagenesis. In the second step, uracil-containing single-stranded DNA for each deletion mutant, one deletion mutant corresponding to each library, is isolated and used as template for synthesis of the libraries by oligonucleotide-directed mutagenesis. This approach has been used routinely for the synthesis of antibody libraries and results in more uniform mutagenesis by removing annealing biases that potentially arise from the differing DNA sequence of the mutagenic oligonucleotides. In addition, the two-step process decreases the frequency of wild-type sequences relative to the variants in the libraries, and consequently makes library screening more efficient by eliminating repetitious screening of clones encoding wild-type butyrylcholinesterase.

The quality of the libraries and the efficiency of mutagenesis is characterized by obtaining DNA sequence from approximately 20 randomly selected clones from each library. The DNA sequences demonstrate that mutagenesis occurs at multiple positions within each library and that multiple amino acids were expressed at each position. Furthermore, DNA sequence of randomly selected clones demonstrates that the libraries contain diverse clones and are not dominated by a few clones.

Optimization of Transfection Parameters for Site-specific Integration

Optimization of transfection parameters for Cre-mediated site-specific integration was achieved utilizing Bleomycin Resistance Protein (BRP) DNA as a model system.

Cre recombinase is a well-characterized 38-kDa DNA recombinase (Abremski et al., *Cell* 32:1301–1311 (1983)) that is both necessary and sufficient for sequence-specific recombination in bacteriophage P1. Recombination occurs between two 34-base pair loxP sequences each consisting of two inverted 13-base pair recombinase recognition sequences that surround a core region (Sternberg and Hamilton, *J. Mol. Biol.* 150:467–486 (1981a); Sternberg and Hamilton, *J. Mol. Biol.,* 150:487–507 (1981b)). DNA cleavage and strand exchange occurs on the top or bottom strand at the edges of the core region. Cre recombinase also catalyzes site-specific recombination in eukaryotes, including both yeast (Sauer, *Mol. Cell. Biol.* 7:2087–2096 (1987)) and mammalian cells (Sauer and Henderson, *Proc. Natl. Acad. Sci. USA,* 85:5166–5170 (1988); Fukushige and Sauer, *Proc. Natl. Acad. Sci. U.S.A.* 89:7905–7909 (1992); Bethke and Sauer, *Nuc. Acids Res.,* 25:2828–2834 (1997)).

Calcium phosphate transfection of 13–1 cells was previously demonstrated to result in targeted integration in 1% of the viable cells plated (Bethke and Sauer, *Nuc. Acids Res.,* 25:2828–2834 (1997)). Therefore, initial studies were conducted using calcium phosphate to transfect 13–1 cells with 4 μg pBS185 and 10, 20, 30, or 40 μg of pBS397-fl(+)/BRP. The total level of DNA per transfection was held constant using unrelated pBluescript II KS DNA (Stratagene; La Jolla, Calif.), and transformants were selected 48 hours later by replating in media containing 400 μg/ml geneticin. Colonies were counted 10 days later to determine the efficiency of targeted integration. Optimal targeted integration was typically observed using 30 μg of targeting vector and 4 μg of Cre recombinase vector pBS185, consistent with the 20 μg targeting vector and 5 μg of pBS185 previously reported (Bethke and Sauer, *Nuc. Acids Res.,* 25:2828–2834 (1997)). The frequency of targeted integration observed was generally less than 1%. Despite the sensitivity of the calcium phosphate methodology to the amount of DNA used and the buffer pH, targeted integration efficiencies observed were sufficient to express the protein libraries.

As shown in Table 5, several cell lines as well as other transfection methods were also characterized. As disclosed herein, Flp recombinase also can used to target insertion of exogenous DNA into a particular site in the genome as described by Dymecki, supra,1996. The target site for Flp recombinase consists of 13 base-pair repeats separated by an 8 base-pair spacer: 5'-GAAGTTCCTATTC [TCTAGAAA] GTATAGGAACTTC- 3' (SEQ ID NO: 24). Briefly, variant libraries corresponding to the region of butyrylcholinesterase corresponding to amino acids 277–289 (SEQ ID NO: 13) of butyryicholinesterase (shown as region 5 in Table 2) were transfected into mammalian cells using flp recombinase and the 293T cell line. Table 5 shows the butyryicholinesterase variants S285G, P285Q and P285S that were identified and characterized using the methods described herein utilizing Flp recombinase and the 293T human cell line.

In general, lipid-mediated transfection methods are more efficient than methods that alter the chemical environment, such as calcium phosphate and DEAE-dextran transfection. In addition, lipid-mediated transfections are less affected by contaminants in the DNA preparations, salt concentration, and pH and thus generally provide more reproducible results (Felgner et al., *Proc. Natl. Acad. Sci. USA,* 84:7413–7417 (1987)). Consequently, a formulation of the neutral lipid dioleoyl phosphatidylethanolamine and a cationic lipid, termed GenePORTER transfection reagent (Gene Therapy Systems; San Diego, Calif.), was evaluated as an alternative transfection approach. Briefly, endotoxin-free DNA was prepared for both the targeting vector pBS397-fl(+)/BRP and the Cre recombinase vector pBS185 using the EndoFree Plasmid Maxi kit (QIAGEN; Valencia, Calif.). Next, 5 µg pBS185 and varying amounts of pBS397-fl(+)/BRP were diluted in serum-free medium and mixed with the GeneP-ORTER transfection reagent. The DNA/lipid mixture was then added to a 60–70% confluent monolayer of 13–1 cells consisting of approximately $5 \times 10^5$ cells/100-mm dish and incubated at 37° C. Five hours later, fetal calf serum was added to 10%, and the next day the transfection media was removed and replaced with fresh media.

Transfection of the cells with variable quantities of the targeting vector yielded targeted integration efficiencies ranging from 0.1% to 1.0%, with the optimal targeted integration efficiency observed using 5 µg each of the targeting vector and the Cre recombinase vector. Lipid-based transfection of the 13–1 host cells under the optimized conditions resulted in 0.5% targeted integration efficiency being consistently observed. A 0.5% targeted integration is slightly less than the previously reported 1.0% efficiency (Bethke and Sauer, *Nuc. Acids Res.,* 25:2828–2834 (1997)), and is sufficient to express large protein libraries and allows expressing libraries of protein variants in mammalian cells.

TABLE 5

Expression of a single butyrylcholinesterase variant per cell using either stable or transient cell transfection.

| Cell Line | Expression | Integration Method | Integration? (PCR) | Integration? (Activity) |
|---|---|---|---|---|
| NIH3T3 (13-1) | Transient (lipid-based) | N/A | N/A | Transient, very low activity |
| NIH3T3 (13-1) | Stable | Cre recombinase | Yes | No measurable activity |
| CHO | Transient (lipid-based) | N/A | N/A | Transient, measurable activity (colorimetric and cocaine hydrolysis) |
| 293 | Transient (lipid-based) | N/A | N/A | Transient, measurable activity (colorimetric and cocaine hydrolysis) |
| 293 | Stable | Flp recombinase | Yes | Measurable activity (colorimetric and cocaine hydrolysis) |

These results demonstrate optimization of transfection conditions for targeted insertion in NIH3T3 13–1 cells. Conditions for a simple, lipid-based transfection method that required a small amount of DNA and generated reproducible 0.5% targeting efficiency were established.

Expression of Butyrylcholinesterase Variant Libraries in Mammalian Cells

Each of the seven libraries of butyrylcholinesterase variants are transformed into a host mammalian cell line using the doublelox targeting vector and the optimized transfection conditions described above. Following Cre-mediated transformation the host cells are plated at limiting dilutions to isolate distinct clones in a 96-well format. Cells with the butyrylcholinesterase variants integrated in the Cre/lox targeting site are selected with geneticin. Subsequently, the DNA encoding butyrylcholinesterase variants from 20–30 randomly selected clones from each library are sequenced and analyzed as described above. Briefly, total cellular DNA is isolated from about $10^4$ cells of each clone of interest using DNeasy Tissue Kits (Qiagen, Valencia, Calif.). Next, the butyrylcholinesterase gene is amplified using PfuTurbo DNA polymerase (Stratagene; La Jolla, Calif.) and an aliquot of the PCR product is then used for sequencing the DNA encoding butyrylcholinesterase variants from randomly selected clones by the fluorescent dideoxynucleotide termination method (Perkin-Elmer, Norwalk, Conn.) using a nested oligonucleotide primer.

As described previously, the sequencing demonstrates uniform introduction of the library and the diversity of mammalian transformants resembles the diversity of the library in the doubleox targeting vector following transformation of bacteria.

TABLE 6

Identification and characteristics of butyrylcholinesterase variant with enhanced cocaine hydrolase activity.

| Clone | Sequence | Relative $V_{max}/K_m$ |
|---|---|---|
| 5.2.390F | Wild-type human BChE A328W | 1.00 13.4 |
| 5.2.258F | S287G | 4.3 |
| 5.2.444F | P285Q | 3.9 |

TABLE 6-continued

Identification and characteristics of butyrylcholinesterase variant with enhanced cocaine hydrolase activity.

| Clone | Sequence | Relative $V_{max}/K_m$ |
|---|---|---|
| 5.2.600F | P285S | 2.8 |

As described herein, a library corresponding to region five of butyrylcholinesterase was expressed and individual variants were screened by measuring the hydrolysis of [$^3$H]-cocaine using the microtiter assay. The catalytic efficiency ($V_{max}/K_m$) of variants with enhanced activity were characterized using the microtiter assay to determine their relative $K_m$ and $V_{max}$. Three butyrylcholinesterase variants were identified that have enhanced cocaine hydrolase activity: S287G (SEQ ID NO: 4), P285Q (SEQ ID NO: 6) and P285S (SEQ ID NO: 8).

EXAMPLE IV

Characterization of Butyrylcholinesterase Variants that Display Enhanced Cocaine Hydrolysis Activity This example describes the molecular characterization of butyrylcholinesterase variants that display enhanced cocaine hydrolysis activity in the microtiter assay described below. The cocaine hydrolysis activity measured in the microtiter assay format is further confirmed using greater amounts of the butyrylcholinesterase variants of interest. In addition to the microtiter-based assay, the activity of the clones is demonstrated in solution phase with product formation measured by the HPLC assay to verify the increased cocaine hydrolysis activity of the butyrylcholinesterase variants and confirm that the enhanced hydrolysis is at the benzoyl ester group.

The kinetic constants for wild-type butyrylcholinesterase and the best variants are determined and used to compare the catalytic efficiency of the variants relative to wild-type butyrylcholinesterase. $K_m$ values for (−)-cocaine are determined at 37° C. $V_{max}$ and $K_m$ values are calculated using Sigma Plot (Jandel Scientific, San Rafael, Calif.). The number of active sites of butyrylcholinesterase is determined by the method of residual activity using echothiopate iodide or diisopropyl fluorophosphates as titrants, as described previously by Masson et al., *Biochemistry* 36: 2266–2277 (1997). Alternatively, the number of butyrylcholinesterase active sites is estimated using an ELISA to quantitate the mass of butyrylcholinesterase or butyrylcholinesterase variants present in culture supernatants. Purified human butyrylcholinesterase is used as the standard for the ELISA quantitation assay. The catalytic rate constant, $k_{cat}$, is calculated by dividing $V_{max}$ by the concentration of active sites. Finally, the catalytic efficiencies of the best variants are compared to wild-type butyrylcholinesterase by determining $k_{cat}/K_m$ for each butyrylcholinesterase variant.

In order to better characterize all the clones expressing butyrylcholinesterase variants with increased cocaine hydrolysis activity, the DNA encoding the variants is sequenced. DNA sequencing reveals the precise location and nature of the mutations and thus, quantifies the total number of distinct butyrylcholinesterase variants identified. Screening of each library is complete when clones encoding identical butyrylcholinesterase mutations are identified on multiple occasions, indicating that the libraries have been screened exhaustively.

EXAMPLE V

Synthesis and Characterization of Combinatorial Butyrylcholinesterase Variant Libraries This example demonstrates synthesis and characterization of combinatorial libraries of butyrylcholinesterase variants expressed in mammalian cells.

The beneficial mutations identified from screening libraries of butyrylcholinesterase variants containing a single amino acid mutation are combined in vitro to further improve the butyrylcholinesterase cocaine hydrolysis activity. The positive combination of beneficial mutations designated biochemical additivity has been observed on multiple occasions. For example, the iterative process of increasing antibody affinity in a stepwise fashion through the accumulation and subsequent combination of beneficial mutations has led to the identification of antibodies displaying 500-fold enhanced affinity using variant libraries containing less than 2,500 distinct variants. Importantly, the principle of biochemical additivity is not restricted to improving the affinity of antibodies, and has been exploited to achieve improvements in other physical properties, such as thermostability, catalytic efficiency, or enhanced resistance to pesticides.

The best mutations identified from screening the seven focused butyrylcholinesterase libraries are used to synthesize a combinatorial library. The number of distinct variants in the combinatorial library is expected to be small, typically a fraction of the number of distinct variants from the initial libraries. For example, combinatorial analysis of single mutations at eight distinct sites would require a library that contains $2^8$, or 256, unique variants. The combinatorial library is synthesized by oligonucleotide-directed mutagenesis, characterized, and expressed in the mammalian host cell line. Variants are screened and characterized as described above. DNA sequencing reveals additive mutations.

EXAMPLE VI

Expression and Purification of Butyrylcholinesterase Variants

This example demonstrates the expression in a mammalian cell line and subsequent purification of butyrylcholinesterase variants.

Clones expressing the most catalytically active butyrylcholinesterase variants, as well as wild-type butyrylcholinesterase, are used to establish larger-scale cultures in order to purify quantities of the enzyme necessary for in vivo studies. It is estimated that approximately 100 mg each of wild-type butyrylcholinesterase and the optimal variant is required to complete the in vivo toxicity and addiction studies in rats as described below.

The butyrylcholinesterase variants of interest are cloned into the pCMV/Zeo vector (Invitrogen, Carlsbad, Calif.) using unique restriction sites. The cloning of the variants is verified using restriction mapping and DNA sequencing. Subsequently, the variants are expressed in transfected Chinese Hamster ovary cells CHO Kl (ATCC CCL 61). CHO cells were selected for expression because butyrylcholinesterase is a glycoprotein and these cells have been previously used for the expression of recombinant human therapeutic glycoproteins (Goochee et al., *Biotechnology* 9:1347–1355 (1991); Jenkins and Curling, *Enzyme Microb. Technol.* 16:354–364 (1994)) as well as fully active recombinant butyrylcholinesterase (Masson et al., supra, 1997). Initially, the CHO cells are transiently transfected with all the butyrylcholinesterase variants to confirm expression of functional butyrylcholinesterase. Subsequently, the cells are stably transfected and clones expressing butyrylcholinesterase variants are selected using the antibiotic Zeocin (Invitrogen. Carlsbad, Calif.). Colonies are picked with a sterile cotton-tipped stick and transferred to 24-well plates. The butyrylcholinesterase expression is measured and the colonies with the highest activity are further expanded. The kinetic constants of the butyrylcholinesterase variants are determined to ensure that expression in CHO cells does not diminish the enzymatic activity compared to butyrylcholinesterase variants expressed in NIH3T3 cells.

The cells are expanded in T175 flasks and expanded further into multiple 3L spinner flasks until approximately $5 \times 10^8$ cells are obtained. Subsequently, the cell lines are transferred to CELL-PHARM System 2000 hollow fiber cell culture systems (Unisyn Technologies, Hopkinton, Mass.) for the production and continuous recovery of butyrylcholinesterase. The hollow fiber system permits high cell densities to be obtained ($10^8$/ml) from which 60–120 ml of concentrated butyrylcholinesterase is harvested each day. It is anticipated that it requires one month to produce sufficient quantities of butyrylcholinesterase for further evaluation.

The concentrated recombinant butyrylcholinesterase harvested from the hollow fiber systems are purified, essentially as described previously (Masson et al., supra, 1997). The serum-free medium is centrifuged to remove particulates, its ionic strength is reduced by dilution with two volumes of water, and subsequently, the sample is loaded on a procainamide Sepharose affinity column. Butyrylcholinesterase is eluted with procainamide, purified further by ion exchange chromatography and concentrated. A recombinant butyrylcholinesterase mutant expressed in CHO cells has previously been enriched to 99% purity with over 50% yields using this purification approach (Lockridge et al., *Biochemistry* 36:786–795 (1997)). The enzyme is filter-sterilized through a 0.22-μm membrane and stored at 4° C. Under these conditions, butyrylcholinesterase retains over 90% of its original activity after 18 months (Lynch et al., *Toxicology and Applied Pharmacol.* 55:83–91 (1999))

EXAMPLE VII

Evaluation of Wild-Type Butyrylcholinesterase and Butyrylcholinesterase Variants This example describes the evaluation of wild-type butyrylcholinesterase and butyrylcholinesterase variants in rat cocaine toxicity and reinforcement models.

Butyrylcholinesterase variants that display increased cocaine hydrolysis activity in vitro display greater potency for the treatment of cocaine toxicity and addiction in vivo. To characterize the butyrylcholinesterase variants in vivo, an acute overdose model is used to measure the potency of butyrylcholinesterase variants for toxicity, while models of reinforcement and discrimination are used to predict the potency of butyrylcholinesterase variants for the treatment of addiction. Although the pharmacokinetics of human butyrylcholinesterase variants are not expected to be optimal in models, the rat cocaine models are well characterized and require significantly smaller quantities of purified butyrylcholinesterase than do primate models. It is anticipated that both wild-type butyrylcholinesterase and the butyrylcholinesterase variants with increased cocaine hydrolysis activity display dose-dependent responses. Furthermore, the butyrylcholinesterase variant optimized for cocaine hydrolysis activity are efficacious at substantially smaller doses than the wild-type butyrylcholinesterase.

Modification of the Toxicity of Cocaine

The effect of butyrylcholinesterase variants on cocaine toxicity is evaluated as previously described in rat model of overdose by Mets et al., *Proc. Nat. Acad. Sci. USA* 95:10176–10181 (1998). This model uses co-infusion of catecholamines because variable endogenous catecholamine levels have been shown to affect cocaine toxicity (Mets et al., *Life Sci.* 59:2021–2031 (1996)). Infusion of cocaine at 1 mg/kg/min produces $LD_{50}$=10 mg/kg and $LD_{90}$=16 mg/kg when the levels of catecholamines are standardized.

Six groups of six rats each are used in this study. The rats are Sprague-Dawley males, weighing 250–275 g upon receipt in the vivarium, which is maintained on a 12 hour light-dark cycle. The rats have food and water available ad libitum at all times. Prior to treatment the rats are fitted with femoral arterial and venous catheters and permitted to recover. Subsequently, the rats are treated with varying amounts of the butyrylcholinesterase variants (0.35, 1.76, or 11.8 mg/kg) or equivalent volumes of saline 15 minutes prior to the co-infusion of catecholamines and cocaine (1 mg/kg/min). The infusion is for 16 minutes to deliver the $LD_{90}$ of cocaine, unless the animals expire sooner. Based on the relative catalytic efficiencies of wild-type butyrylcholinesterase and the previously described catalytic antibody (Mets et al., supra, 1998), it is anticipated that increasing doses of butyrylcholinesterase confer increased survival rate to the rats relative to the saline controls and that the highest butyrylcholinesterase dose (11.8 mg/kg) protects all the animals. A butyrylcholinesterase variant that hydrolyzes cocaine 10-fold more efficiently in vitro is expected to confer protection to all of the animals at a lower dose (1 mg/kg, for example).

Modification of the Abuse of Cocaine

The discriminative and reinforcing pharmacological effects of cocaine are believed to most closely reflect the actions of cocaine that embody abuse of the drug. Therefore, the butyrylcholinesterase variants are evaluated in both cocaine reinforcement and cocaine discrimination models in rats.

The rat model of the reinforcing effects of cocaine has been used extensively to evaluate other potential therapies for cocaine (Koob et al., *Neurosci. Lett.* 79: 315–320(1987); Hubner and Moreton, *Psychopharmacology* 105: 151–156 (1991); Caine and Koob, *J. Pharmacol. Exp. Ther.* 270: 209–218 (1994); Richardson et al., *Brain Res.* 619: 15–21 (1993)).

Male Sprague-Dawley rats are maintained as described above. Six operant chambers (Med Associates, St. Albans, Vt.), equipped with a house light, retractable lever, dipper mechanism, red, yellow, and green stimulus lights, and a pneumatic syringe-drive pump apparatus (IITC Life Sciences, Inc., Woodland Hills, Calif.) for drug delivery are interfaced with an IBM-compatible computer through input and output cards (Med Associates, Inc., St. Albans, Vt.). The chambers are housed within an air conditioned, sound attenuating cubicle (Med Associates). Custom self-administration programs, controlling scheduled contingencies and stimulus arrays within the operant chambers, are written using the Med-PC programming language for DOS.

The reinforcing effects of cocaine are assessed in a model that quantitates the number of injections taken by rats under conditions in which intravenous administration is contingent upon a response made by the animal (Mets et al., supra, 1998). The rats are trained in the operant conditioning chambers to press a lever in order to gain access to 0.5 ml of a sweetened milk solution. After the rats have acquired the lever-press response on a fixed-ratio 1 (FR1) schedule of reinforcement, the response requirements are successively increased to an FR5 schedule. When the rats display stable rates of milk-maintained responding over three consecutive days on this schedule (less than 10% variability in reinforcer deliveries over the one-hour session) a catheter is surgically introduced in the left internal jugular vein and the rats are given a minimum of two days to recover from surgery.

On the first operant training session following surgery, rats are allowed to respond on the lever, in a one-hour session, for the simultaneous 5-second delivery of both milk and an intravenous bolus of cocaine (0.125 mg/kg/injection). The milk is then removed from the chamber and for the next three days, the rats are given access to one of three doses of cocaine (0.125, 0.25, or 0.5 mg/kg/injection) for one hour each, in self-administration sessions six hours in duration. Thus, the rats are allowed access to each dose twice per session and the doses are presented in repeated ascending order (i.e., 0.125, 0.25, 0.5, 0.125, 0.25, 0.5 mg/kg/injection). Within each one-hour long dose-component, the original FR5 schedule with a 10-second timeout is retained. In addition, 10-minute timeout periods are instituted after each dose component in an attempt to minimize carryover effects across the individual one-hour sessions.

When the rats display consistent cocaine self-administration (over 160 injections per six-hour session with less than 15% variability) over three consecutive days, they are placed on a schedule in which smaller doses, as well as saline, are available during single daily sessions. Each session is divided into two components, with saline and three doses of cocaine available in each component. The first component of each session provides access to a series of low doses (0–0.0625 mg/kg/injection) while the second component provides access to a wider range of doses (0–0.5 mg/kg/injection).

After the rates of cocaine self-administration are stabilized the rats are divided between six groups and each group (n=6 rats) is given 0.35, 1.76, or 11.8 mg/kg of either wild-type butyrylcholinesterase, the optimized butyrylcholinesterase variant or an equivalent volume of saline 30 minutes prior to the beginning of the daily self-administration sessions. The effects of the pretreatment are monitored for several days until the cocaine self-administration behavior of the rat returns to baseline.

Using a fixed ratio (FR) schedule, the number of injections is limited only by the duration of the session and consequently, the number of injections is used as the dependent variable to compare the potency of optimized butyrylcholinesterase with wild-type butyrylcholinesterase. Following administration of varying concentrations of wild-type butyrylcholinesterase or the optimized butyrylcholinesterase variant, the dose response curves are analyzed using a mixed factor MANOVA. The butyrylcholinesterase concentration (0.35, 1.76, or 11.8 mg/kg) is loaded as the between-subjects factor and the cocaine dose (0, 0.015, 0.03, 0.06, 0.125, 0.25, 0.5 mg/kg/injection) is loaded as the within-subjects factor. All individual comparisons across butyrylcholinesterase treatment groups at individual cocaine doses use the Tukey HSD post-hoc procedure (see Gravetter, F. J. and Wallnau, L. B., Statistics for the Behavioural Sciences (5th ed., 2000, Wadsworth Publ., Belmont, Calif.)) and the criterion for statistical significance is set at $p < 0.05$. At higher butyrylcholinesterase doses (11.8 mg/kg), the number of injections taken by the rats is expected to be lower than the untreated (saline) control group. Furthermore, rats treated with the butyrylcholinesterase variant displaying enhanced cocaine hydrolysis are expected to reduce their number of injections at a smaller dose (0.35 mg/kg) than the animals treated with the wild-type butyrylcholinesterase.

Drug discrimination is relevant to the subjective effect of cocaine in clinical situations and antagonism of cocaine discrimination following pretreatment is considered clear evidence of therapeutic potential (Holtzman, *Modern Methods in Pharmacology, Testing and Evaluation of Drug Abuse*, Wiley-Liss Inc., New York, (1990); Spealman, *NIDA Res. Mon.* 119: 175–179 (1992)). The most frequently used procedure to establish and evaluate the discriminative stimulus effect of drugs is to train animals in a controlled operant procedure to use the injected drug as a stimulus to control distribution of responding on two levers. Dose-effect curves consisting of distribution of the responses on the "drug-associated" lever as a function of drug dose are easily generated. These cocaine dose-effect curves can be altered by the administration of a competitive antagonist. The amount of the shift of the curve and time required for the original sensitivity of the animal to cocaine to return are useful data for evaluating the potential therapeutic use of wild-type butyrylcholinesterase and the optimized variant. The discriminative stimulus effects of cocaine in rat models have been used to evaluate the therapeutic potential of dopamine reuptake inhibitors, as well as agonists and antagonists to the dopamine receptors (Witkin et al., *J. Pharmacol. Exp. Ther.* 257: 706–713 (1989); Kantak et al, *J. Pharmacol. Exp. Ther.* 274: 657–665(1995); Barret and Appel, *Psychopharmacology* 99: 13–16 (1989); Callahan et al., *Psychopharmacology* 103: 50–55(1991)).

A multiple trial procedure for training and testing cocaine as a discriminative stimulus is used to evaluate the potency of butyrylcholinesterase in rats as previously described in Bertalmio et al. J. Pharmacol. Methods 7: 289–299 (1982) and Schecter, *Eur. J. Pharmacol.* 326: 113–118 (1997). A dose-response curve for cocaine is obtained in a single session in the presence of butyrylcholinesterase or the optimized butyrylcholinesterase variant. Subsequently, the recovery of the rat's original sensitivity to cocaine is tracked on a twice-weekly basis to assess the duration of action of the butyrylcholinesterase.

The rats are deprived to 80% of their free-feeding weight at the beginning of the experiment in order to train them in the food-reinforced operant procedure. Each rat is placed in an operant conditioning chamber equipped with two light stimuli and two retractable levers, one on either side of a milk delivery system and trained to press on one of the levers to receive access to 0.5 ml of sweetened condensed milk. Once the rats have learned to respond on this lever, a multiple-trials procedure is initiated. Each session consists of 6 trials with each trial lasting 15 minutes. The first 10 minutes of each trial are a blackout period, during which no lights are on and responding has no consequence. This 10-minute period allows for drug absorption in the subsequent testing phases of the study. The last 5 minutes of each trial are a milk-reinforced period (FR5). Once the rats respond consistently and rapidly during the 5-minute response period (signaling period), cocaine is introduced into the procedure.

Initially, 10 mg/kg cocaine is given 10 minutes prior to the beginning of three of six weekly sessions. During these sessions, the "non-cocaine" lever (saline) previously extended is retracted and the other, "cocaine-associated," lever is extended on the other side of the milk delivery cup.

Responses (initially only a single response; eventually five responses) on this second lever result in milk presentation if cocaine was administered prior to the session. The rats are being trained to respond on the second lever if they detect the interoceptive effects of the administered cocaine. Because cocaine's interoceptive effects are not believed to extend beyond 30 minutes, the sessions following cocaine administration lasts for only two trials (15 minutes each). At this juncture the rats do not receive a cocaine injection on three days of the week and on those days they are reinforced with milk (FR5) for responding on the available non-cocaine lever during the signaling periods of six trials. On the remaining three days of the week, the rats are given 10 mg/kg cocaine before the beginning of the session and are reinforced for responding on the available cocaine lever during the signaling periods on each of two trials.

Subsequently, each daily session is initiated with one to four trials without cocaine administration, followed by the administration of 10 mg/kg cocaine. Thus, each session ends with two trials in which responding on the cocaine-appropriate lever is required for food delivery. Although only the "correct" levers are extended during this phase, the critical step of making both levers available during the entire session is taken as soon as the animals learn to switch from the non-cocaine to the cocaine lever within daily sessions. Subsequently, each session begins with a 10-minute blackout period followed by presentation of both levers for five minutes. During the first 1 to 4 trials of a daily session, no cocaine is given, and 5 consecutive responses on the non-cocaine lever result in food during this 5-minute period. If the rat switches from one lever to the other or responds on the incorrect lever, he does not get reinforced and both levers are retracted for 10 seconds, at which time the levers are presented again and the trial restarted. At the start of the second, third, or fourth trial, 10 mg/kg cocaine are given and the rat is returned to the test box. When the light is illuminated and the levers presented on the next two trials, five consecutive responses on the cocaine lever are required for milk presentation to demonstrate that the rats are learning to switch their responding from the non-cocaine lever to the cocaine lever using the interoceptive effects of cocaine as a cue to tell them which lever is correct on a given trial.

A cocaine dose-effect curve is obtained as soon as the rats meet criterion of 80% correct lever selection on three consecutive sessions. On the first trial of a test session, saline is given. On subsequent trials, 0.1, 0.3, 1.0, 3.2, and 10 mg/kg cocaine is administered, each at the start of the 10 minute blackout that begins each trial. During these test trials, five consecutive responses on either lever result in milk presentation, but switching from one lever to the other prior to completion of an FR results in lever retraction for 10 seconds. It is anticipated that animals begin this session with responses on the non-cocaine lever and gradually increase the percent of responses made on the cocaine lever until all responses are made on that lever. Thus, a dose-response curve of lever selection versus dose of cocaine administered is established during each test session.

Once cocaine has been established as a discriminative stimulus, the rats are placed in separate groups (n=6 per group) that receive 0.35, 1.76, or 11.8 mg/kg of either wild-type butyrylcholinesterase or the optimized variant. The discriminative stimulus effects of cocaine is determined 30 minutes following enzyme administration and daily afterwards until sensitivity to cocaine is re-established. On the initial test session following administration of butyrylcholinesterase, larger doses of cocaine are given if there is no selection of the cocaine lever following any of the smaller test doses. Doses as large as 100 mg/kg cocaine are given if the animals fail to select the cocaine-appropriate lever following administration of 10 or 32 mg/kg cocaine. Because dose-response curves to cocaine can be obtained in a single session, this protocol provides information on the relative ability of the two types of butyrylcholinesterase to decrease the potency of cocaine as a discriminative stimulus, which is a relevant aspect of its abuse liability. The butyrylcholinesterase variant displaying enhanced cocaine hydrolysis activity in vitro is more potent.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A butyrylcholinesterase variant comprising an amino acid sequence comprising a sequence of amino acid residues 1 or 29 through 602, inclusive, of the amino acid sequence shown as SEQ ID NO:2, wherein said variant has tryptophan at amino acid position 356.

2. The butyrylcholinesterase variant of claim 1, having a 15-fold increase in cocaine hydrolysis activity compared to human butyrylcholinesterase.

* * * * *